US009334500B2

(12) United States Patent
Yu et al.

(10) Patent No.: US 9,334,500 B2
(45) Date of Patent: May 10, 2016

(54) METHODS AND PHARMACEUTICAL COMPOSITIONS FOR TREATING CANCER

(71) Applicant: Agency for Science, Technology and Research, Singapore (SG)

(72) Inventors: Qiang Yu, Singapore (SG); Shuet Theng Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/348,365

(22) PCT Filed: Sep. 28, 2012

(86) PCT No.: PCT/SG2012/000364
§ 371 (c)(1),
(2) Date: Mar. 28, 2014

(87) PCT Pub. No.: WO2013/048345
PCT Pub. Date: Apr. 4, 2013

(65) Prior Publication Data
US 2014/0335106 A1 Nov. 13, 2014

(30) Foreign Application Priority Data
Sep. 28, 2011 (SG) .................................. 201107036

(51) Int. Cl.
*C12N 15/11* (2006.01)
*C12N 15/113* (2010.01)
*A61K 31/517* (2006.01)
*A61K 31/713* (2006.01)
*A61K 45/06* (2006.01)
*A61K 31/47* (2006.01)
*A61K 31/4709* (2006.01)
*A61K 31/5377* (2006.01)
*A61K 31/519* (2006.01)
*A61K 31/7088* (2006.01)
*C12Q 1/68* (2006.01)

(52) U.S. Cl.
CPC ............ *C12N 15/1135* (2013.01); *A61K 31/47* (2013.01); *A61K 31/4709* (2013.01); *A61K 31/517* (2013.01); *A61K 31/519* (2013.01); *A61K 31/5377* (2013.01); *A61K 31/7088* (2013.01); *A61K 31/713* (2013.01); *A61K 45/06* (2013.01); *C12N 15/113* (2013.01); *C12Q 1/6881* (2013.01); *C12N 2310/14* (2013.01); *C12N 2320/31* (2013.01); *C12Q 2600/106* (2013.01)

(58) Field of Classification Search
CPC ............. C12N 15/113; C12N 15/1135; C12N 15/1137
See application file for complete search history.

(56) References Cited

U.S. PATENT DOCUMENTS

| 7,517,644 | B1 | 4/2009 | Smith | |
|---|---|---|---|---|
| 7,820,809 | B2 | 10/2010 | Khvorova et al. | |
| 2006/0084666 | A1* | 4/2006 | Harari .................. | A61K 31/517 514/263.34 |
| 2006/0194883 | A1 | 8/2006 | Ozaki et al. | |
| 2011/0021607 | A1* | 1/2011 | Clarke .................. | C12Q 1/6886 514/44 A |
| 2012/0070450 | A1* | 3/2012 | Ishikawa et al. ........... | 424/173.1 |
| 2013/0137584 | A1* | 5/2013 | Reiter .................. | C12Q 1/6886 506/2 |

FOREIGN PATENT DOCUMENTS

| WO | WO-00/02589 A1 | 1/2000 |
|---|---|---|
| WO | WO-2005/027830 A2 | 3/2005 |
| WO | WO-2008/043561 A2 | 4/2008 |
| WO | WO-2010/017443 A2 | 2/2010 |
| WO | WO 2010/1103416 * | 9/2010 |
| WO | WO-2011005793 A1 | 1/2011 |
| WO | WO-2012/071492 A1 | 5/2012 |

OTHER PUBLICATIONS

Gura (Science, 1997, 278:1041-1042).*
Kaiser (Science, 2006, 313: 1370).*
Gura (Science, 1995, 270:575-577).*
Pei and Tuschl (Nature Methods, 2006, 3: 670-676).*
Sekar et al. (Theranostics 2013 3(12): 964-985).*
Gerdes et al. (Front. Oncol. Dec. 18, 2014 doi: 10.3389/fonc.2014. 00366, pp. 1-12).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Benedict et al. (J. Exp. Medicine, 2001, 193(1) 89-99).*
Jiang et al. (J. Biol. Chem., 2003, 278(7) 4763-4769).*
Matsushita et al. (FEBS Letters, 1999, vol. 443, pp. 348-352).*
Singh et al. (Glycobiology, 2001, vol. 11, pp. 587-592).*
Ito, Hiromichi, et al., "Prostaglandin $E_2$ Enhances Pancreatic Cancer Invasiveness through an Ets-1—Dependent Induction of Matrix Metalloproteinase-2", *Cancer Research*, 64(20), (2004), 7439-7446.
Kita, Daisuke, et al., "Expression of Dominant-negative Form of Ets-1 Suppresses Fibronectin-stimulated Cell Adhesion and Migration Through Down-Regulation of Integrin α5 Expression in U251 Glioma Cell Line", *Cancer Research*, 61, (2001), 7985-7991.
Sureban, Sripathi, et al., "Nanoparticle-based delivery of siDCAMKL-1 increases microRNA-144 and inhibits colorectal cancer tumor growth via a Notch-1 dependent mechanism", *Journal of Nanobiotechnology*, 9(40), (2011), 1-13.
Xia, Hongping, et al., "miR-200a Regulates Epithelial-Mesenchymal to Stem-like Transition via ZEB2 and β-Catenin Signaling", *The Journal of Biological Chemistry*, 5(47), (2010), 36995-37004.
Zhang, Yan, et al., "miR-125b Is Methylated and Functions as a Tumor Suppressor by Regulating the ETS1 Proto-oncogene in Human Invasive Breast Cancer", *Cancer Research*, 71(10), (2011), 3552-3562.

(Continued)

*Primary Examiner* — Peter J Reddig
(74) *Attorney, Agent, or Firm* — Schwegman Lundberg & Woessner, P.A.

(57) ABSTRACT

A method of treating cancer by inhibiting expression of ubiquitin associated and SH3 domain containing B (UBASH3B) gene or by inhibiting the activity of UBASH3B protein or a functional variant thereof.

10 Claims, 18 Drawing Sheets

(56) References Cited

OTHER PUBLICATIONS

Zhao, Jian, et al., "Thirty-Kilodalton Tat-Interacting Protein Suppresses Tumor Metastasis by Inhibition of Osteopontin ranscription in Human Hepatocellular Carcinoma", *Hepatology*, 48(1), (2003), 265-275.

"International Application No. PCT/SG2012/000364, International Search Report and Written Opinion mailed Dec. 7, 2012", 32 pgs.

* cited by examiner

Figure 1 – cont'd
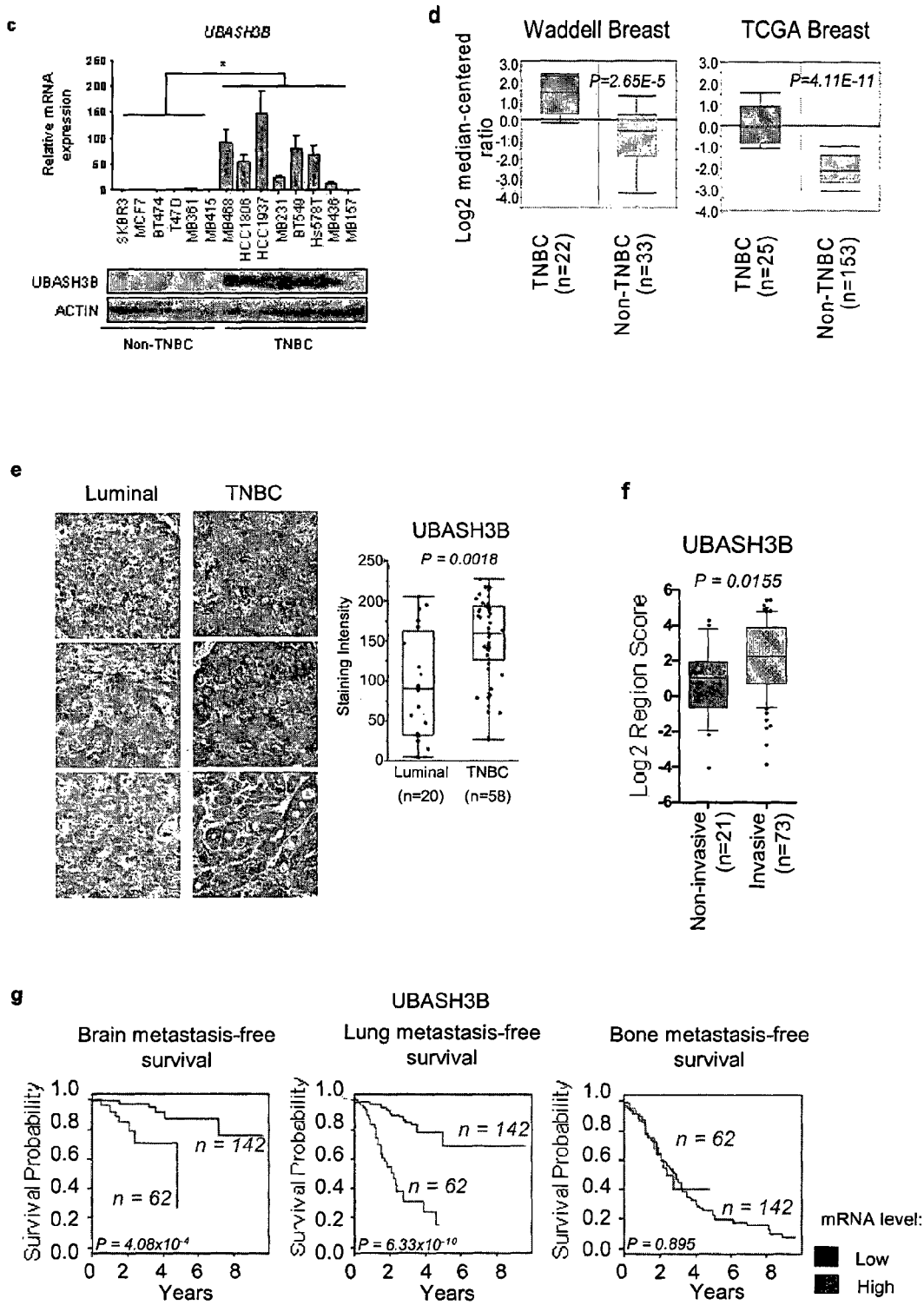

Figure 1 – cont'd
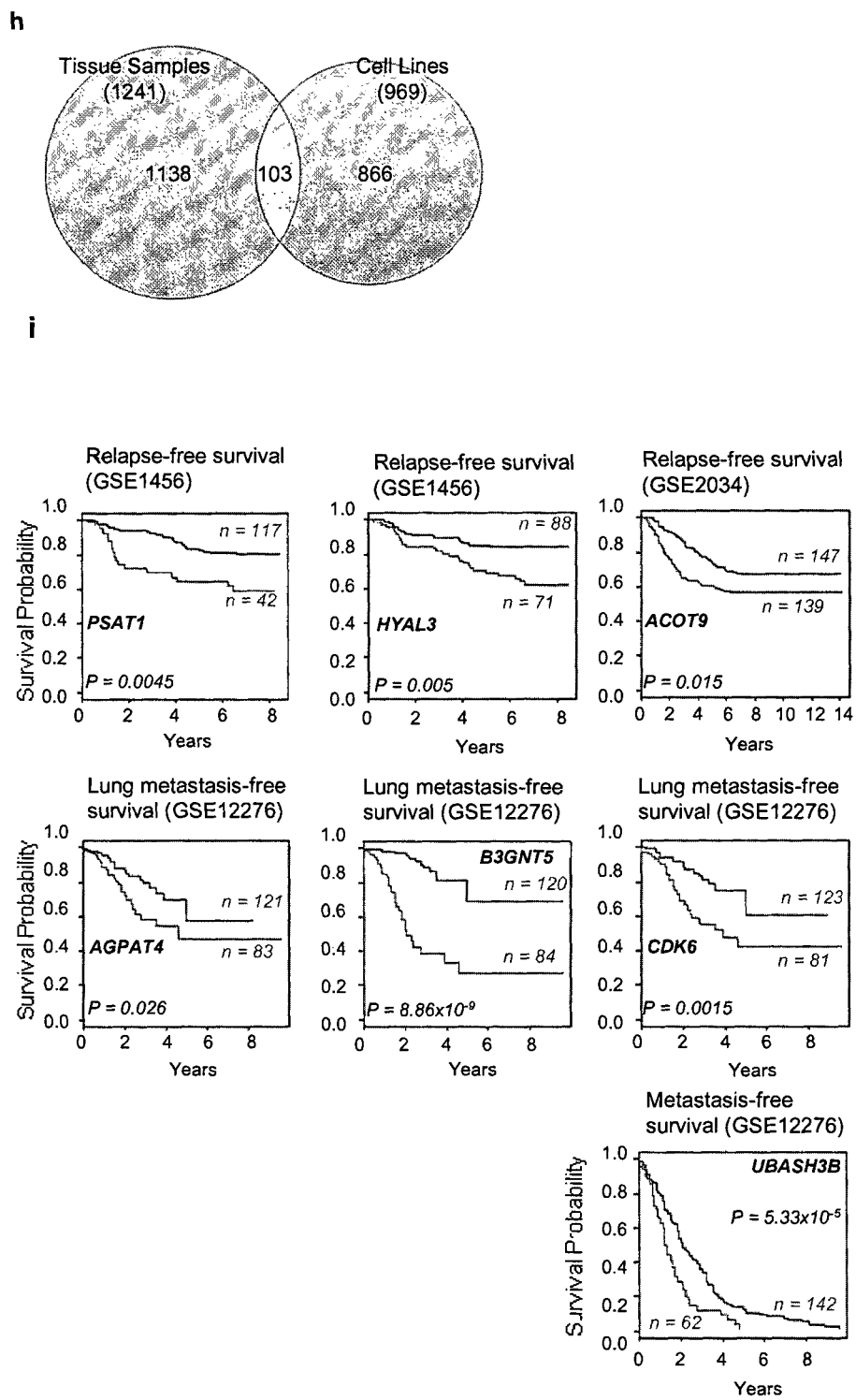

Figure 1 – cont'd
j
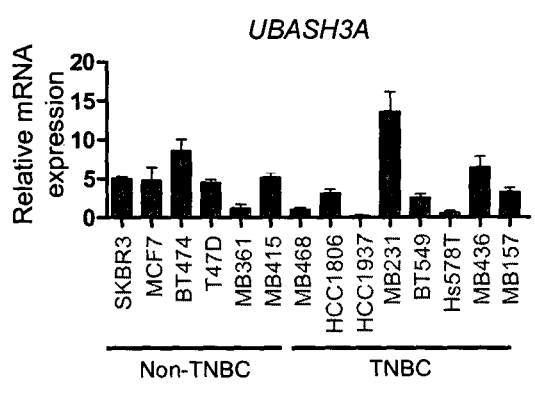
k
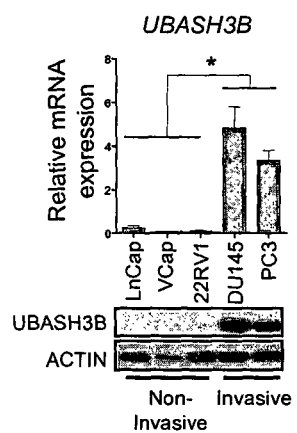
l
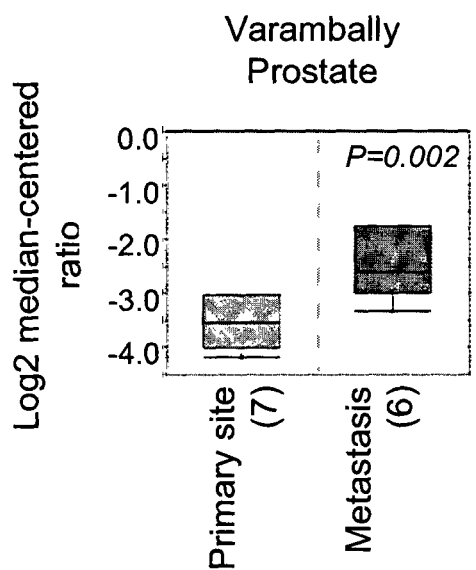

Figure 2 – cont'd
e
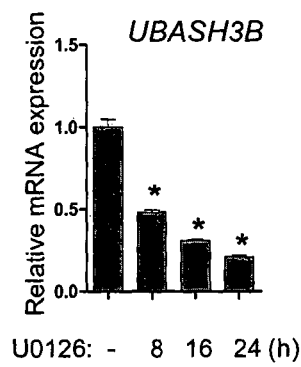
f
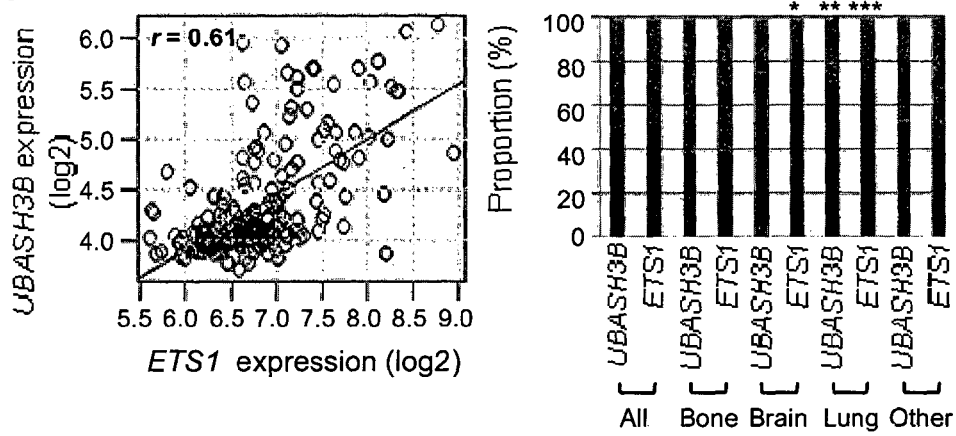
g
ETS1
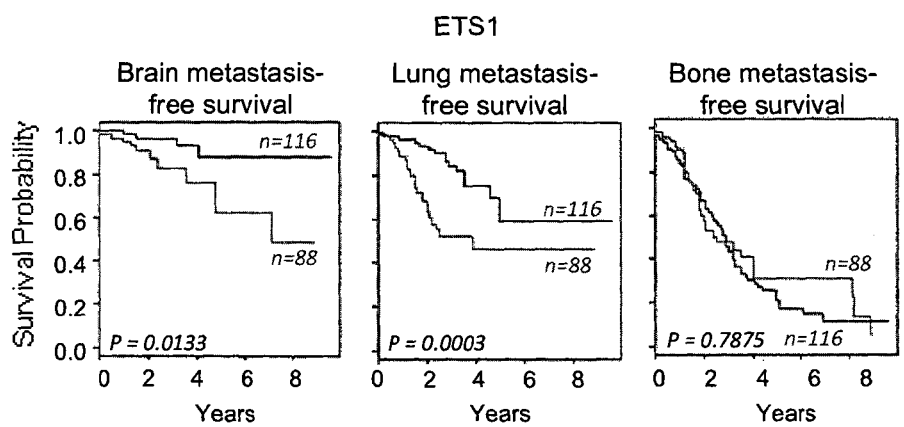

Figure 2 – cont'd
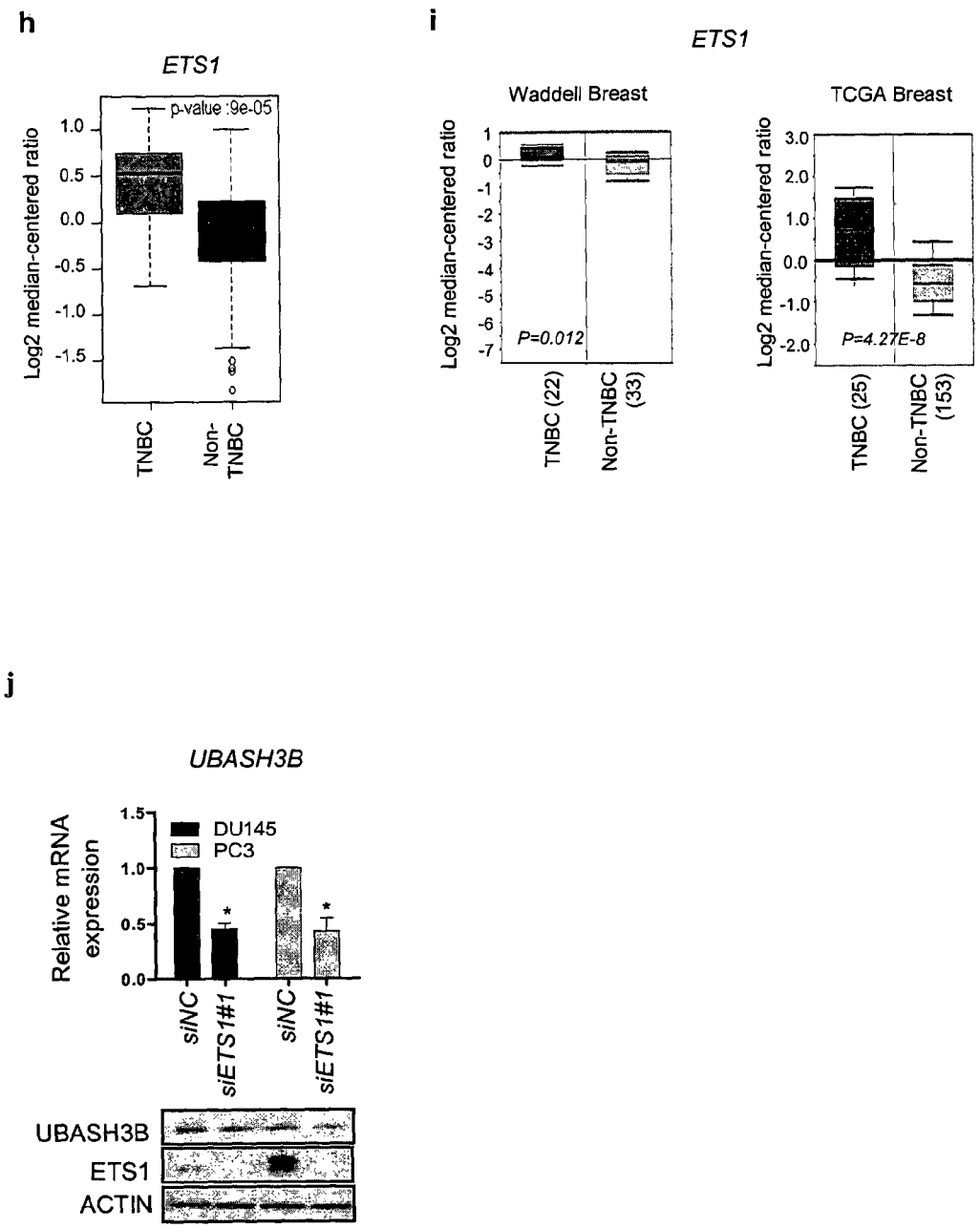

Figure 3 - cont'd
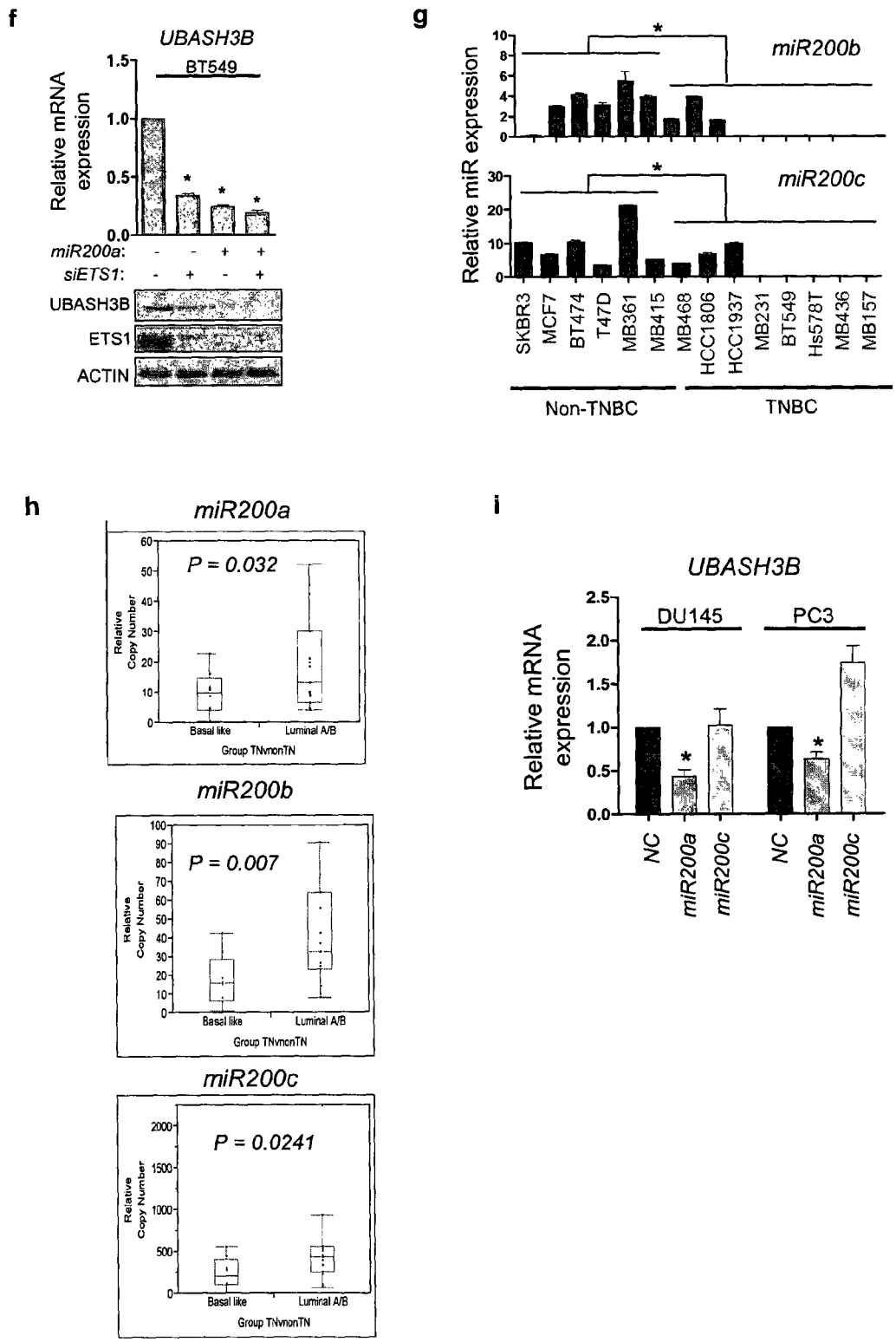

Figure 4 - cont'd
d
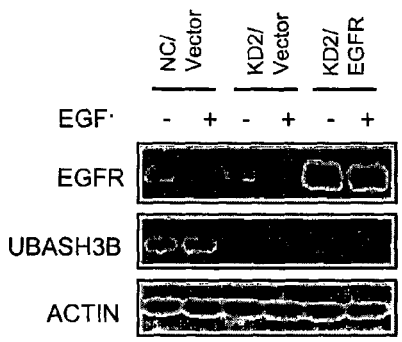
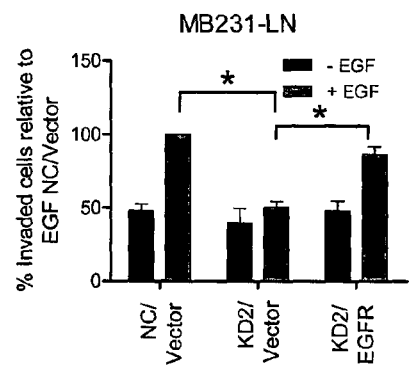
e
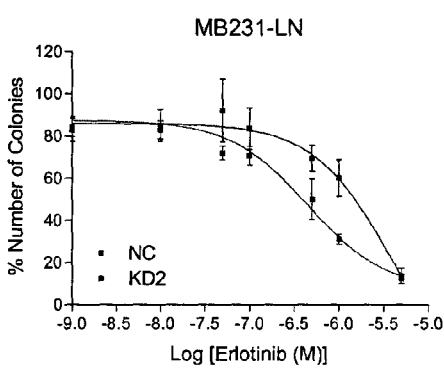
f
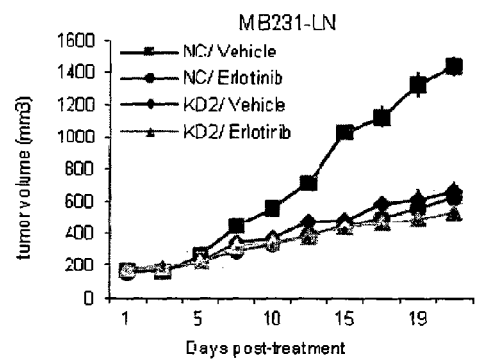
g
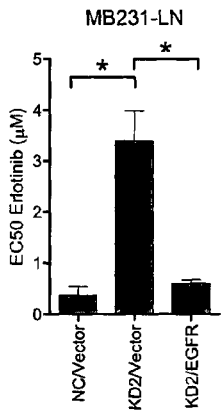
h
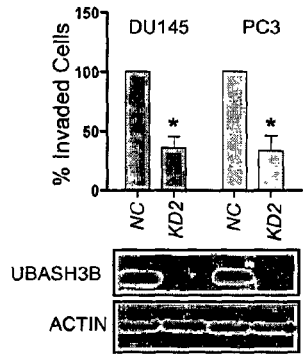

Figure 4 - cont'd
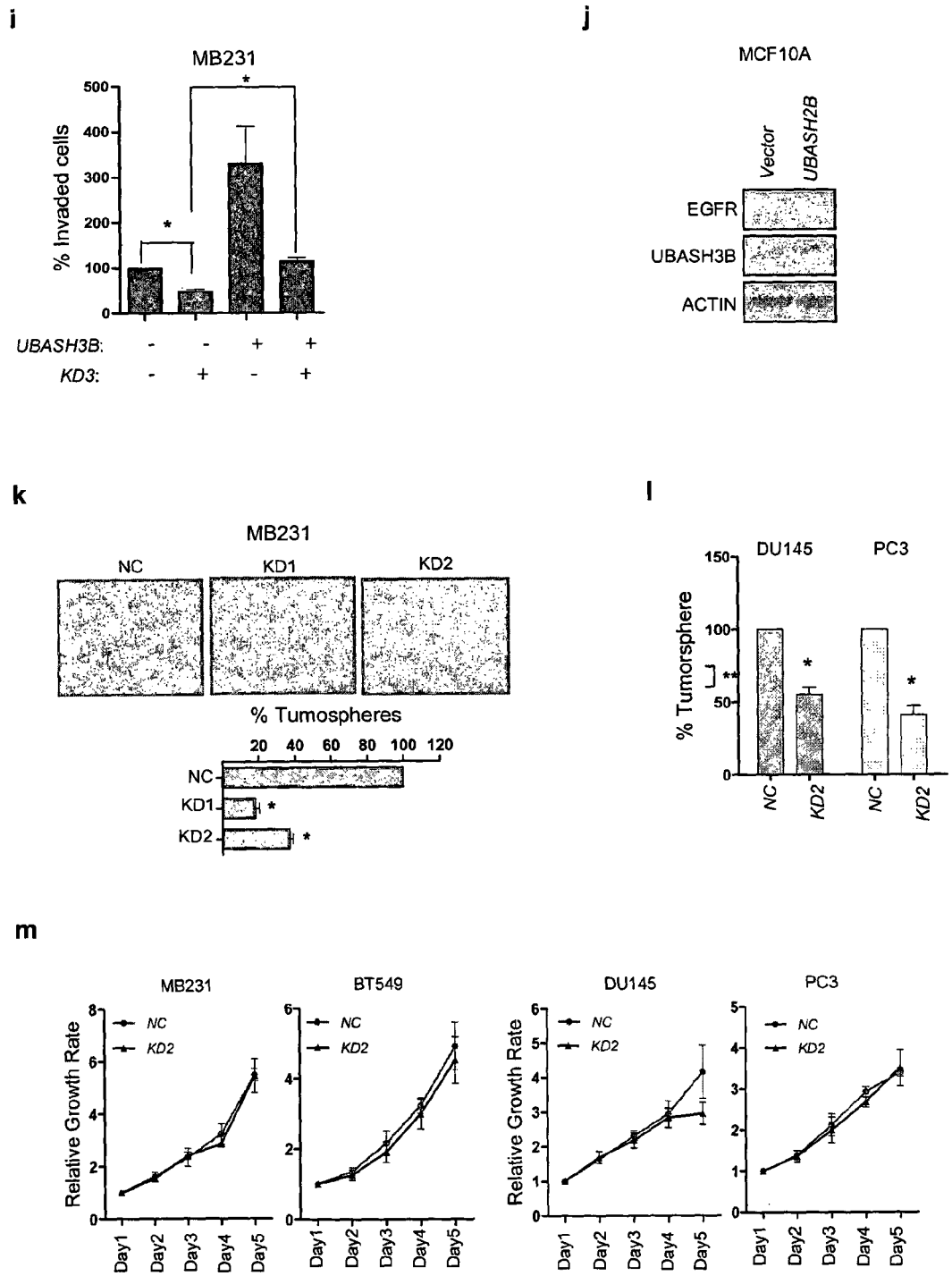

Figure 4 - cont'd
n
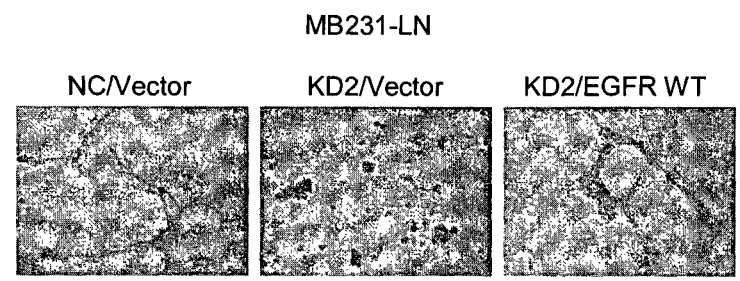
o
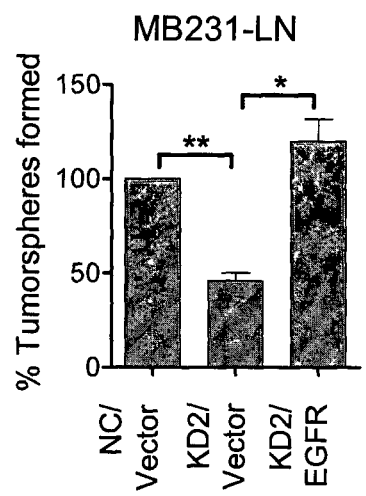

Figure 5 - cont'd
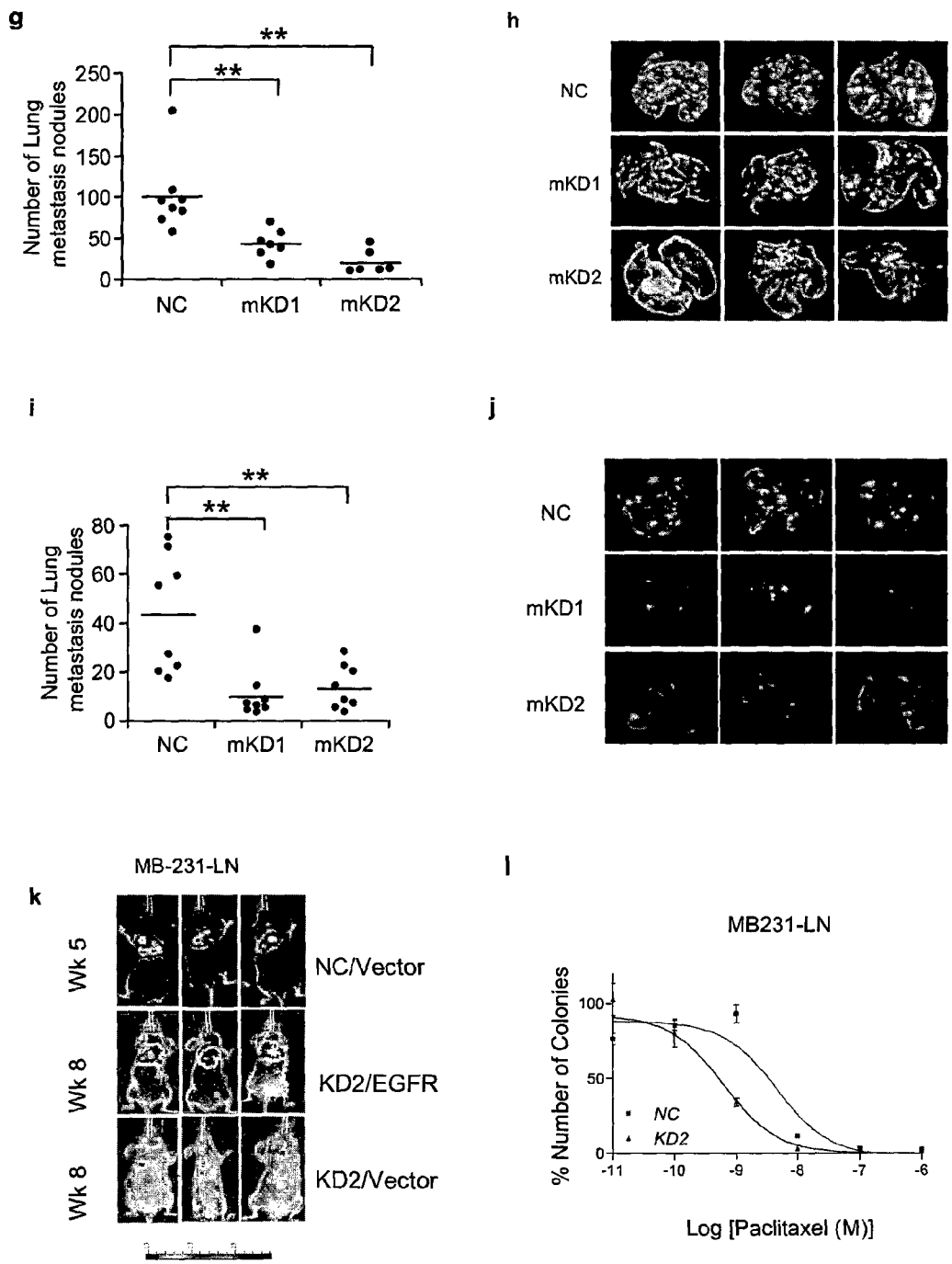

Figure 5 - cont'd
m
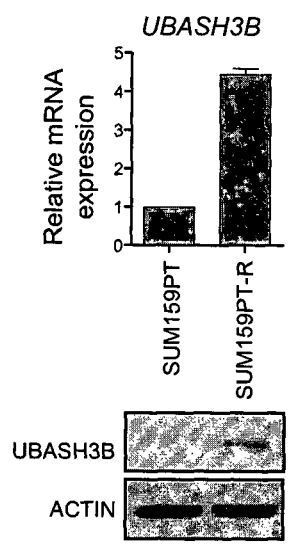
n
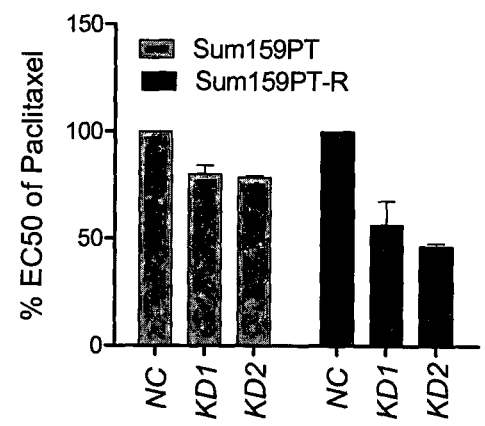

Figure 6 – cont'd
d
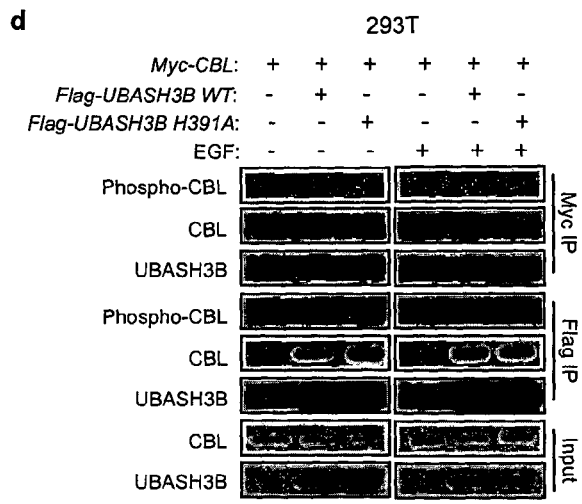
e
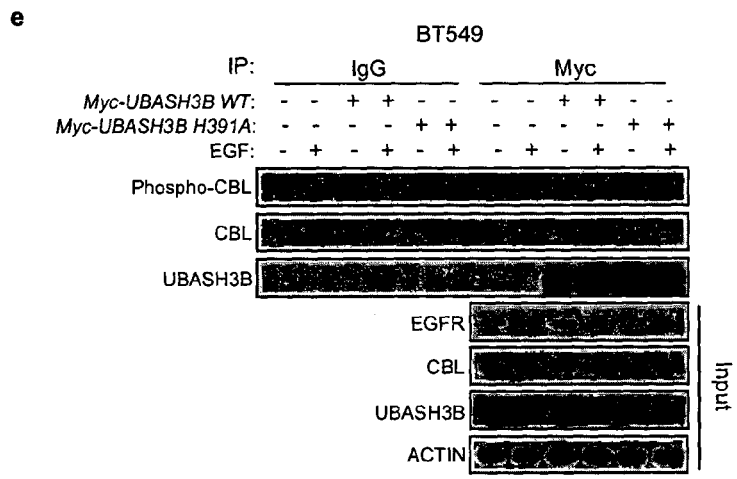
f
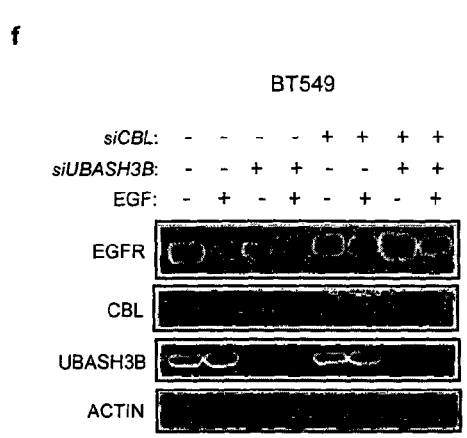
g
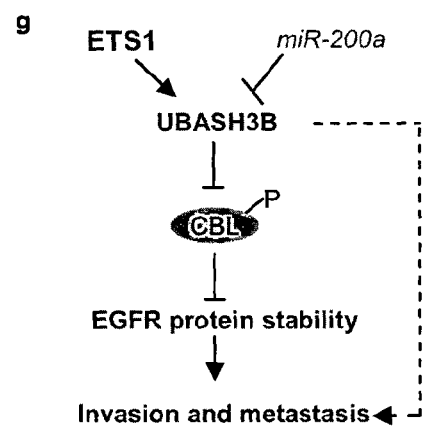

METHODS AND PHARMACEUTICAL COMPOSITIONS FOR TREATING CANCER

PRIORITY CLAIM TO RELATED APPLICATIONS

This application is a national stage application under 35 U.S.C. §371 of PCT/SG2012/000364, filed Sep. 28, 2012, and published as WO 2013/048345 on Apr. 4, 2013, which claims priority to Singapore Application No. 201107036-4, filed Sep. 28, 2011, which applications and publication are incorporated by reference as if reproduced herein and made a part hereof in their entirety, and the benefit of priority of each of which is claimed herein.

SEQUENCE LISTING

This document incorporates by reference herein an electronic sequence listing text file, which is filed in electronic format via EFS-Web. The text file is named "1364665.txt," is 12,288 bytes, and was created on Jul. 25, 2014.

TECHNICAL FIELD

The present invention generally relates to methods and pharmaceutical compositions for treating cancer. The present invention also relates to methods for determining suitability of a cancer patient for treatment using the disclosed methods and pharmaceutical compositions, and determining disease outcome.

BACKGROUND

Cancer is a leading cause of disease worldwide and according to a global study on cancer in 2008, an estimated 12.7 million new cancer cases occurred worldwide in that year alone. Of the various types of cancers, breast, lung, bowel and prostate cancers together account for over half of all new cancers worldwide. Accordingly, it is particularly important to develop new and more effective therapies against these particular types of cancer.

Breast cancers can be sub-divided into different subtypes based on whether the tumors express estrogen receptor (ER), progesterone receptor (PR) and human epidermal growth factor 2 (Her2). Amongst the various subtypes of breast cancer, Triple-Negative Breast Cancer (TNBC), which is named after its lack of expression of ER, PR and Her2, is one of the most aggressive subtypes of breast cancer with a high propensity for metastasis and is associated with an especially poor prognosis. Owing to the absence of above receptors, no effective targeted therapeutics against TNBC currently exist and current treatment modalities are limited to surgery, radiation and systemic chemotherapy. However, TNBC patients often experience early relapse due to distant tumor metastasis, though they may initially respond well to treatment. Therefore, continued efforts in identifying novel pathways or targets important for TNBC progression and therapy remain a high research priority.

Over the past few decades, tremendous effort has been spent searching for suitable molecular targeted therapies for TNBC, but with limited success. EGFR targeted therapy represents one such example. The rationale for targeting EGFR is based on the observation that TNBC often harbors, EGFR overexpression, leading to hyperactivation of multiple downstream oncogenic kinase signaling pathways such as AKT and ERK. However, EGFR inhibitors have thus far shown limited favorable response during clinical trials. A similar problem was found with poly-ADP ribose) polymerase (PARP) inhibitors which can induce synthetic lethality in BRCA1-deficient TNBC tumors and were thus once believed to be a promising targeted drug for TNBC during early stage clinical trials. However, such inhibitors subsequently failed in a late stage phase III trial.

Although the reasons for the ineffectiveness of these molecular targeted therapies has yet to be determined, one hypothesis is that breast tumors, in particular TNBCs, are highly heterogeneous and utilize multiple mechanisms to enable the aggressive phenotypes, such as invasion and metastasis. These pathways may then get integrated as specific signaling steps that collectively contribute to the disease progression. Pathways and mechanisms involved in invasion and metastasis often involve transcriptional reprogramming induced by deregulated transcriptional regulators, such as NF-κB, ETS1, Notch, TGF-β, and Polycomb protein EZH2, as well as microRNAs such as miR-200s. Downstream targets of these regulators may participate in various rate-limiting steps in disease progression, including epithelial to mesenchymal transition (EMT) (ZEB1/2, TWIST and CDH1), cancer stem cell self-renewal (IL-6 and STAT3), and distant metastasis (Sec23a and VCAM1). Although the breast cancer transcriptome has been extensively investigated, it remains unclear how these pathways are interconnected in disease progression and new regulatory elements crucial for the network integrity need to be identified.

There is a need to provide therapies for treating cancer that overcome, or at least ameliorate, one or more of the disadvantages described above.

There is a need to provide therapies to sensitize and/or re-sensitize a cancer patient who has become resistant to chemotherapy to chemotherapeutic treatment that overcome, or at least ameliorate, one or more of the disadvantages described above.

There is further a need to provide methods to facilitate selection of a suitable treatment for a cancer patient, optimizing the treatment regimen, and prognosis of disease outcome that overcome, or at least ameliorate, one or more of the disadvantages described above.

SUMMARY

According to a first aspect, there is provided a method of treating cancer by inhibiting expression of ubiquitin associated and SH3 domain containing B (UBASH3B) gene or by inhibiting the activity of UBASH3B protein or a functional variant thereof.

According to a second aspect, there is provided a method of sensitizing and/or re-sensitizing a cancer patient to a treatment with one or more chemotherapeutic agents, by inhibiting expression of UBASH3B gene or by inhibiting the activity of UBASH3B protein or a functional variant thereof.

According to a third aspect, there is provided an siRNA directed against the nucleic acid transcribed from the UBASH3B gene.

According to a fourth aspect, there is provided an siRNA directed against the nucleic acid transcribed from the ETS1 gene.

According to a fifth aspect, there is provided an shRNA directed against the nucleic acid transcribed from the UBASH3B gene.

According to a sixth aspect, there is provided a use of a UBASH3B antagonist in the manufacture of a medicament for treating cancer, wherein said UBASH3B antagonist is capable of inhibiting expression of UBASH3B gene or inhibiting the activity of UBASH3B protein or a functional variant thereof.

According to a seventh aspect, there is provided a use of a UBASH3B antagonist in the manufacture of a medicament for sensitizing and/or re-sensitizing a cancer patient to a treatment with one or more chemotherapeutic agents, wherein said UBASH3B antagonist is capable of inhibiting expression of UBASH3B gene or inhibiting the activity of UBASH3B protein or a functional variant thereof.

According to an eighth aspect, there is provided a method of determining cancer patient prognosis, comprising the steps of:

(a) determining the level of UBASH3B gene expression or UBASH3B protein activity in the patient's cancer, and (b) classifying the patient as having decreased survival if the patient's cancer has a higher level of UBASH3B gene expression or UBASH3B protein activity relative to the level of UBASH3B gene expression or UBASH3B protein activity in a non-invasive cancer.

According to a ninth aspect, there is provided a method of determining a cancer patient's susceptibility to treatment with an EGFR antagonist, wherein the method comprises the steps of:

(a) determining the level of UBASH3B gene expression or UBASH3B protein activity in the patient's cancer, and (b) classifying the patient as being susceptible to treatment with an EGFR antagonist if the patient's cancer has a higher level of UBASH3B gene expression or UBASH3B protein activity relative to the level of UBASH3B gene expression or UBASH3B protein activity in a non-invasive cancer.

According to a tenth aspect, there is provided a method of determining a cancer patient's susceptibility to a chemotherapeutic agent, wherein the method comprises the steps of:

(a) determining the level of UBASH3B gene expression or UBASH3B protein activity in the patient's cancer, and (b) classifying the patient as being susceptible to the chemotherapeutic agent if the patient's cancer has a lower level of UBASH3B gene expression or UBASH3B protein activity relative to the level of UBASH3B gene expression or UBASH3B protein activity in a non-invasive cancer.

According to an eleventh aspect, there is provided a pharmaceutical composition for preventing cancer invasion and/or metastasis, comprising a UBASH3B antagonist, and an agent selected from the group consisting of a CBL agonist, and a EGFR antagonist.

DEFINITIONS

The following words and terms used herein shall have the meaning indicated:

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DISCLOSURE OF OPTIONAL EMBODIMENTS

Exemplary, non-limiting embodiments of a method and composition for treating cancer will now be disclosed.

It has been found that modulation of the UBASH3B (also known as STS1 and used interchangeably herein) gene expression and/or the activity of UBASH3B protein results in modulation of CBL ubiquitin ligase dephosphorylation and activity, and EGFR gene expression and/or the activity of EGFR protein. Using gene array technology, it has been found that UBASH3B acts as a downstream target of invasive regulators ETS1 and miR-200a, and exerts its oncogenic effect through its phosphatase activity by dephosphorylation and inactivation of CBL ubiquitin ligase. By dephosphorylating and inactivating CBL ubiquitin ligase, UBASH3B has been found to upregulate gene expression and/or activity of EGFR protein, which is implicated in the malignant growth of a tumor, its invasion and/or metastasis. Thus, UBASH3B can be a therapeutic target in development of new therapies for cancer, particularly cancers which are associated with EGFR gene and/or protein expression such as TNBC, prostate cancer, lung cancer, brain cancer and colon cancer.

Thus, the present disclosure provides methods and pharmaceutical compositions for treating cancer using a compound capable of modulating expression of the UBASH3B gene, and/or the activity of the UBASH3B protein or a functional variant thereof.

The present disclosure also provides methods and pharmaceutical compositions for sensitizing and/or re-sensitizing a cancer patient to a treatment with one or more chemotherapeutic agents using a compound capable of modulating expression of the UBASH3B gene, and/or the activity of the UBASH3B protein or a functional variant thereof.

It has further been found that the expression of UBASH3B is positively correlated with the expression of ETS1 and EGFR, and negatively correlated with the expression of miR-200a and CBL. Thus, the present disclosure further provides methods to facilitate selection of a suitable treatment for a cancer patient, optimization of treatment regimen, and prognosis of disease outcome based on the expression level of UBASH3B.

Modulator Compounds

Disclosed herein are modulator compounds, such as UBASH3B antagonists, for treating a pathological condition, such as cancer, in a patient. Also disclosed are ETS1 antagonists, miR-200a agonists, CBL agonists and EGFR antagonists, any one or more which may be used in combination therapy with UBASH3B antagonists to treat a pathological condition, such as cancer, in a patient.

As used herein, the term "modulate" or grammatical variants thereof, refers to regulating, effecting or influencing in any way the expression of a gene (for example, the UBASH3B gene) and/or the activity of a protein (for example, the UBASH3B protein or a functional variant thereof). For example, modulation may cause an increase or a decrease in protein activity, binding characteristics, or any other biological, functional, or immunological properties of the protein. A modulator compound may be, for example, an agonist, antagonist or inhibitor of any one or more pathways or intermediate compounds in the pathways leading to the expression of the gene and/or activity of its protein. Modulator compounds may include synthetic agents or natural compounds, including but not limited to peptide, nucleic acid and non-proteinaceous organic molecules.

In one embodiment, the modulator compound is an UBASH3B antagonist. A "UBASH3B antagonist" (such as an "UBASH3B inhibitor") refers to a molecule (peptidyl or non-peptidyl) capable of neutralizing, blocking, inhibiting, abrogating or interfering with UBASH3B-associated activities including UBASH3B activation, its binding to one or more UBASH3B receptors, its tyrosine phosphatase activity, or its downstream molecular signaling (for example, CBL dephosphorylation), or decreasing, inhibiting or abrogating the gene expression or protein level of UBASH3B. The UBASH3B antagonist may reduce or inhibit, by at least 10%, 20%, 30%, 40%, 50%, 60%, 70%, 80%, 90% or more, the expression level or biological activity of UBASH3B.

In one embodiment, the modulator compound is an inhibitor of the tyrosine phosphatase activity of the UBASH3B protein or a functional variant thereof. In one embodiment, the inhibitor of the tyrosine phosphatase activity is an agent capable of mutating the wild-type UBASH3B such that the tyrosine phosphatase activity is reduced or lost. Such mutants may be prepared using methods known in the art, for example using site-directed mutagenesis.

UBASH3B antagonists useful in the disclosed methods include peptidyl or non-peptidyl compounds that specifically bind UBASH3B, such as oligonucleotides, antibodies, inorganic molecules, ribozymes that target UBASH3B, and UBASH3B aptamers.

Exemplary oligonucleotides that can act as UBASH3B antagonists include, but are not limited to, interfering ribonucleic acid (such as siRNA, shRNA and miRNA), protein nucleic acids (PNAs), and locked nucleic acids (LNAs).

As used herein, the term "siRNA" refers to a ribonucleic acid (RNA) or RNA analog comprising between about 10 to 50 nucleotides (or nucleotide analogs) capable of directing or mediating the RNA interference pathway. These molecules can vary in length and can contain varying degrees of complementarity to their target messenger RNA (mRNA) in the antisense strand. The term "siRNA" includes duplexes of two separate strands, i.e. double stranded RNA, as well as single strands that can form hairpin structures comprising a duplex region. The siRNA may have a length of between about 10 to 50 nucleotides, or between about 15 to 50 nucleotides, or between about 20 to 50 nucleotides, or between about 25 to 50 nucleotides, or between about 30 to 50 nucleotides, or between about 35 to 50 nucleotides, or between about 40 to 50 nucleotides, or between about 10 to 45 nucleotides, or between about 10 to 40 nucleotides, or between about 10 to 35 nucleotides, or between about 10 to 30 nucleotides, or between about 10 to 25 nucleotides, or between about 10 to 20 nucleotides, or between about 15 to 50 nucleotides, or between about 15 to 35 nucleotides, or between about 15 to 30 nucleotides, or between about 15 to 25 nucleotides. In one embodiment, the siRNA has a length of between 15 to 30 nucleotides.

The application of siRNA to down-regulate the activity of its target mRNA is known in the art. mRNA degradation may occur when the anti-sense strand, or guide strand, of the siRNA directs the RNA-induced silencing complex (RISC) to cleave its target mRNA bearing a complementary sequence. Accordingly, the siRNA may be complementary to any portion of varying lengths on the UBASH3B gene. The siRNA may also be complementary to the sense strand and/or the anti-sense strand of the UBASH3B gene. Accordingly, in one embodiment, siRNA treatment may be used to silence the UBASH3Bgene, thereby depleting the UBASH3B protein downstream.

The siRNA may be directed against fragments of the nucleic acid transcribed from the gene. Accordingly, in one embodiment, the siRNA may comprise a sequence that is complementary to any fragment of the gene (such as the UBASH3B gene) or functional variants thereof. Such functional variants thereof may comprise at least one modified or substituted nucleotide. Functional modifications and/or substitutions of the siRNA may be performed by methods known in the art.

In one embodiment, the siRNA used as UBASH3B antagonist comprises a sequence selected from the group consisting of: 5'-CCGGCUUAUUUGAGUGGAC-3' (SEQ ID NO: 1), 5'-CCUCAUAAGAAGCAGCUAC-3' (SEQ ID NO: 2), and 5'-GCACUGCAACUGAGAAAUU-3' (SEQ ID NO: 3), or functional variants thereof. In one embodiment, the siRNA is 5'-CCGGCUUAUUUGAGUGGAC-3' (SEQ ID NO: 1), or functional variants thereof. In one embodiment, the siRNA is 5'-CCUCAUAAGAAGCAGCUAC-3' (SEQ ID NO: 2), or functional variants thereof. In one embodiment, the siRNA is 5'-GCACUGCAACUGAGAAAUU-3' (SEQ ID NO: 3), or functional variants thereof.

The term "shRNA", as used herein, refers to a unimolecular RNA that is capable of performing RNA interference (RNAi) and that has a passenger strand, a loop and a guide strand. The passenger and guide strand may be substantially complementary to each other. The term "shRNA" may also include nucleic acids that contain moieties other than ribonucleotide moieties, including, but not limited to, modified nucleotides, modified internucleotide linkages, non-nucleotides, deoxynucleotides, and analogs of the nucleotides mentioned thereof. In one embodiment, the shRNA used as UBASH3B antagonist comprises a sequence selected from the group consisting of: 5'-GCTCAGAATCATTTAG-CATAT-3' (SEQ ID NO: 41), and 5'-GCGTTCAGACTGCA-CATAATA-3' (SEQ ID NO: 42), or functional variants thereof. In one embodiment, the shRNA is 5'-GCTCAGAAT-CATTTAGCATAT-3' (SEQ ID NO: 41), or functional variants thereof. In another embodiment, the shRNA is 5'-GCGT-TCAGACTGCACATAATA-3' (SEQ ID NO: 42), or functional variants thereof.

miRNAs down-regulate their target mRNAs. The term "miRNA" generally refers to a single stranded molecule, but in some embodiments, may also encompass a region or an additional strand that is partially (between 10% and 50% complementary across the length of strand), substantially (greater than 50% but less than 100% complementary across the length of strand) or fully complementary to another region of the same single-stranded molecule or to another nucleic acid. Thus, nucleic acids may encompass a molecule that comprises one or more complementary or self-complementary strand(s) or "complements" of a particular sequence comprising a molecule. For example, precursor miRNA may have a self-complementary region, which is up to 100% complementary. miRNA probes or oligonucleotides of the invention can include, can be or can be at least 60%, 65%, 70%, 75%, 80%, 85%, 90%, 95%, 96%, 97%, 98%, 99% or 100% complementary to their target.

In one embodiment, the UBASH3B antagonist is an antibody (for example, an anti-UBASH3B antibody) or an antigen-binding fragment thereof. An "anti-UBASH3B antibody" is an antibody that binds to UBASH3B with sufficient affinity and specificity. For example, the antibody may bind UBASH3B with a $K_a$ value of between about 100 nM to 1 pM. Antibody affinities may for example be determined using methods known in the art, for example by a surface plasmon resonance based assay (such as the BIAcore assay); an enzyme-linked immunoabsorbent assay (ELISA); and, competition assays (for example, radioimmunoassays). An anti-UBASH3B antibody will usually not bind to other UBASH3B homologues, nor other members of of its family such as UBASH3A (also known as STS2), nor other tyrosine phosphatases.

The term "antibody" includes monoclonal antibodies, polyclonal antibodies, multispecific antibodies (for example, bispecific antibodies), monovalent antibodies, multivalent antibodies, and antibody fragments so long as they exhibit the desired biological activity. "Antibody fragments" may comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

The antibody may also be a "blocking" antibody or an antibody "antagonist" which inhibits or reduces biological activity of the antigen it binds. In some embodiments, blocking antibodies or antagonist antibodies completely inhibit the biological activity of the antigen.

An "antibody variant" as used herein refers to an amino acid sequence variant of the species-dependent antibody wherein one or more of the amino acid residues of the species-dependent antibody have been modified. Such variants necessarily have less than 100% sequence identity or similarity with the species-dependent antibody. In one embodiment, the antibody variant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e. same residue) or similar (i.e. amino acid residue from the same group based on common side-chain properties) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

In one embodiment, the modulator compound is an ETS1 antagonist. A "ETS1 antagonist" (such as an "ETS1 inhibitor") refers to a molecule (peptidyl or non-peptidyl) capable of neutralizing, blocking, inhibiting, abrogating, reducing, or interfering with ETS1 expression and/or its activities including its binding to one or more ETS1 receptors, its transcription activity, or its upregulation of UBASH3B gene expression or protein activity. The ETS1 antagonist may reduce or inhibit, by at least 10%, 20%, 30%, 40%, 50%, 60%, 70%, 80%, 90% or more, the expression level or biological activity of ETS1. ETS1 antagonists useful in the disclosed methods include peptidyl or non-peptidyl compounds that specifically bind ETS1, such as oligonucleotides, antibodies, and inorganic molecules. Exemplary oligonucleotides that can be used as ETS1 antagonists include, but are not limited to, interfering ribonucleic acid (such as siRNA, shRNA and miRNA), protein nucleic acids (PNAs), and locked nucleic acids (LNAs). The siRNA that can be used as ETS1 antagonist may have a length of between about 10 to 50 nucleotides, or between about 15 to 50 nucleotides, or between about 20 to 50 nucleotides, or between about 25 to 50 nucleotides, or between about 30 to 50 nucleotides, or between about 35 to 50 nucleotides, or between about 40 to 50 nucleotides, or between about 10 to 45 nucleotides, or between about 10 to 40 nucleotides, or between about 10 to 35 nucleotides, or between about 10 to 30 nucleotides, or between about 10 to 25 nucleotides, or between about 10 to 20 nucleotides, or between about 15 to 50 nucleotides, or between about 15 to 35 nucleotides, or between about 15 to 30 nucleotides, or between about 15 to 25 nucleotides. In one embodiment, the siRNA has a length of between 15 to 30 nucleotides. In one embodiment, the siRNA used as ETS1 antagonist comprises a sequence selected from the group consisting of: 5'-CCCAGCCUAUCCAGAAUCC-3' (SEQ ID NO: 4) and 5'-GGAAUUACUCACUGAUAAA-3' (SEQ ID NO: 5), or functional variants thereof. In one embodiment, the siRNA used as ETS1 antagonist comprises 5'-CCCAGCCUAUC-CAGAAUCC-3' (SEQ ID NO: 4), or functional variants thereof. In another embodiment, the siRNA used as ETS1 antagonist comprises 5'-GGAAUUACUCACUGAUAAA-3' (SEQ ID NO: 5), or functional variants thereof.

In one embodiment, the ETS1 antagonist is an inorganic molecule. An exemplary inorganic molecule that may be used as ETS1 antagonist is U0126.

In one embodiment, the modulator compound is an miR-200a agonist. A "miR-200a agonist" refers to a molecule which intensifies or mimics the biological activity of miR-200a, such as targeting and inhibiting UBASH3B. miR-200a agonists may include proteins, nucleic acids, carbohydrates, small molecules, or any other compound or composition which modulates the activity of miR-200a either by directly interacting with miR-200a or by acting on components of the biological pathway in which miR-200a participates. Exemplary miR-200a agonists include miR-200a mimics.

In one embodiment, the modulator compound is CBL agonist. A "CBL agonist" refers to a molecule which intensifies or mimics the biological activity of CBL. CBL agonists may include proteins, nucleic acids, carbohydrates, small molecules, or any other compound or composition which modulates the activity of CBL (for example, inactivation of EGFR) either by directly interacting with CBL or by acting on components of the biological pathway in which CBL participates. Exemplary CBL agonists include CBL mimics.

In one embodiment, the modulator compound is an EGFR antagonist. An "EGFR antagonist" (such as an "EGFR inhibitor") refers to a molecule (peptidyl or non-peptidyl) capable of neutralizing, blocking, inhibiting, abrogating or interfering with EGFR-associated activities such as its activation, signaling and its protein-tyrosine kinase activity, or abrogating the gene expression or protein level of EGFR. The EGFR antagonist may reduce or inhibit, by at least 10%, 20%, 30%, 40%, 50%, 60%, 70%, 80%, 90% or more, the expression level or biological activity of EGFR. EGFR antagonists useful in the disclosed methods include peptidyl or non-peptidyl compounds that specifically bind EGFR, such as oligonucleotides, antibodies, and inorganic molecules. Exemplary oligonucleotides that can be used as EGFR antagonists include, but are not limited to, interfering ribonucleic acid (such as siRNA, shRNA and miRNA), protein nucleic acids (PNAs), and locked nucleic acids (LNAs). The siRNA that can be used as EGFR antagonist may have a length of between about 10 to 50 nucleotides, or between about 15 to 50 nucleotides, or between about 20 to 50 nucleotides, or between about 25 to 50 nucleotides, or between about 30 to 50 nucleotides, or between about 35 to 50 nucleotides, or between about 40 to 50 nucleotides, or between about 10 to 45 nucleotides, or between about 10 to 40 nucleotides, or between about 10 to 35 nucleotides, or between about 10 to 30 nucleotides, or between about 10 to 25 nucleotides, or between about 10 to 20 nucleotides, or between about 15 to 50 nucleotides, or between about 15 to 35 nucleotides, or between about 15 to 30 nucleotides, or between about 15 to 25 nucleotides. In one embodiment, the siRNA has a length of between 15 to 30 nucleotides.

In one embodiment, the EGFR antagonist is an antibody or small molecule which binds to EGFR. In one embodiment, the EGFR antagonist is an EGFR-targeted drug. In one embodiment, an EGFR antagonist has a binding affinity (dissociation constant) to EGFR of about 1,000 nM or less, of about 100 nM or less, or about 50 nM or less. In one embodiment, an EGFR antagonist inhibits EGFR signaling with an $IC_{50}$ of about 1,000 nM or less, of about 500 nM or less, or of about 50 nM or less. In some embodiments, the EGFR antagonist reduces or inhibits, by at least 10%, 20%, 30%, 40%, 50%, 60%, 70%, 80%, 90% or more, the expression level or biological activity of EGFR.

As used herein, the term "EGFR-targeted drug" refers to a therapeutic agent that binds to EGFR and reduces or inhibits EGFR activation. Examples of such agents include antibodies (such as Cetuximab, Matuzumab, and the like) and small molecules that bind to EGFR (such as Erlotinib, Gefitinib, CI-1033, GW-2016, Iressa (ZD-1839), Tarceva (OSI-774), PKI-166, EKB-569, HKI-272, and the like).

Two or more of the disclosed modulator compounds may be administered in a combination therapy, optionally together with one or more chemotherapeutic agents. The two or more disclosed modulator compounds, and optionally one or more chemotherapeutic agents, may be administered concurrently, or sequentially in any order, in the same or separate formulation. "Concurrent" administration refers to administration of two or more modulator compounds, and optionally one or more chemotherapeutic agents, where at least part of the administration overlaps in time. Accordingly, concurrent administration includes a dosing regimen when the administration of one or more compound(s) continues after discontinuing the administration of one or more other compound(s). "Sequential" administration refers to administration of two or more modulator compounds and optionally one or more chemotherapeutic agents, wherein a first compound or agent can occur prior to, and/or following, administration of a second compound or agent.

Combinations of the disclosed modulator compounds may be synergistic. Hence, the disclosed modulator compounds may be used alone, or in combination with one or more other disclosed modulator compounds, or optionally in combination with one or more chemotherapeutic agents as part of a specific treatment regimen intended to provide a beneficial effect from the combined activity of these compounds. The beneficial effect of the combination includes, but is not limited to, pharmacokinetic or pharmacodynamic co-action resulting from the combination of modulator compounds and optionally, chemotherapeutic agents.

As used herein, the term "anti-cancer therapy" refers to therapy useful in treating cancer, that may be used alone or in combination with other treatments. Examples of anti-cancer therapeutic agents include, but are not limited to, chemotherapeutic agents, growth inhibitory agents, cytotoxic agents, agents used in radiation therapy, anti-angiogenesis agents, apoptotic agents, and the like. Examples of chemotherapeutic agents include but are not limited to Abraxane, Amsacrine, Azacitidine, Bendamustine, Bleomycin, Busulfan, Cabazitaxel, Capecitabine, Carboplatin, Carmustine, Chlorambucil, Cisplatin, Cladribine, Clofarabine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Hydroxycarbamide, Idarubicin, Ifosfamide, Irinotecan, Leucovorin, Lomustine, Melphalan, Mercaptopurine, Mesna, Methotrexate, Mitomycin, Mitotane, Mitoxantrone, Oxaliplatin, Paclitaxel, Pemetrexed, Pentostatin, Procarbazine, Raltitrexed, Rasburicase, Satraplatin, Streptozocin, Tegafururacil, Temozolomide, Thiotepa, Tioguanine, Topotecan, Trabectedin, Treosulfan, Vinblastine, Vincristine, Vindesine, and Vinorelbine. Combinations thereof may also be used.

In one embodiment, the chemotherapeutic agent is selected from the group consisting of Paclitaxel, Docetaxel, Gemcitabine, Capecitabine and Vinorelbine.

Hence, in one embodiment, there is provided a pharmaceutical composition comprising a UBASH3B antagonist and a ETS1 antagonist. In one embodiment, there is provided a pharmaceutical composition comprising a UBASH3B antagonist and a miR-200a agonist. In one embodiment, there is provided a pharmaceutical composition comprising a UBASH3B antagonist and a CBL agonist. In one embodiment, there is provided a pharmaceutical composition comprising a UBASH3B antagonist and a EGFR antagonist. In one embodiment, there is provided a pharmaceutical composition comprising a UBASH3B antagonist, a ETS1 antagonist, and a miR-200a agonist. In one embodiment, there is provided a pharmaceutical composition comprising a UBASH3B antagonist, a ETS1 antagonist, a miR-200a agonist, and a CBL agonist. In one embodiment, there is provided a pharmaceutical composition comprising a UBASH3B antagonist, a ETS1 antagonist, a miR-200a agonist, and an EGFR antagonist. In one embodiment, there is provided a pharmaceutical composition comprising a UBASH3B antagonist, a ETS1 antagonist, a miR-200a agonist, a CBL agonist, and an EGFR antagonist.

In another embodiment, the disclosed composition comprises one or more modulator compounds selected from the group consisting of a UBASH3B antagonist, a ETS1 antagonist, a miR-200a agonist, a CBL agonist, and a EFGR antagonist, and a chemotherapeutic agent. In one embodiment, the chemotherapeutic agent is Paclitaxel.

The disclosed pharmaceutical compositions may comprise one or more pharmaceutically acceptable carriers or excipients, in the form of lyophilized formulations or aqueous solutions. Pharmaceutically acceptable carriers or excipients are generally nontoxic to recipients at the dosages and concentrations employed. Typically, the carrier(s) or excipient(s) will form from 10% to 99.9% by weight of the compositions.

The term "excipient" refers to a pharmaceutically acceptable additive, other than the active ingredient, included in a formulation and having different purposes depending, for example, on the nature of the drug, and the mode of administration. Examples of excipients include, but are not limited to, carriers; co-solvents, stabilizing agents, solubilizing agents and surfactants, buffers, antioxidants, tonicity agents, bulking agents, lubricating agents, emulsifiers, suspending or viscosity agents, antibacterial agents, chelating agents, preservatives, sweeteners, perfuming agents, flavoring agents, administration aids, and combinations thereof. Some of the excipients or additives may have more than one possible function or use, depending on their properties and the nature of the formulation. Such excipients are generally formulated according to a number of factors well within the purview of those of ordinary skill in the art.

As used herein, the term "pharmaceutically acceptable carrier" refers to media generally accepted in the art for the delivery of biologically active agents, i.e. the disclosed modulator compound alone or in combination with any of the other disclosed modulator compounds or anti-cancer therapeutic agents, to mammals, for example humans. Such carriers are generally formulated according to a number of factors well within the purview of those of ordinary skill in the art. These include, without limitation, the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, for example, for stabilization of the active agent, well known to those of ordinary skill in the art. Non-limiting examples of pharmaceutically acceptable carriers are hyaluronic acid and salts thereof, and microspheres (including, but not limited to, poly(D,L)-lactide-co-glycolic acid copolymer (PLGA), poly(L-lactic acid) (PLA), poly(caprolactone) (PCL) and bovine serum albumin (BSA)).

The disclosed modulator compounds may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, for example as disclosed in Remington's Pharmaceutical Sciences 16th edition, Osol, A. Ed. (1980).

Sustained-release preparations may also be prepared. Suitable examples of sustained-release preparations include semi-permeable matrices of solid hydrophobic polymers containing the modulator compound, which matrices are in the form of shaped articles, for example films, or microcapsules.

The formulations to be used for in vivo administration are generally sterile. Sterility may be readily accomplished using methods known in the art, such as filtration through sterile filtration membranes.

Therapeutic Uses

The disclosed modulator compounds may be used in the methods as disclosed herein for the treatment of cancer. The modulator compounds may be used alone, or in combination with one or more other modulator compounds, or in combination with one or more anti-cancer agents, such as chemotherapeutic agents.

Thus, in one aspect, there is provided a method of treating cancer by modulating expression of the UBASH3B gene, or the activity of the UBASH3B protein or a functional variant thereof. In one embodiment, the method comprises inhibiting expression of the UBASH3B gene, or the activity of the UBASH3B protein or a functional variant thereof. In one embodiment, the method comprises inhibiting expression of the UBASH3B gene, or the activity of the UBASH3B protein or a functional variant thereof by administering a UBASH3B antagonist, such as a UBASH3B inhibitor.

In another aspect, there is provided a method of sensitizing and/or re-sensitizing a cancer patient to a treatment with one or more chemotherapeutic agents by modulating expression of the UBASH3B gene, or the activity of the UBASH3B protein or a functional variant thereof. In one embodiment, the method comprises inhibiting expression of the UBASH3B gene, or the activity of the UBASH3B protein or a functional variant thereof. In one embodiment, the method comprises inhibiting expression of the UBASH3B gene, or the activity of the UBASH3B protein or a functional variant thereof by administering a UBASH3B antagonist, such as a UBASH3B inhibitor.

In some embodiments, there is provided a use of the disclosed pharmaceutical composition and/or one or more disclosed modulator compounds (e.g. the disclosed UBASH3B antagonist, ETS1 antagonist, miR200a agonist, CBL agonist, or EGFR antagonist) in the manufacture of a medicament for treating cancer, and/or for sensitizing and/or re-sensitizing, a cancer patient to a treatment with one or more anti-cancer agents, such as chemotherapeutic agents.

The term "expression" as used herein refers interchangeably to expression of a gene or gene product, including the encoded protein. "Expression" of a gene may refer to transcription into a polynucleotide, translation into a protein, or even post-translational modification of the protein.

The term "inhibit" or grammatical variants thereof, refer to the ability to cause an overall decrease of 20%, 30%, 40%, 50%, 60%, 70%, 75%, 80%, 85%, 90%, 95%, or greater. "Inhibit" can refer to the symptoms of the disorder being treated, the presence or size of the tumor metastases, or the size of the primary tumor. For example, the expression of UBASH3B gene or the activity of the UBASH3B protein or a functional variant thereof may be inhibited by administering a UBASH3B antagonist, a ETS1 antagonist, and/or a miR-200a agonist.

In one embodiment, the cancer is of an invasive and/or metastatic phenotype. Hence, in one embodiment, the treatment method comprises preventing cancer invasion and/or metastasis.

By "cancer invasion" is meant the cancer cells breaking into the surrounding tissue and expanding the lesion. An invasive form of cancer may also be known as a basal-type cancer, for example, a basal-type breast cancer or ovarian cancer. A non-invasive form of cancer may also be known as a luminal-type cancer, for example a non-TNBC.

By "metastasis" is meant the spread of cancer from its primary site to other parts in the body. Cancer cells can break away from a primary tumor, penetrate into lymphatic and blood vessels, circulate through, the bloodstream, stop at a distant site in normal tissues elsewhere in the body and grow to form a life-threatening mass at the new site. By "primary tumor" or "primary cancer" is meant the original cancer and not a metastatic lesion located in another tissue, organ, or location in the subject's body. Metastasis can be local or distant.

"Treatment" includes any and all uses which remedy a disease state or symptoms, prevent the establishment of disease, or otherwise prevent, hinder, retard, or reverse the progression of disease or other undesirable symptoms in any way whatsoever. Hence, "treatment" includes prophylactic and therapeutic treatment. Those in need of treatment include those already having a benign, pre-cancerous, or non-metastatic tumor as well as those in which the occurrence or recurrence of cancer is to be prevented. Those in need of treatment also includes those who have previously been treated with one or more anti-cancer therapy, such as chemotherapy.

As used herein, the term "sensitizing" refers to a process of rendering a subject receptive to a treatment. "Re-sensitizing" refers to a process of restoring responsiveness to a treatment in a subject who was receptive to a treatment but who is no longer receptive to a treatment due to the fact that the patient or the tumor cells of the patient developed a resistance against the anti-cancer therapy used for treating the cancer.

The terms "cancer" and "cancerous" refer to or describe the physiological condition that is typically characterized by unregulated cell growth. The cancer may be benign and/or malignant. An "early stage cancer" or "early stage tumor" for example, refers to a cancer that is not invasive or metastatic or is classified as a Stage 0, I, or II cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include breast cancer (including invasive or metastatic breast cancer, such as TNBC), prostate cancer (including invasive or metastatic prostate cancer), lung cancer (including small-cell lung cancer (SCLC), non-small cell lung cancer (NSCLC), adenocarcinoma of the lung and squamous carcinoma of the lung), colorectal cancer, brain cancer, kidney or renal cancer, pancreatic cancer, gastric carcinoma, bladder cancer, esophageal cancer, mesothelioma, melanoma, thyroid cancer, head and neck cancer, osteosarcoma, glioblastoma, squamous cell cancer (such as epithelial squamous cell cancer), cancer of the peritoneum, hepatocellular cancer, gastric or stomach cancer (including gastrointestinal cancer), cervical cancer, ovarian cancer, liver cancer, hepatoma, rectal cancer, endometrial or uterine carcinoma, salivary gland carcinoma, vulval cancer, hepatic carcinoma, anal carcinoma, penile carcinoma, testicular cancer, as well as tumors of the biliary tract. In one embodiment, the cancer is metastatic triple-negative breast cancer (TNBC), including any histologically confirmed triple-negative (ER-, PR-, Her2-) adenocarcinoma of the breast with locally recurrent or metastatic disease, for example, where the locally recurrent disease is not amenable to resection with curative intent. In another embodiment, the cancer is invasive prostate cancer. In yet another embodiment, the cancer is invasive colon cancer.

The term "subject" includes human or other mammal and includes any individual it is desired to examine or treat using the disclosed methods. Patients are also included herein. However, it will be understood that "patient" does not imply that symptoms are present. Suitable mammals include, but are not restricted to, primates, livestock animals (e.g. sheep, cows, horses, donkeys, pigs), laboratory test animals (e.g. rabbits, mice, rats, guinea pigs, hamsters), companion animals (e.g. cats, dogs) and captive wild animals (e.g. foxes, deer, dingoes). Preferably, the mammal is human.

In one embodiment, there is provided a method of treating cancer, and/or sensitizing and/or re-sensitizing a cancer patient to a treatment with one or more chemotherapeutic agents, by administering a modulator compound that inhibits expression of the UBASH3B gene, or the activity of the UBASH3B protein or a functional variant thereof.

The modulator compound, or a pharmaceutical composition thereof, may be administered by any suitable means, such as by oral, parenteral (including intramuscular, intravenous, intraarterial, intraperitoneal, and subcutaneous), transdermal, intrapulmonary, or intranasal administration. The modulator compound, or a pharmaceutical composition thereof, may be administered according to various dosing schedules known to those skilled in the art including but not limited to single or multiple administrations over various time-points, bolus administration, and pulse infusion.

The modulator compound, or a pharmaceutical composition thereof, may be administered in a therapeutically effective amount. The term "therapeutically effective amount" refers to an amount of a modulator compound to treat or prevent a disease or disorder in a mammal, or to provide the desired therapeutic effect. In the case of cancers, the therapeutically effective amount of the modulator compound may reduce the number of cancer cells; reduce the primary tumor size; inhibit (i.e. slow to some extent and preferably stop) cancer cell infiltration into peripheral organs; inhibit (i.e. slow to some extent and preferably stop) tumor metastasis; inhibit, to some extent, tumor growth; and/or relieve to some extent one or more of the symptoms associated with the disorder.

The exact amount required will vary from subject to subject depending on factors such as the species being treated, the age and general condition of the subject, the severity of the condition being treated, the particular agent being administered, the mode of administration, the scheduling of administration, and other factors known to medical practitioners. Thus, it is not possible to specify an exact "effective amount". However, for any given case, an appropriate "effective amount" may be determined by one of ordinary skill in the art using routine experimentation.

Depending on the type and severity of the disease, about 1 µg/kg to 500 mg/kg (for example, 0.1-20 mg/kg) of a modulator compound as disclosed herein may be administered to the patient, for example, by one or more separate administrations, or by continuous infusion. A typical daily dosage might range from about 1 µg/kg to about 500 mg/kg or more, depending on the factors discussed above. For example, about 1 mg/kg to 500 mg/kg, about 1 mg/kg to 400 mg/kg, about 1 mg/kg to 300 mg/kg, about 1 mg/kg to 200 mg/kg, about 1 mg/kg to 100 mg/kg, about 1 mg/kg to 50 mg/kg, about 100 mg/kg to 500 mg/kg, about 100 mg/kg to 400 mg/kg, about 100 mg/kg to 300 mg/kg, about 100 mg/kg to 200 mg/kg, about 200 mg/kg to 500 mg/kg, about 200 mg/kg to 400 mg/kg, or about 200 mg/kg to 300 mg/kg, of an EGFR antagonist (such as Erlotinib) may be administered. In one embodiment, about 1 mg/kg, about 10 mg/kg, about 100 mg/kg, about 200 mg/kg, about 300 mg/kg, about 400 mg/kg, about 500 mg/kg, or more of an EGFR antagonist (such as Erlotinib) is administered. In one embodiment, less than about 1 µg/kg of an EGFR antagonist (such as Erlotinib) is administered. In one embodiment, about 1 nM to about 100 nM, about 5 nM to about 90 nM, about 10 nM to about 80 nM, about 15 nM to about 70 nM, about 30 nM to about 60 nM, or more of an UBASH3B antagonist or ETS1 antagonist may be administered. In one embodiment, about 5 nM, about 10 nM, about 20 nM, about 30 nM, about 40 nM, about 50 nM, about 60 nM, about 70 nM, about 80 nM, about 90 nM, or about 100 nM of an UBASH3B antagonist or ETS1 antagonist may be administered.

For repeated administrations over several days or longer, depending on the condition, the treatment may be sustained until the cancer is treated, as measured by the methods described herein or known in the art. Other dosage regimens that may be useful are also contemplated herein. For example, the modulator compound may be administered once every week, every two weeks, or every three weeks, at a dosage range as disclosed. The progress of the therapy using the disclosed methods may be monitored by conventional techniques and assays, as well as the methods described herein.

The duration of therapy may continue for as long as medically indicated or until a desired therapeutic effect is achieved. One or more maintenance doses may also be administered to reduce the likelihood of disease recurrence or progression. A "maintenance" dose refers to one or more doses of a therapeutic agent (such as one or more of the disclosed modulator compounds) administered to the patient over or after a treatment period. The maintenance doses may be administered at spaced treatment intervals, such as approximately every week, approximately every 2 weeks, approximately every 3 weeks, or approximately every 4 weeks, and may be provided for any length of time, including extended time periods up to the life-span of the subject. Maintenance therapy may be provided after initial therapy or in conjunction with initial or additional therapies.

Advantageously, the disclosed methods are capable of producing anti-cancer effects in a human patient without causing significant toxicities or adverse effects, so that the patient benefited from the treatment overall. The efficacy of the disclosed treatment methods can be measured by various endpoints commonly used in evaluating cancer treatments, including but not limited to, duration of survival, tumor regression, tumor weight or size shrinkage, time to progression, progression free survival, overall response rate, duration of response, and quality of life, as discussed below. The disclosed modulator compounds and compositions thereof may cause inhibition of metastatic spread without shrinkage of the primary tumor, or may simply exert a tumouristatic effect.

"Survival" refers to the patient remaining alive, and may refer to overall survival (OS), progression free survival (PFS), both. "Overall survival" (OS) refers to the patient remaining alive for a defined period of time, such as 1 year, 5 years, etc from the time of diagnosis or treatment. "Progression free survival" (PFS) refers to the patient remaining alive, without the cancer progressing or getting worse. By "extending survival" is meant increasing overall or progression free survival, for example in a treated patient relative to an untreated patient (i.e. relative to a patient not treated with a disclosed modulator compound or pharmaceutical composition thereof), and/or relative to a control treatment protocol, such as treatment only with a chemotherapeutic agent, such as those used in the treatment for breast cancer. Survival is monitored for at least about one month, two months, four months, six months, nine months, or at least about 1 year, or at least about 2 years, or at least about 3 years, or at least about 4 years, or at least about 5 years, or at least about 10 years, etc., following the initiation of treatment or following the initial diagnosis.

"Time to disease progression" or "TTP" refer to the time, generally measured in weeks or months, from the time of initial treatment (e.g. with a disclosed modulator compound or pharmaceutical composition thereof), until the cancer progresses or worsens. Such progression can be evaluated by the skilled clinician. In the case of triple-negative breast cancer, for instance, progression can be evaluated by RECIST. By "extending TTP" is meant increasing the time to disease progression in a treated patient relative to an untreated patient (i.e. relative to a patient not treated with a disclosed modulator compound or pharmaceutical composition thereof), and/or relative to a patient treated with an approved anti-cancer drug.

Prior to and/or during and/or after therapy using the disclosed methods, the subject may be subjected to a diagnostic or prognostic test as disclosed herein.

Use as Biomarkers

In one embodiment, the subject's cancer expresses UBASH3B. Thus, the UBASH3B gene or protein may be used as a biomarker for determining cancer patient prognosis (e.g. for response to treatment), or susceptibility to treatment (e.g. with an EGFR antagonist or a chemotherapeutic agent).

The term "biomarker" or "marker" as used herein refers generally to a molecule, including a gene, mRNA, protein, carbohydrate structure, or glycolipid, the expression of which in or on a tissue or cell or secreted can be detected by known methods (or methods disclosed herein) and is predictive or can be used to predict (or aid prediction) for a cell, tissue, or patient's responsiveness and/or susceptibility to treatment regimes. Any one or more of the UBASH3B, ETS1, miR-200a, CBL and EGFR genes or proteins disclosed herein may be used as a biomarker to determine a patient's responsiveness and/or susceptibility to a treatment method as disclosed herein. In one embodiment, the biomarker is UBASH3B.

In one embodiment, the subject's cancer overexpresses UBASH3B. By "overexpression" is meant expression of a gene (or its product) at a level that is higher than the level of the gene (or its product) expressed under control conditions, for example in a normal subject (i.e. a subject not having cancer) or in a subject having a non-invasive and/or non-metastatic form of cancer.

The terms "level of expression" or "expression level" are used interchangeably and refer to the amount of a polynucleotide, mRNA, or an amino acid product or protein in a biological sample. The expression level or amount of a biomarker can be assessed and used to determine the response and/or susceptibility to treatment with the disclosed modulator compounds or pharmaceutical compositions thereof. These can be measured by methods known to those skilled in the art and also disclosed herein. In some embodiments, the amount or level of biomarker is determined using IHC (e.g. of patient tumor sample). In some embodiments, the level of expression refers to the amount of a protein in a biological sample as determined using IHC.

Information on expression level of the one or more biomarkers may be used to inform a treatment decision, to constitute information provided on a package insert, or to provide marketing/promotional guidance etc. For example, a patient's cancer having a higher level of UBASH3B gene expression or UBASH3B protein activity relative to the level of UBASH3B gene expression or UBASH3B protein activity in a normal subject (i.e. a subject not having cancer) or in a subject having a non-invasive and/or non-metastatic form of cancer, indicates that the patient may have decreased survival or may be suitable for treatment with a disclosed modulator compound (e.g. a UBASH3B antagonist, or an EGFR antagonist) or a pharmaceutical composition thereof. A patient's cancer having a lower, or the same level of UBASH3B gene expression or UBASH3B protein activity relative to the level of UBASH3B gene expression or UBASH3B protein activity in a normal subject (i.e. a subject not having cancer) or in a subject having a non-invasive and/or non-metastatic form of cancer, indicates that the patient may have increased survival or may not be suitable for treatment with a disclosed modulator compound (e.g. a UBASH3B antagonist, or an EGFR antagonist) or a pharmaceutical composition thereof. In such instances, treatment with an anti-cancer therapy other than the disclosed modulator compounds or pharmaceutical compositions thereof may be preferable.

In one embodiment, there is provided a method of determining cancer patient (e.g. TNBC, prostate cancer, colon cancer) prognosis, comprising the steps of: determining the level of UBASH3B gene expression or UBASH3B protein activity in the patient's cancer (for example, using a technique known in the art or disclosed herein), and classifying the patient as having decreased survival if the patient's cancer has a higher level of UBASH3B gene expression or UBASH3B protein activity relative to the level of UBASH3B gene expression or UBASH3B protein activity in a non-invasive cancer.

In one embodiment, there is provided a method of determining cancer patient (e.g. TNBC, prostate cancer, colon cancer) prognosis, comprising the steps of: determining the level of UBASH3B gene expression or UBASH3B protein activity in the patient's cancer (for example, using a technique known in the art or disclosed herein), and classifying the patient as having decreased survival if the patient's cancer has a higher level of UBASH3B gene expression or UBASH3B protein activity relative to the level of UBASH3B gene expression or UBASH3B protein activity in a normal subject.

In some embodiments, higher UBASH3 gene expression or UBASH3B protein activity indicates likelihood of decreased OS and/or PFS compared to a patient whose cancer has lower UBASH3 gene expression or UBASH3B protein activity. In some embodiments, higher UBASH3B, biomarker expression indicates increased OS and/or PFS when the patient is treated with a disclosed modulator compound (e.g. UBASH3B antagonist, or EFGR antagonist) or a pharmaceutical composition thereof. In some embodiments, lower UBASH3B biomarker expression indicates decreased OS and/or PFS, or no improvement in OS and/or PFS when the patient is treated with a disclosed modulator compound (e.g. UBASH3B antagonist, or EFGR antagonist) or a pharmaceutical composition thereof. In some embodiments, the cancer is TNBC, and higher UBASH3B biomarker expression indicates increased OS and/or PS when the patient is treated with a disclosed modulator compound (e.g. UBASH3B antagonist, or EFGR antagonist) or a pharmaceutical composition thereof. In some embodiments, the cancer is TNBC, and lower UBASH3B biomarker expression indicates decreased OS and/or PFS, or no improvement in OS and/or PFS when the patient is treated with a disclosed modulator compound (e.g. UBASH3B antagonist, or EFGR antagonist) or a pharmaceutical composition thereof. In some embodiments, the cancer is invasive prostate cancer, and lower UBASH3B biomarker expression indicates decreased OS and/or PFS, or no improvement in OS and/or PFS when the patient is treated with a disclosed modulator compound (e.g. UBASH3B antagonist, or EFGR antagonist) or a pharmaceutical composition thereof.

A high UBASH3B biomarker expression may refer to 50% or more of the tumor cells with moderate UBASH3B staining intensity, combined moderate/high UBASH3B staining intensity or high UBASH3B staining intensity, wherein UBASH3B expression is detected using an antibody, wherein the UBASH3B biomarker expression indicates that the patient is likely to have increased OS and/or PFS when the patient is treated with a disclosed modulator compound (e.g. UBASH3B antagonist, or EFGR antagonist) or a pharmaceutical composition thereof.

The amount of UBASH3B biomarker may be determined using a method comprising: (a) performing IHC analysis of a sample (such as a patient cancer sample) with anti-UBASH3B antibody; and b) determining expression of a UBASH3B biomarker in the sample. In some embodiments, IHC staining intensity is determined relative to a reference value. In some embodiments, UBASH3B biomarker expression is determined using a UBASH3B staining intensity scoring scheme as disclosed herein, for example from a value of 0 to 255. In some embodiments, the method further comprises stratifying the patients based on IHC score.

A sample for use in the disclosed methods may be obtained from a subject in need of therapy, and/or undergoing therapy, and/or has undergone therapy. The sample may be obtained from the primary tumor or from a metastatic tumor. The sample may be obtained when the cancer is first diagnosed or, for example, after the tumor has metastasized. In some embodiments, the tumor sample is of breast, prostate, colon, lung, lymph node, liver or brain.

Where the subject has cancer, the sample may be a tumor sample, or other biological sample, such as tissues, cells, body fluids and isolates thereof etc., isolated from the subject, as well as tissues, cells and fluids etc. present within the subject (i.e. the sample is in vivo). Examples of samples include: whole blood, blood fluids (e.g. serum and plasma), lymph and cystic fluids, sputum, stool, tears, mucus, hair, skin, ascitic fluid, cystic fluid, urine, nipple exudates, nipple aspirates, sections of tissues such as biopsy and autopsy samples, frozen sections taken for histologic purposes, archival samples, explants and primary and/or transformed cell cultures derived from patient tissues etc.

The sample may be untreated, treated, diluted or concentrated from a subject.

In one embodiment the sample may be a "breast-associated" body fluid, which is a fluid which, when in the body of a patient, contacts or passes through breast cells or into which cells, nucleic acids or proteins shed from breast cells are capable of passing. Examples of breast-associated body fluids include blood fluids, lymph, cystic fluid, and nipple aspirates.

The sample may be obtained at one or more time points. Expression levels of the marker(s) may optionally be compared with a control sample. The control sample may be a sample derived from a person not having cancer, or a sample derived from a person having a non-invasive and/or non-metastatic form of cancer. One or more control samples may be employed.

The present invention also contemplates sample preparation methods in certain preferred embodiments. For example, prior to or concurrent with gene expression analysis, the sample may be amplified by a variety of mechanisms, some of which may employ amplification techniques such as PCR (e.g. RT-PCR) and the ligase chain reaction (LCR) etc. The sample may be amplified on the array using methods known in the art.

The disclosed method may be useful in selecting a therapy for a patient with cancer (e.g. TNBC, prostate cancer etc.)

comprising determining expression of a UBASH3B biomarker in a sample from the patient, and selecting a cancer medicament based on the level of expression of the biomarker. In one embodiment, a high level of the biomarker(s) (for example, higher level of expression relative to the expression of the biomarker in a normal subject or a cancer patient with a non-invasive or non-metastatic cancer) will result in selection of a disclosed modulator compound or a pharmaceutical composition thereof, for example a UBASH3B antagonist (such as a siRNA or shRNA as disclosed herein), or a EGFR antagonist (such as Erlotinib), for use in treating the patient. In another embodiment, where the biomarker(s) are present in a low (i.e. low or substantially undetectable) level, the patient will be selected for a treatment with an anti-cancer therapy other than a disclosed modulator compound or a pharmaceutical composition thereof, for example with a chemotherapeutic agent (e.g. Paclitaxel). In some embodiments, the sample is of the patient's cancer (e.g. TNBC).

The disclosed method may also be useful in optimizing therapeutic efficacy of a treatment regimen. In some embodiments, detection of a high level of UBASH3B biomarker indicates increased PFS and/or OS when the patient is treated with a UBASH3B antagonist (such as a siRNA or shRNA as disclosed herein), or a EGFR antagonist (such as Erlotinib). In some embodiments, detection of low UBASH3B biomarker indicates a decreased PFS and/or OS, or no improvement in OS and/or PFS when the patient is treated with a UBASH3B antagonist (such as a siRNA or shRNA as disclosed herein), or a EGFR antagonist (such as Erlotinib). In some embodiments, the cancer is TNBC.

Various methods known in the art are available for determining expression of mRNA, protein, or gene amplification. Such methods include, but are not limited to, immunohistochemistry (IHC), gene expression profiling, polymerase chain reaction (PCR) including quantitative real time PCR (qRT-PCR), RNA-Seq, microarray analysis, serial analysis of gene expression (SAGE), MassARRAY technique, or FISH.

Immunohistochemistry (IHC) methods can be used for detecting the expression levels of proteins in a sample. The IHC methods may be a direct assay or an indirect assay. The direct assay typically uses a labeled reagent, such as a fluorescent tag or an enzyme-labeled primary antibody, which can be visualized without further antibody interaction. In an indirect assay, an unconjugated primary antibody is typically used to bind to the antigen and then a labeled secondary antibody is used which binds to the primary antibody. Where the secondary antibody is conjugated to an enzymatic label, a chromogenic or fluorogenic substrate may then be added to provide visualization of the antigen. Signal amplification occurs because several secondary antibodies may react with different epitopes on the primary antibody.

The primary and/or secondary antibody used for immunohistochemistry may be labeled with a detectable moiety. Such labels are known in the art and include enzymes (such as peroxidase) that can catalyse a colour-producing reaction, fluorophores (such as fluorescein, rhodamine, rare earth chelates (europium chelates), Texas Red, dansyl, or commercially available fluorophores such SPECTRUM ORANGE®), and colloidal gold particles.

Following an optional blocking step, the tissue section may be exposed to primary antibody for a sufficient period of time and under suitable conditions such that the primary antibody binds to the target protein antigen in the tissue sample. The extent of binding of antibody to the sample may determined by using any one of the detectable labels discussed above. IHC may be combined with morphological staining, either prior to or thereafter. After deparaffinization, the sections mounted on slides may be stained with a morphological stain, such as hematoxylin for evaluation. The section may be stained with one or more dyes, each of which distinctly stains different cellular components. One of skill in the art will appreciate that staining may be optimized for a given tissue by increasing or decreasing the length of time the slides remain in the dye.

After staining, the tissue section may be analyzed by standard techniques of microscopy. Antibodies suitable for use in IHC are well known in the art and many suitable antibodies are commercially available. Automated systems for slide preparation and IHC processing are available commercially, for example the Ventana® BenchMark XT system. The staining density may then be determined, for example using commercially available software, and given a numerical value for statistical analysis.

Gene expression profiling or analysis include methods based on hybridization analysis of polynucleotides and methods based on sequencing of polynucleotides. Methods based on hybridization include Northern Blotting, in situ hybridization, RNAse protection assays, and polymerase chain reaction (PCR). Antibodies may also be employed that can recognize specific duplexes, including DNA, RNA, DNA-RNA hybrid and DNA-protein duplexes. Methods based on sequencing include Serial Analysis of Gene Expression (SAGE), and Massively Parallel Signature Sequencing (MPSS).

PCR may be used to compare mRNA levels in different samples, for example in normal and cancerous (e.g. non-invasive, invasive or metastatic) tissues, and in samples with or without drug treatment. The starting material for a PCR is typically total RNA isolated from a sample, such as human tumors or tumor cell lines, and corresponding normal tissues or cell lines, respectively. General methods for mRNA extraction are well known in the art and are disclosed in standard textbooks of molecular biology, including Ausubel et ah, Current Protocols of Molecular Biology, John Wiley and Sons (1997). The isolated RNA may then be reverse transcribed into cDNA using reverse transcriptases (e.g. avilo myeloblastosis virus reverse transcriptase (AMV-RT) or Moloney murine leukemia virus reverse transcriptase (MMLV-RT)) and specific primers, random hexamers, or oligo-dT primers, depending on the circumstances and the goal of expression profiling. The derived cDNA can then be used as a template in the subsequent PCR reaction, using thermostable DNA-dependent DNA polymerases such as the Taq DNA polymerase, which has a 5'-3' nuclease activity but lacks a 3'-5' proofreading endonuclease activity.

Primers and probes used for PCR are designed based upon the sequences present in the gene to be amplified. Factors considered in PCR primer design include primer length, melting temperature (Tm), and G/C content, specificity, complementary primer sequences, and 3'-end sequence. Optimal PCR primers may be 17-30 bases in length, and may contain about 20-80%, such as, for example, about 50-60% G+C bases. Tm's of between 50 and 80° C., e.g. about 50 to 70° C., may be used.

A variation of the PCR technique is quantitative real time PCR (qRT-PCR), which measures PCR product accumulation through a dual-labeled fluorigenic probe (i.e. TAQMAN® probe). qPCR can be performed using commercially available equipment, such as, for example, ABI PRISM 7700® Sequence Detection System® (Perkin-Elmer-Applied Biosystems, Foster City, Calif., USA) and CFX96 Real-Time PCR Detection System (Bio-Rad, Hercules, Calif.). The system amplifies samples in a 96-well format on a thermocycler. During amplification, laser-induced fluorescent signal is collected in real-time through fiber optics cables for all 96 wells, and detected at the CCD. Fluorescence values are recorded during every PCR cycle and represent the amount of product amplified to that point in the amplification reaction. The point when the fluorescent signal is first recorded as statistically significant is the threshold cycle (Ct) value which is used to compare the level of gene expression between different samples, for example between a target and reference sample. An internal standard (for example a gene that is unaffected by the experimental treatment such as housekeeping genes like glyceraldehyde-3-phosphate-dehydrogenase (GAPDH) and P-actin) may be used to minimize errors and the effect of sample-to-sample variation.

RNA-Seq, also called Whole Transcriptome Shotgun Sequencing (WTSS) refers to the use of high-throughput sequencing technologies to sequence cDNA to obtain information about a sample's RNA content. RNA-Seq may be performed on a variety of platforms, such as using the Illumina Genome Analyzer platform (for example as described in Mortazavi A et al., *Nature Methods* 5(7): 621-628 (2008)), ABI Solid Sequencing (for example as described in Cloonan N et al., *Nature Methods* 5(7):613-619 (2008)), or Life Science's 454 Sequencing (for example as described in Barbazuk W B et al., *The Plant Journal* 51(5): 910-918 (2007)). RNA-Seq techniques that may be used are also described in Wang et al., *Nature Reviews Genetics* 10 (1):57-63 (January 2009); Ryan et al., *BioTechniques* 45 (1):81-94 (2008); and Maher et al., *Nature* 458(7234):97-101 (January 2009).

Differential gene expression can also be identified, or confirmed using microarrays, where polynucleotide sequences of interest (including cDNAs and oligonucleotides) are plated, or arrayed, on a microchip substrate. The arrayed sequences are then hybridized with specific DNA probes from cells or tissues of interest. The source of mRNA may be total RNA isolated from human tumors or tumor cell lines, and corresponding normal tissues or cell lines. The chips are washed to remove non-specifically bound probes, and scanned by detection methods such as confocal laser microscopy or CCD camera. Quantitation of hybridization of each arrayed element enables assessment of corresponding mRNA abundance. Microarray analysis can be performed by commercially available equipment, following manufacturer's protocols, such as by using the Affymetrix GENCHIP™ technology, or Incyte's microarray technology.

Serial analysis of gene expression (SAGE), or variants thereof, may be used to simultaneously and quantitatively analyze a large number of gene transcripts, without the need of providing an individual hybridization probe for each transcript. A short sequence tag (about 10-14 bp) is generated that contains sufficient information to uniquely identify a transcript. Many transcripts are then linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

MassARRAY (Sequenom, San Diego, Calif.) technology is an automated, high-throughput method of gene expression analysis using mass spectrometry (MS) for detection. Isolated RNA is reverse transcribed and amplified (e.g. by PCR), and the cDNAs are subjected to primer extension. The cDNA-derived primer extension products are purified, and dispensed on, a chip array that is pre-loaded with the components needed for MALDI-TOF MS sample preparation. The various cDNAs present in the reaction are quantified by analyzing the peak areas in the mass spectrum obtained.

Fluorescence in situ hybridization (FISH) enables visualization and mapping of genetic material in an individual's cells, including specific genes or portions of genes. The chromosomes to be studied are first firmly attached to a substrate, such as a glass slide. Repetitive DNA sequences are then blocked by adding short fragments of DNA to the sample in order to reduce the occurrence of false positive signals. Fluorescently labeled single stranded DNA probes that hybridize to the genes of interest are then applied to the chromosomal DNA and incubated for approximately 12 hours to allow the probes to hybridize to their respective targets. Unhybridized or partially hybridized probes are removed by washing and the probes are then visualized and quantified using fluorescence microscopy.

Proteomics, which enables study of the global changes of protein expression in a sample (also referred to as "expression proteomics"), may be used to supplement the methods of gene profiling as disclosed herein. Proteomics typically includes (1) separating individual proteins in a sample by 2-D gel electrophoresis (2-D PAGE); (2) identifying the individual proteins recovered from the gel (for example, by mass spectrometry or N-terminal sequencing); and (3) analyzing the data using bioinformatics.

In one embodiment, protein expression is quantified. Such protein analysis may be performed using IHC as described herein on patient tumor samples. Antibodies (e.g. monoclonal antibodies specific for each marker) or antisera (e.g. polyclonal antisera) may be used to detect expression. The antibodies can be detected by direct labeling of the antibodies themselves, for example, with radioactive labels, fluorescent labels, hapten labels such as biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody.

IHC analysis may further comprise morphological staining, either prior to or after IHC analysis. In one embodiment, hematoxylin (e.g. Hematoxylin II (Ventana)) is used for staining cellular nucleic of the slides. When lighter blue nuclei are desired, a bluing reagent may be used following hematoxylin staining.

Detection of UBASH3B biomarker using IHC is disclosed herein, and a UBASH3B staining intensity scoring scheme with numerical values of 0 to 255 is disclosed herein.

In one embodiment, amount of UBASH3B biomarker is determined using a method comprising: (a) performing gene expression profiling, PCR (such as rtPCR), RNA-seq, microarray analysis, SAGE, MassARRAY technique, or FISH on a sample (such as a patient cancer sample) with anti-UBASH3B antibody; and b) determining expression of a UBASH3B biomarker in the sample.

Other biomarkers may also be detected using the disclosed methods. Exemplary other biomarkers include EGFR, ETS1, miR-200a, and CBL.

Articles of Manufacture and Kits

Also disclosed is an article of manufacture containing materials useful for the treatment of cancer. The article of manufacture may comprise a container, a label and a package insert. Suitable containers include, for example, bottles, vials, syringes, and the like, which may be made from a variety of materials such as glass or plastic. The container may hold one or more disclosed modulator compounds and/or compositions thereof and may have a sterile access port (for example the container may be an intravenous solution bag or a vial having a stopper pierceable by a hypodermic injection needle). The label on, or associated with, the container may indicate that the composition is used for treating one or more types of cancer as discussed herein.

The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, and syringes. In addition, the article of manufacture may comprise a package insert with instructions for use, including for example instructing the user of the disclosed modulator compound(s) or compositions thereof to administer the disclosed modulator compound(s) or compositions thereof, and optionally an anti-cancer drug, to a patient with cancer (e.g. breast cancer, prostate cancer, etc.). The patient may have previously been treated with one or more anti-cancer therapy for example, for TNBC or invasive prostate cancer. The package insert may optionally contain some or all of the results found in the Examples as disclosed herein.

The disclosed modulator compound(s) or compositions thereof may also be packaged alone or in combination with other anti-cancer drugs as a kit. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. In certain embodiments, the instructions comprises instructions for use, including for example instructing the user of the composition to administer the disclosed modulator compound(s) or compositions thereof and an anti-cancer drug to a patient who has previously been treated, for example for breast cancer or prostate cancer. The instructions may optionally contain some or all of the results found in the Examples disclosed herein. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1(a) is a heat map representation of 103 genes that expressed more than 2-fold higher in TNBC tissues and cell lines compared to non-TNBC breast cancer tissues and cell lines. Expressions of ER (ESR1) and its related genes FOXA1 and GATA3 as well as AR and PGR are also shown. 19 "druggable" genes are listed on the right. Genes in bold (PSAT1, B3GNT5, UBASH3B, AGPAT4, ACOT9, CDK6, HYAL3) showed association with poor metastasis-free survival.

FIG. 1(b) shows representative images of MB231 cells cultured in 3D Matrigel on the left. The cells were depleted of the indicated genes using two independent siRNA sequences, siRNA#1 and siRNA#2. Knockdown efficiency was assessed by real-time PCR and is shown on the right.

FIG. 1(c) shows real-time PCR and Western blot analysis of UBASH3B expression in a panel of breast cancer cell lines. *$P<0.05$, unpaired two-tailed t-test.

FIG. 1(d) depicts box plots showing the mRNA expression of UBASH3B in two Oncomine datasets, Waddell and TCGA breast.

FIG. 1(e) show representative images of immunohistochemistry (IHC) staining of UBASH3B on paraffin-embedded breast cancer tissues from JWCI patient cohort. Staining was graded based on the intensity and P-value was calculated by Wilcoxon test.

FIG. 1(f) shows the result of IHC staining of UBASH3B on tissue microarray consisting of invasive (n=73) and non-invasive (n=21) breast cancer tissues. The proportion of positive-stained cytoplasm was scored and plotted in box plot representation. P-values were calculated by unpaired two-tailed t-test.

FIG. 1(g) shows Kaplan-Meier analyses of disease-specific survival of breast cancer patients of GSE12276 dataset. Patients whose tumors have expression of the UBASH3B higher than mean were labeled in light grey, and those with expression of this gene lower than mean were labeled in dark grey. P-values were calculated using Cox proportional hazards regression model, Wald test. Error bars, mean+SEM.

FIG. 1(h) depicts a Venn diagram showing the overlap of genes overexpressed in TNBC tissues and cell lines.

FIG. 1(i) shows Kaplan-Meier analyses of disease-specific survival of breast cancer patients of the indicated published datasets. Patients whose tumors have expression of the gene higher than the mean were labeled in light grey, and those with expression of the gene lower than the mean were labeled in dark grey. P-values were calculated using Cox proportional hazards regression model, Wald test.

FIG. 1(j) shows the real-time PCR analysis of UBASH3A in a panel of breast cancer cell lines.

FIG. 1(k) shows the real-time PCR and Western blot analysis of UBASH3B expression in a panel of prostate cancer cell lines. *$P<0.05$, unpaired two-tailed t-test.

FIG. 1(l) depicts box plots showing the mRNA expression of UBASH3B in an Oncomine prostate cancer dataset. Error bars, mean+SEM.

FIG. 2(a) shows a schematic diagram of UBASH3B gene structure. TSS, Transcription start site.

FIG. 2(b) shows real-time PCR and Western blot analysis of ETS1 expression in a panel of breast cancer cell lines. *$P<0.05$, unpaired two-tailed t-test.

FIG. 2(c) shows the results of ChIP assay of ETS1 on the promoter of UBASH3B. 8 primer pairs were designed ±2000 bp flanking TSS. Quantification of binding was assessed by real-time PCR and represented as percent input.

FIG. 2(d) shows real-time PCR and Western blot analysis of UBASH3B expression after ETS1 depletion in BT549. *$P<0.05$, paired two-tailed t-test.

FIG. 2(e) shows real-time PCR analysis of UBASH3B in MB231 upon treatment of 5 µM of U0126 for the indicated time points. *$P<0.05$, paired two-tailed t-test.

FIG. 2(f) depicts a dot plot showing the positive correlation of ETS1 and UBASH3B mRNA expression in patient tissues from the GSE12276 dataset on the left. A bar chart representation of the proportion of patients with the expression of UBASH3B and ETS1 higher than (dark grey) or lower than (light grey) the mean expression in GSE12276 dataset is shown on the right. *P=0.019; P=0.013; *P=0.031. P-values were calculated using two sided Fisher's exact test.

FIG. 2(g) shows Kaplan-Meier analysis of disease-specific survival of breast cancer patients of GSE12276 dataset. Patients whose tumors, have expression of ETS1 higher than mean were labeled in light grey, and those with underexpression of this gene lower than median were labeled in dark grey. P-values were calculated using Cox proportional hazards regression model, Wald test. Error bars, mean+SEM.

FIG. 2(h) depicts box plots showing the mRNA expression of ETS1 in JWCI breast cancer tissue samples based on gene-expression profiling. P-values were calculated by unpaired two-tailed t-test.

FIG. 2(i) depicts box plots showing the mRNA expression of ETS1 in two Oncomine datasets, Waddell and TCGA breast.

FIG. 2(j) shows real-time PCR and Western blot analysis of UBASH3B expression after ETS1 depletion in DU145 and PC3. *P<0.05, paired two-tailed t-test. Error bars, mean+SEM.

FIG. 3(a) shows a schematic diagram of UBASH3B gene structure. TAA, Stop codon; 3' UTR, 3'-untranslated region; MRE, miRNA response element.

FIG. 3(b) shows real-time PCR analysis of miR200a expression in a panel of breast cancer cell lines. *P<0.05, unpaired two-tailed t-test.

FIG. 3(c) depicts a schematic diagram showing the four miRNA response element (MRE) (SEQ ID NO:43-46) in the 3'UTR of the UBASH3B gene base-paired to miR200a mature sequence (SEQ ID NO: 47). Two regions (P1 and P2) were cloned into a luciferase reporter pMIR-REPORT. P1 mut and P2 mut were constructed by mutating the MRE to the mutant sequence (SEQ ID NO: 48) as indicated (left). Luciferase reporter assay in cells co-transfected with miR200a or miR200c mimics and pMIR-REPORT containing wild-type or mutant P1 or P2 is shown on the right. *P<0.05, paired two-tailed t-test.

FIG. 3(d) shows real-time PCR and Western blot analysis of UBASH3B expression in MB231 and BT549 overexpressing miR200a or miR200c mimics. Protein expression of ZEB1 and ZEB2 were also assessed. *P<0.05, paired two-tailed t-test.

FIG. 3(e) shows real-time PCR and Western blot analysis of UBASH3B expression in the indicated cells transfected with miR200a antagomir. *P<0.05, paired two-tailed t-test.

FIG. 3(f) shows real-time PCR and Western blot analysis of UBASH3B expression in the indicated cells transfected with miR200a mimics and/or ETS1 siRNA. *P<0.05, paired two-tailed t-test. Error bars, mean+SEM.

FIG. 3(g) shows real-time PCR analysis of miR200b/c in a panel of breast cancer cell lines. *P<0.05, unpaired two-tailed t-test.

FIG. 3(h) depicts box plots showing the miR200a/b/c expression assessed by RT-qPCR in breast cancer specimens. P-values were calculated by unpaired two-tailed t-test.

FIG. 3(i) shows real-time PCR of UBASH3B expression in DU145 and PC3 prostate cancer lines overexpressing miR200a or miR200c mimics. *P<0.05, paired two-tailed t-test. Error bars, mean+/−SEM.

FIG. 4(a) shows the results of Transwell Matrigel invasion assay conducted on MB231 and BT549 depleted of UBASH3B using two independent siRNAs in the presence or absence of EGF as a chemoattractant (top). EGFR and UBASH3B expression was assessed by Western blot analysis (bottom). *P<0.05, paired two-tailed t-test.

FIG. 4(b) shows contingency analysis of UBASH3B and EGFR IHC staining on 73 breast cancer tissues from JWCI patient cohort. P-value was calculated using Fisher's exact test.

FIG. 4(c) shows UBASH3B expression assessed by Western blot analysis (left). Representative images of indicated cells grown in 3D Matrigel are shown on the right.

FIG. 4(d) shows Western blot analysis of EGFR and UBASH3B expression on the left, and the results of transwell invasion assay on the right using MB231-LN cells with UBASH3B depletion and EGFR overexpression. *P<0.05, paired two-tailed t-test.

FIG. 4(e) shows the results of methylcellulose assay of MB231-LN stable knockdown cells in response to Erlotinib with the indicated concentrations.

FIG. 4(f) shows the growth curve of subcutaneous tumor formed by control and UBASH3B KD MB231-LN cells in female athymic nude mice treated with vehicle or Erlotinib (n=10 per category) by oral gavage. *P<0.05, n.s., no significant difference.

FIG. 4(g) shows the EC50 of MB231-LN stable cell lines towards Erlotinib as assessed by methylcellulose assay. *P<0.05, paired two-tailed t-test. Error bars, mean+SEM.

FIG. 4(h) shows the results of transwell matrigel invasion assay on DU145 and PC3 prostate cancer lines in the presence of EGF as a chemoattractant (top). *P<0.05, paired two-tailed t-test. UBASH3B knockdown efficiency was assessed by Western blotting (bottom).

FIG. 4(i) shows the results of transwell matrigel invasion assay conducted on MB231 cells with stable overexpression of UBASH3B followed by the depletion of endogeneous UBASH3B using 3'UTR siRNA. *P<0.05, paired two-tailed t-test.

FIG. 4(j) shows Western blot analysis of EGFR and UBASH3B expression in normal immortalized breast cell line, MCF10A.

FIG. 4(k) shows the results of tumorsphere assay of MB231 depleted of UBASH3B using two independent siRNAs. *P<0.05, paired two-tailed t-test. Representative images of the tumorspheres are shown.

FIG. 4(l) shows the results of tumorsphere assay on DU145 and PC3 depleted of UBASH3B. *P<0.05, paired two-tailed t-test.

FIG. 4(m) shows the results of cell viability assay on MB231, BT549, DU145, and PC3 depleted with UBASH3B.

FIG. 4(n) shows the results of 3D Matrigel assay using MB231-LN cells with UBASH3B depletion and EGFR overexpression.

FIG. 4(o) shows the results of tumorsphere assay using MB231-LN cells with UBASH3B depletion and EGFR overexpression. *P<0.05, paired two-tailed t-test. Error bars, mean+SEM.

FIG. 5(a) shows the Western Blot on UBASH3B knockdown by shRNAs in LM2 cells.

FIG. 5(b) shows BLI curves of lung metastasis development in female athymic nude mice injected via lateral tail vein with control and UBASH3B KD cells. Data represent mean±s.e. n=9. *P<0.05, **P<0.01 by Mann-Whitney test.

FIG. 5(c) shows representative BLI images of mice of (b), at 4 wks post injection.

FIG. 5(d) shows whole lung images of mice from a repeat experiment as (b), at 4 wks post injection.

FIG. 5(e) shows Kaplan-Meier curves of mice from (b), n=9. *P<0.05, Cox proportional HR=3.51 (95% CI=1.10-11.18), **P<0.005, Cox HR=6.99 (95% CI=1.46-33.50).

FIG. 5(f) shows the Western Blot on UBASH3B knock-down by shRNA in 4T1 cells.

FIG. 5(g) depicts a box plot showing the number of lung metastasis nodules from experimental metastases generated by control or UBASH3B KD of 4T1 cells at 2 weeks after tail vein injection, p-value by student t-test. n=7-8

FIG. 5(h) shows representative gross images of lung metastasis from mice as in (g).

FIG. 5(i) depicts a box plot showing the number of lung metastasis nodules from spontaneous metastases generated by control or UBASH3B knock-down 4T1 cells after mammary fat pad injection, p-value by student t-test. n=8, **P<0.01

FIG. 5(j) shows representative gross images of spontaneous lung metastasis from mice as (i).

FIG. 5(k) shows lung metastasis of MB231-LN cells of control (NC) or shUBASH3B (KD), with ectopic expression of vector or EGFR.

FIG. 5(l) shows the results of methylcellulose assay of MB231-LN stable knockdown cells in response to Paclitaxel with indicated concentrations.

FIG. 5(m) shows the results of real-time PCR and Western blot analysis of UBASH3B expression in SUM159PT parental and Paclitaxel-resistant (SUM159PT-R) cell lines.

FIG. 5(n) shows depletion of UBASH3B in SUM159PT and SUM159PT-R cell lines using two independent siRNA followed by treatment of Paclitaxel in a range of dosages for 72 hrs. Cell viability assay was performed and EC50 of Paclitaxel in each sample was determined and shown at the top. UBASH3B knockdown efficiency was assessed by Western blotting, shown at the bottom. *P<0.05, paired two-tailed t-test. Error bars, mean+SEM.

FIG. 6(a) shows Matrigel invasion of cells expressing wild-type (WT) or mutant UBASH3B (H391A) in the presence or absence of EGF as chemoattractant. *P<0.05, paired two-tailed t-test.

FIG. 6(b) shows EGFR and UBASH3B expression assessed by Western blot analysis.

FIG. 6(c) shows BLI values of lung metastasis development in female NOD/SCID mice at week 6 after injected with control and wild type and mutant UBASH3B cells via lateral tail vein (left). Data represent mean±SEM; n=12 per category. *P<0.05, unpaired two-sided student t-test. Representative BLI images of mice at 6 wks post injection are shown in the middle. Kaplan-Meier analysis was performed and shown on the right. **P<0.01, log-rank test.

FIG. 6(d) shows the results of co-immunoprecipitation assay conducted on HEK293T with transient expression of CBL and wild-type (WT) or mutant UBASH3B in the presence or absence of EGF.

FIG. 6(e) shows the results of co-immunoprecipitation assay conducted on BT549 stably expressing wild-type (WT) or mutant UBASH3B in the presence or absence of EGF.

FIG. 6(f) shows western blot analysis of EGFR, UBASH3B, and CBL protein expression in BT549 depleted with UBASH3B and/or CBL.

FIG. 6(g) depicts a mechanistic model showing that the expression of UBASH3B is positively regulated by ETS1 and negatively regulated by miR200a, which results in the overexpression of UBASH3B in the aggressive cancer cells. The overexpressed UBASH3B in turn dephosphorylates CBL, which would otherwise degrade EGFR-protein. As the result, the high level of EGFR protein would in turn promote the invasiveness of the cancer cells. Error bars, mean+SEM.

DETAILED DESCRIPTION OF DRAWINGS

Examples

Figure 1:
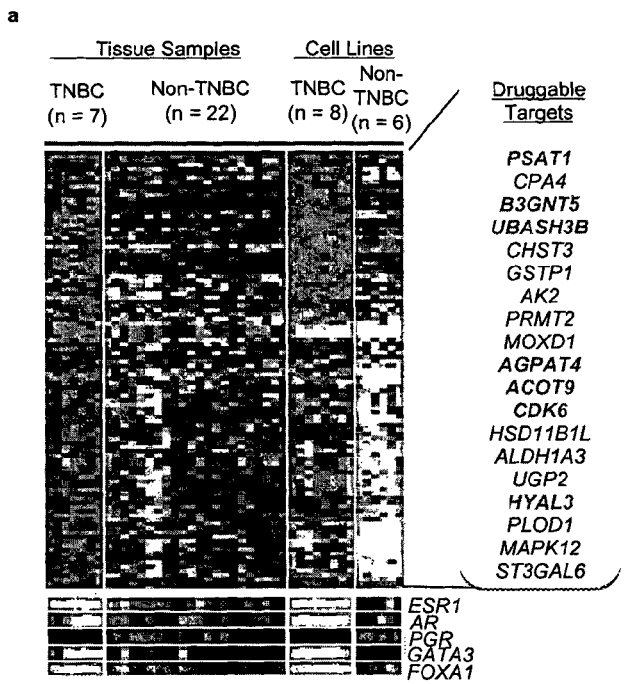
FIG. 1. Use of Functional Genomics for Identification of the Overexpression of UBASH3B in TNBC and Association with Poor Disease Prognosis
Figure 1:
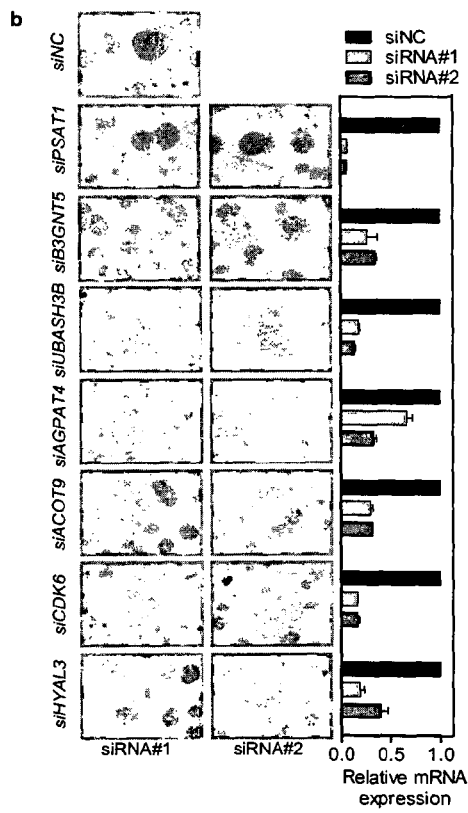

Non-limiting examples of the invention, including the best mode, and a comparative example will be further described in greater detail by reference to specific Examples, which should not be construed as in any way limiting the scope of the invention.

Example 1

Experimental Methods Used

Dataset and Survival Analysis.

The cancer subtype-specific gene expression analysis was performed on Waddell, TCGA breast cancer datasets and Varambally prostate cancer dataset using Oncomine. Gene expression profiling was performed on a panel of breast cancer cell lines purchased from ATCC and primary breast tumor specimens were obtained from John Wayne Cancer Institute (JWCI, Santa Monica, Calif. USA), which were obtained using protocols approved by the Institutional Review Board of the National University of Singapore (NUS-IRB); informed consent was obtained from each individual who provided the tissues. The survival analysis was performed on breast cancer datasets from GSE12276, GSE1456, and GSE2034 with relevant clinical information as previously described[1-3]. Breast cancer patients were classified into groups with higher or lower expression of the indicated genes based on the mean value of the gene expression. Using the survival event status and time information, the survival association of expression status (high/low expression) was computed using Cox-Proportional Hazards model implementation (coxph) available in R-library "survival". Kaplan-Meier survival analysis was used for the analysis of clinical outcome.

Tumor Xenografts and Metastasis Analysis.

All animal experiments were performed in accordance with the protocols approved by Institutional Animal Care and Use Committee (IACUC) of Princeton University. 4-6 weeks old female athymic nude mice (NCI) were used to test lung metastasis development with LM2 and sublines. 4-6 weeks old female Balb/c wild type mice (NCI) were used for all xenograft experiments with 4T1. Lateral tail vein intravenous injection, and orthotopic mammary fat pad injection of tumor cells were performed as described[4]. For luciferase labeled LM2 cells, development of metastases was monitored by BLI with the IVIS Imaging System (Xenogen) and analyzed with Living Image software (Xenogen) as described[5]. Mammary primary tumor size measurement was performed as previously described[4]. Experimental and spontaneous lung metastases were quantified based on visual examination and manually counting Bouin's solution fixed lungs. All raw measurements were presented as mean±SEM (standard error of the mean). Comparisons of curves between primary tumor and BLI lung metastasis growth were performed using repeated Anova analysis. Survival analysis was performed using Kaplan-Meier estimator and log-rank test. The relative hazard ratio between different groups was calculated based on Cox-proportional hazards model and presented as HR (95% CI). Other comparisons were performed using unpaired two-sided Student's t-test without equal variance assumption or nonparametric Mann-Whitney test. All statistic calculations were performed with Excel, Stata 7 and EPI info. For in vivo Erlotinib treatment and lung colonization assay of MB231-LN overexpressed with wild type and mutant UBASH3B, the experiments were conducted in compliance with animal protocols approved by the ASTAR-Biopolis Institutional Animal Care and Use Committee (IACUC) of Singapore. For in vivo Erlotinib treatment, both control cell and UBASH3B KD MB231-LN cells were subcutaneously injected into 6-8 week female nude mice at $5\times10^6$ cells, followed by treatment with vehicle or Erlotinib (LC lab, #E-4007) at 100 mg/kg by oral gavage with 6 consecutive days per week for 4 weeks after average tumor volume reached around 150 mm$^3$. Tumors were measured by calliper three times per week and tumors volume was calculated with formula: V=W*W*L/2. For lung colonization assay of MB231-LN overexpressed with wild type and mutant UBASH3B, $2\times10^5$ cells of MB231-LN control and wild type and mutant UBASH3B cells were injected via tail vein. The lung metastasis development was monitored once a week by BLI with IVIS imaging System.

Immunohistochemistry (IHC).

Tissue microarray (BR20020) was purchased from US Biomax and paraffin-embedded tissue samples were obtained from JWCI and Tan Tock Seng Hospital (TTSH), Singapore. Staining and image analysis of tissue microarray were performed by Histopathology Department from Institute of Molecular and Cell Biology, Agency for Science, Technology, and Research (A*STAR), Singapore. Anti-EGFR (clone 31G7) was purchased from Invitrogen, Calif., USA and anti-UBASH3B (ab34781) was purchased from Abcam, MA, USA. Image analysis of paraffin-embedded tissue specimens were performed by DH and JW from JWCI. In brief, five-micron paraffin-embedded tissue sections cut, deparaffinized, rehydrated, antigens were retrieved by Proteinase K solution; sections were then incubated in 3% $H_2O_2$ at room temperature to block endogenous peroxidase. Slides were incubated in primary Ab against EGFR for 1 hr followed by 30 min incubation with anti-mouse Labelled Polymer (Dako, Calif.). Specificity of the immunostaining was determined by the inclusion of isotype-specific IgG as negative control. The detection system was DAB+ Substrate-Chromogen Solution (Dako). The sections were counterstained with hematoxylin. For UBASH3B staining, slides were incubated in primary Ab 45 min followed by 10 min incubation with anti-rabbit Labelled Polymer. A photograph of each IHC-stained section was taken for analysis using a Nikon Eclipse Ti microscope and NIS elements software (Nikon, Melville, N.Y., USA). After the IHC, staining density was determined by Image J software (http://sbweb.nih.gov/ij/) following adjustment for background on each selected fields of image of the immunostained slide, the density of the individual breast cancer specimen was quantified and given a numerical value from 0-255 as previously described[6]. Breast cancer specimens were assessed in duplicates, the average of the two duplicate specimens staining intensity of the field values was used for statistical analysis.

RT-qPCR Analysis of miRNA-200.

The use of human subjects was approved by the Western Institutional Review Board (WIRB). Paraffin-embedded archival tissue (PEAT) samples of primary tumors from breast cancer patients with TNBC and Luminal A/B tumors who underwent surgical resection at JWCI's breast center were obtained (JWCI). Three 10 μM thick tissue sections were cut from each PEAT and manual needle microdissection was performed to isolate tumor tissue for RNA extraction. Total RNA was extracted as previously described[6]. Total RNA was assessed for purity by UV spectrophotometry and quantified using the Quant-iT Ribogreen RNA assay kit (Invitrogen, Carlsbad, Calif., USA). 25 ng of total RNA was reverse transcribed using the qScript microRNA cDNA synthesis kit (Quanta Biosciences, Gaithersburg, Md., USA). The transcribed cDNA was diluted 10-fold and used as a qPCR template. PerfeCTa® miRNA assay primers were obtained from Quanta Biosciences. Each qPCR reaction contained 4.6 μL of diluted cDNA, 5 μL PerfeCTa® SYBR® Green SuperMix (Quanta Biosciences) and miRNA specific forward primer targeting the specific miRNA and universal reverse primer. Each sample was assessed in triplicate in 40 cycles of 95° C. for 5 sec and 60° C. for 30 sec. The CFX96 Real-Time PCR Detection System (Bio-Rad, Hercules, Calif.) was used for qPCR with melting-curve analysis. Target amplification for miRNA 200A, B and C was normalized with the reference control (MDA-MB-231) and comparative quantification was recorded at the difference in real-time quantification cycle (Cq) between the target and reference sample (ΔCq). The relative copy number was calculated as 2-ΔCq.

Luciferase Assays.

HCT116 cells were plated at a density of $5\times10^4$ cells per well in 24-well plate format and transfected with 10 ng of pMIR REPORT containing the respective miRNA responsive regions of UBASH3B 3' UTR sequence, 40 nM of miRNA mimics and 5 ng of pRL null internal control simultaneously on the next day. At 48 h after transfection, the luciferase activities were measured using the Dual Luciferase system (Promega). All luciferase readings were first normalized to corresponding internal control pRL null Renilla luciferase readings. The resulting relative activities were further normalized to appropriate controls.

Transwell Matrigel Invasion Assay.

24-well FluorBlok transwell insert (Falcon) with a pore size of 5um was pre-coated with 500 ug/ml (or 1 mg/ml for prostate cancer cell lines) of growth factor-reduced Matrigel (Falcon) for 3-4 hours at 37° C. $5\times10^4$ MB231, BT549, DU145, and PC3 with indicated treatments were seeded in each insert with DMEM containing 0.5% FBS. DMEM supplemented with 0.5% FBS and 100 ng/ml EGF was added outside the chamber as a chemoattractant. Invaded cells were fixed after 48 hours of incubation by using 3.7% formaldehyde and stained with 25 ug/ml propidium iodide (Sigma). 10 fields per inserts were scanned and numbers of invaded cells were counted with Cellomics ArrayScan.

3-Dimensional Matrigel Assay.

8-well chamber slides (Falcon) were pre-coated with 7.6 mg/ml growth factor-reduced Matrigel (Falcon) for 30 min at 37° C. $5\times10^3$ MB231 and BT549 with indicated treatments were seeded in each well with DMEM containing 10% FBS and 150 ug/ml Matrigel.

Methylcellulose Assay.

96-well plates were pre-coated with 0.6% soft agar. Single cell suspension of target cells were plated at a density of 1500 cells per well containing 100 ul of complete DMEM with 0.5% methylcellulose (Sigma). After 14 days of incubation, cell colonies were stained with 4 μg/ml p-Iodonitrotetrazolium Violet (INT) overnight and the number of colonies formed was quantified using Optronix Gelcount software.

Tumorsphere Assay.

Single cell suspension of target cells were plated at a density of $1\times10^4$ cells/well in 6-well ultra-low attachment plates (Corning) containing 3 ml MammoCult medium supplemented with 0.5 μg/ml hydrocortisone and 4 μg/ml heparin (STEMCELL Technologies) and cultured for 7 days. Tumorspheres formed were stained with 4 µg/ml p-Iodonitrotetrazolium Violet (INT) overnight and quantified using Optronix Gelcount software. For EGFR rescue assay, tumospheres formed at day 7 were spun down, trypsinized and re-plated at a density of 1×10⁴ cells/well to access the cancer stem cell regeneration capacity.

Cell Viability Assay.

Cell viability was determined using CellTiter-Glo Luminescent Cell Viability Assay (Promega) as instructed by manufacturer's manual. 1000 cells were plated in 96-well plate and the readings were taken for 5 consecutive days using CellTiter-Glo kit (Promega).

Cell Culture and Treatment.

All cell lines were obtained from ATCC (Manassas, Va.) except for MB231-Luc-D3-H2LN (MB231-LN) which was purchased from Bioware, Sciencewerk, Singapore. MB231, BT549, MCF7, T47D, BT474, MB361, MB415, MB436, Hs578T, MB157, PC3, DU145, HCT116, and HEK293T cell lines were grown in Dulbecco's modified Eagle's medium (DMEM) supplemented with 10% fetal bovine serum (FBS). VCap cells were grown in the addition of 1% sodium pyruvate and 1% sodium bicarbonate. SKBR3 cells were maintained in McCoy's 5A medium. HCC1806, HCC1937, 22RV1, and LnCap were maintained in RPMI medium supplemented with 10% FBS. MCF10A normal breast epithelial cell line was grown in DMEM/F12 supplemented with 5% horse serum, 20 ng/ml EGF, 0.5 mg/ml hydrocortisone, 100 ng/ml cholera toxin, 10 µg/ml insulin, and penicillin/streptomycin (Invitrogen). All media were supplemented with 5000 U/mL penicillin/streptomycin (Invitrogen). All cells were maintained at 37° C. with 5% $CO_2$. For Western blotting analysis after EGF treatment, cells were treated with 100 ng/ml EGF in DMEM supplemented with 0.5% FBS for 24 h and harvested for downstream assays.

Small Interfering RNA and Plasmids.

siRNA and plasmids transfections were conducted using Lipofectamine RNAiMax (Invitrogen) and FugeneHD (Roche Applied Science), respectively To generate stable over-expression cell lines, target genes from their respective transient expression plasmids were subcloned into the PMN retroviral expression vector. Virally infected cells were sorted based on GFP over-expression. pcDNA4-UBASH3B wild type was cloned using cDNA as the template and pcDNA4-UBASH3B H391A was generated using GeneTailor Site-Directed Mutagenesis kit (Invitrogen). UBASH3B small hairpin RNA constructs were generated by inserting siRNA hairpin oligonucleotides into pSIREN-RetroQ (Clontech Laboratories). Target-specific siRNA and non-targeting control siRNA were purchased from 1st Base Singapore with the following target sequences:

```
UBASH3B siRNA#1:
                               (SEQ ID NO: 1)
5'-CCGGCUUAUUUGAGUGGAC-3'

UBASH3B siRNA#2:
                               (SEQ ID NO: 2)
5'-CCUCAUAAGAAGCAGCUAC-3'

UBASH3B siRNA#3:
                               (SEQ ID NO: 3)
5'-GCACUGCAACUGAGAAAUU-3'

ETS1 siRNA#1:
                               (SEQ ID NO: 4)
5'-CCCAGCCUAUCCAGAAUCC-3'

ETS1 siRNA#2:
                               (SEQ ID NO: 5)
5'-GGAAUUACUCACUGAUAAA-3'

CBL siRNA:
                               (SEQ ID NO: 6)
5'-CCAAUCACAAGCUUAGUUAUCAGG-3'
```

All siRNA were designed by 1st Base Singapore except for ETS1 siRNA#1 which was referenced from a previously published paper[7]. Oligo miRNA mimics and antagomirs were purchased from Dharmacon, Inc. (Chicago, Ill., USA). For transfection, 30 nM siRNAs, 15 nM miRNA mimics or 100 nM iRNA antagomirs were used to transfect cells. 48 h after transfection cell pellets were collected and subjected indicated assays.

Knock down of mouse UBASH3B in 4T1 cells were achieved by using lentiviral Mission shRNA constructs from Sigma Aldrich. The two KD constructs are:

```
TRCN0000099665 (targeting 3'UTR):
                               (SEQ ID NO: 41)
GCTCAGAATCATTTAGCATAT TRCN0000099669 (targeting CDS):
                               (SEQ ID NO: 42)
GCGTTCAGACTGCACATAATA
```

The two control constructs are pLKO1puro empty vector (SHC001) and pLKO1puro Non-Mammalian shRNA Control (SHC002). Virus production, 4T1 cell infection and puromycin selection were carried out according to the manufacturer's instructions.

Microarray Gene Expression Analyses and Quantitative RT-PCR Assays.

Total RNA including small RNAs was isolated using RNeasy Mini Kit (Qiagen). The microarray hybridization was performed using the Illumina HumanHT-12 V4.0 expression beadchip, and data analysis was performed using GeneSpring software from Agilent Technologies. Microarray data reported herein have been deposited at the NCBI Gene Expression Omnibus with the accession number GSE36693. Reverse transcription and quantitative PCR assays were performed using High Capacity cDNA Archive kit and KAPA SyBr Fast qPCR kit (KAPA Biosystems), respectively. Taq-Man MicroRNA assays were used to quantify the level of mature miRNAs as previously described[8]. Briefly, 10 ng of total RNA was reverse-transcribed and product was subjected to TaqMan stemloop miRNA assay (Applied Biosystems). RNU6B was used to normalize the data. For quantification of mRNA levels, 18S level was used as internal control. All reactions were analyzed in an Applied Biosystems 7500 Fast. Real-Time PCR system in 96-well plate format. Real-time primer sequences are listed in Supplementary Table 2.

TABLE 1

Real-time primer sequences

| Gene | Forward primer (5' to 3') | Reverse primer (5' to 3') |
|---|---|---|
| UBASH3B | AGCCCGCGCACAAAAAGCCT (SEQ ID NO: 7) | CGGGGCAGGGGGTCATCCAG (SEQ ID NO: 8) |
| UBASH3A | CGGAGTCGTGGGATCAAAGA (SEQ ID NO: 9) | GCGTCCCCTGCAATTCTG (SEQ ID NO: 10) |

TABLE 1-continued

Real-time primer sequences

| Gene | Forward primer (5' to 3') | Reverse primer (5' to 3') |
|---|---|---|
| ETS1 | CCTCGGATTACTTCATTA GCTATGGTA (SEQ ID NO: 11) | TGGAGCGTCTGATA GGACTCTGT (SEQ ID NO: 12) |
| ACOT9 | TGGTGGATAAGATTGA TATGTGTAAGAAG (SEQ ID NO: 13) | TCCCGACCCAGCTAACATG (SEQ ID NO: 14) |
| CDK6 | GAGTGTTGGCTG CATATTTGCA (SEQ ID NO: 15) | GATCAACATCTGA ACTTCCACGAA (SEQ ID NO: 16) |
| HYAL3 | GGCCCCTATGTGATCAATGTG (SEQ ID NO: 17) | ATGGCACCGCTGGTGACT (SEQ ID NO: 18) |
| PSAT1 | AATGGAGGTGCCGCGGCCAT (SEQ ID NO: 19) | GCCCGGATGCCTCCCACAGAC (SEQ ID NO: 20) |
| B3GNT5 | AAGCCGACCTCCGA TTTGGACA (SEQ ID NO: 21) | CCTTCAGGAAGCGTG GTGGGC (SEQ ID NO: 22) |
| AGPAT4 | GTGTGGCTGGAGCCTGTCCG (SEQ ID NO: 23) | TCCTGCTCCCACTTGCGCGA (SEQ ID NO: 24) |

Western Blotting.

Western Blotting was performed as described previously[9]. Anti-UBASH3B (ab34781) was purchased from Abcam. Anti-EGFR (cs2232), anti-CBL (cs2747) and anti-Pan phosphor-Tyr (cs9411) was purchased from Cell Signaling. Anti-ETS1 (sc350), anti-ZEB1 (sc-2538.8), and anti-ZEB2 (sc-48789) were obtained from Santa Cruz. Anti-Myc and anti-Actin were purchased from Roche Applied Science and Sigma-Aldrich, respectively.

Co-Immunoprecipitation (Co-IP).

Co-IP was performed as described previously. 293T and BT549 whole cell lysate were extracted and subjected to immunoprecipitation using ProteinA/G agarose (Roche) according to the manufacturer's instructions. Anti-Myc, anti-Flag M2 affinity gel (#A2220, Sigma), or a non-specific IgG (sc-2025) was used in the co-IP assay.

Chromatin Immunoprecipitation (ChIP).

ChIP assays were performed as described previously[9]. Precleared chromatin from MDA-MB231 or BT549 cells was immunoprecipitated with anti-ETS1 (sc350). The immunoprecipitated DNA was quantitated by real-time quantitative PCR using KAPA SyBr Fast qPCR kit (KAPA Biosystems). The enrichment of specific genomic regions was assessed relative to the input DNA followed by normalization to the respective control IgG values. Primer sequences were listed in Table 2.

TABLE 2

Primer sequences

| Site | Forward primer (5' to 3') | Reverse primer (5' to 3') |
|---|---|---|
| P1 | AAGCGATTCTCCTGCCTTAGC (SEQ ID NO: 25) | GCATGGTGGCATGTGACTGT (SEQ ID NO: 26) |
| P2 | TCAAATCTTGGCTCTGCCATT (SEQ ID NO: 27) | TGAGCCAGAGGTCAAG TATCTTGT (SEQ ID NO: 28) |

TABLE 2-continued

Primer sequences

| Site | Forward primer (5' to 3') | Reverse primer (5' to 3') |
|---|---|---|
| P3 | TGTCTTATCTCCCTGCT TCCAAA (SEQ ID NO: 29) | GCCCGGAATTGGTTTCCT (SEQ ID NO: 30) |
| P4 | CGGTCCATACCAAT GAGGAAA (SEQ ID NO: 31) | CACTGCGGTGCC TTAGACAA (SEQ ID NO: 32) |
| P5 | CGGCTGATTGGGAACTCAA (SEQ ID NO: 33) | GATCCTGCAAAACCCAAAGG (SEQ ID NO: 34) |
| P6 | GCCCATAAGGTTGGGATCCT (SEQ ID NO: 35) | TGCGGGCAAGAGCTGTAGT (SEQ ID NO: 36) |
| P7 | CGGGAGCGTGGGTGTTC (SEQ ID NO: 37) | GCTTCTCCTTCTGATT CCATCCT (SEQ ID NO: 38) |
| P8 | TGCCTGTAATCC CAGCTACTTG (SEQ ID NO: 39) | CCTCCACCTA CTGGGCTCAA (SEQ ID NO: 40) |

Example 2

Functional Genomics Identifies the Overexpression of UBASH3B in TNBC

To identify novel targets associated with TNBC, the latest and most annotated Illumina HumanHT-12 V4.0 expression Beadchip was used to profile the gene expression of a panel of basal-like (often related to TNBC) and luminal type (non-TNBC) of human breast cancer cell lines and primary tumor tissues. To this end, a set of 103 genes were identified to be overexpressed in both TNBC cell lines and tissues compared to respective non-TNBC counterparts (FIG. 1(h) and Table 3 below). Among these genes shown in FIG. 1(a), 19 were annotated as enzymes and hence considered potential "druggable" targets. Moreover, seven of these genes show significant association with disease outcome in at least one examined breast cancer cohorts (FIG. 1(i)).

TABLE 3

103 genes overexpressed in both TNBC cell lines and tissues compared to respective non-TNBC counterparts

| ILMN_Gene | ILMN_Gene | ILMN_Gene | ILMN_Gene |
|---|---|---|---|
| TOX2 | AGPAT4 | ZRANB2 | SFRP1 |
| SMOX | ITM2C | LOC100132139 | FAM57A |
| CENPV | HS.571502 | SLC43A3 | HS.554507 |
| CD44 | APEG1 | SLC43A3 | FLJ13305 |
| CDC42BPA | MAPK12 | MPP6 | NXN |
| DCBLD1 | ADORA2B | LYN | ACTN1 |
| COTL1 | TM4SF1 | STS-1 | C11ORF41 |
| IL8 | SERPINE2 | UBASH3B | CCDC102A |
| MAP1B | UGP2 | WWTR1 | MICAL1 |
| MOXD1 | EGFR | B3GNT5 | CALD1 |
| CYP26B1 | GSTP1 | RASAL2 | PRMT2 |
| LOC643977 | PVRL3 | LOC100131541 | PRICKLE1 |
| ZCCHC6 | PIM1 | IGF2BP3 | HS.184721 |
| CD70 | ALDH1A3 | PRSS12 | LOC100132439 |
| PCOLCE2 | MFGE8 | TP53BP2 | HSD11B1L |
| LOC100132564 | PVRL3 | PELI1 | HOMER3 |
| SNORD3D | ACOT9 | FOXC1 | NPAT |
| SNORD3A | CDK6 | FAM171A1 | CPA4 |
| SNORD3C | HEATR1 | SERPINB7 | ARHGAP22 |
| WNT5B | CDC42EP1 | SERPINB7 | HYAL3 |

TABLE 3-continued 103 genes overexpressed in both TNBC cell lines
and tissues compared to respective non-TNBC counterparts

| ILMN_Gene | ILMN_Gene | ILMN_Gene | ILMN_Gene |
|---|---|---|---|
| FXYD5 | SLC25A37 | EN1 | CDC20 |
| FXYD5 | DLL3 | FSCN1 | LBR |
| TMEM158 | GPR161 | CHST3 | PSAT1 |
| AHNAK2 | RGS20 | PLOD1 | LOC729779 |
| C14ORF78 | ST3GAL6 | LOC346887 | SNORA77 |
| TIAM2 | IGF2BP2 | AK2 | |

To address whether the above genes could have roles in TNBC, their expressions were knocked down individually in a highly aggressive breast cancer cell line MDA-MB-231 (hereafter named MB231) cells by transfecting two independent small interference RNA oligos (siRNAs). The efficiencies of the gene knockdown were monitored by quantitative RT-PCR and the phenotypic changes were assessed on the 3-dimensional (3D) Matrigel growth as an indicator of malignant growth. The results showed that 5 out of 7 these genes (UBASH3B, AGPAT4, ACOT9, CDK6, and HYAL3) may be required for TNBC progression as their knockdown strongly reduced the Matrigel growth of MB231 cells (FIG. 1(b)). Among them, UBASH3B, also called Suppressor of T-cell receptor signaling 1 (STS-1), was of particular interest for further study as it was top-rated in phenotypic change and also previously known to regulate EGFR endocytosis and degradation[10]. Moreover, it has been recently shown to have a tyrosine protein phosphatase activity[11]. However, a role of UBASH3B in tumorigenesis has not been described to date.

Further validation analysis using quantitative RT-PCR and Western blotting showed a high amount of UBASH3B mRNA and protein in highly invasive TNBC cell lines compared to the less invasive luminal lines (FIG. 1(c)). In contrast, UBASH3A, a close family member of UBASH3B, did not show such a difference (FIG. 1(j)). Interestingly, UBASH3B was also overexpressed in invasive prostate cancer cells (FIG. 1(k)). Furthermore, gene expression analysis based on Oncomine datasets likewise showed the overexpression, of UBASH3B in TNBC and metastatic prostate cancer specimens (FIG. 1(d) and FIG. 1(l)). The overexpression of UBASH3B in TNBC was further verified by immunohistochemistry (IHC) analysis of clinical tumor specimens (P=0.018) (FIG. 1(e)). Furthermore, an IHC analysis of a cohort of primary and invasive breast tumors on a tissue microarray revealed that UBASH3B expression was higher in invasive breast cancer compared to non-invasive counterparts (P=0.0155) (FIG. 1(f)). Lastly, in a clinical cohort that contains data for organ-specific metastasis-free survival (GSE12276), expression of UBASH3B was found to be positively associated with poor survival of patients with lung or brain metastasis, though not associated with bone metastasis (FIG. 1(g)). Taken together, these findings suggest a potential role of UBASH3B in the progression of tumor cell invasion and metastasis.

UBASH3B is a Transcriptional Target of ETS1

Figure 2:
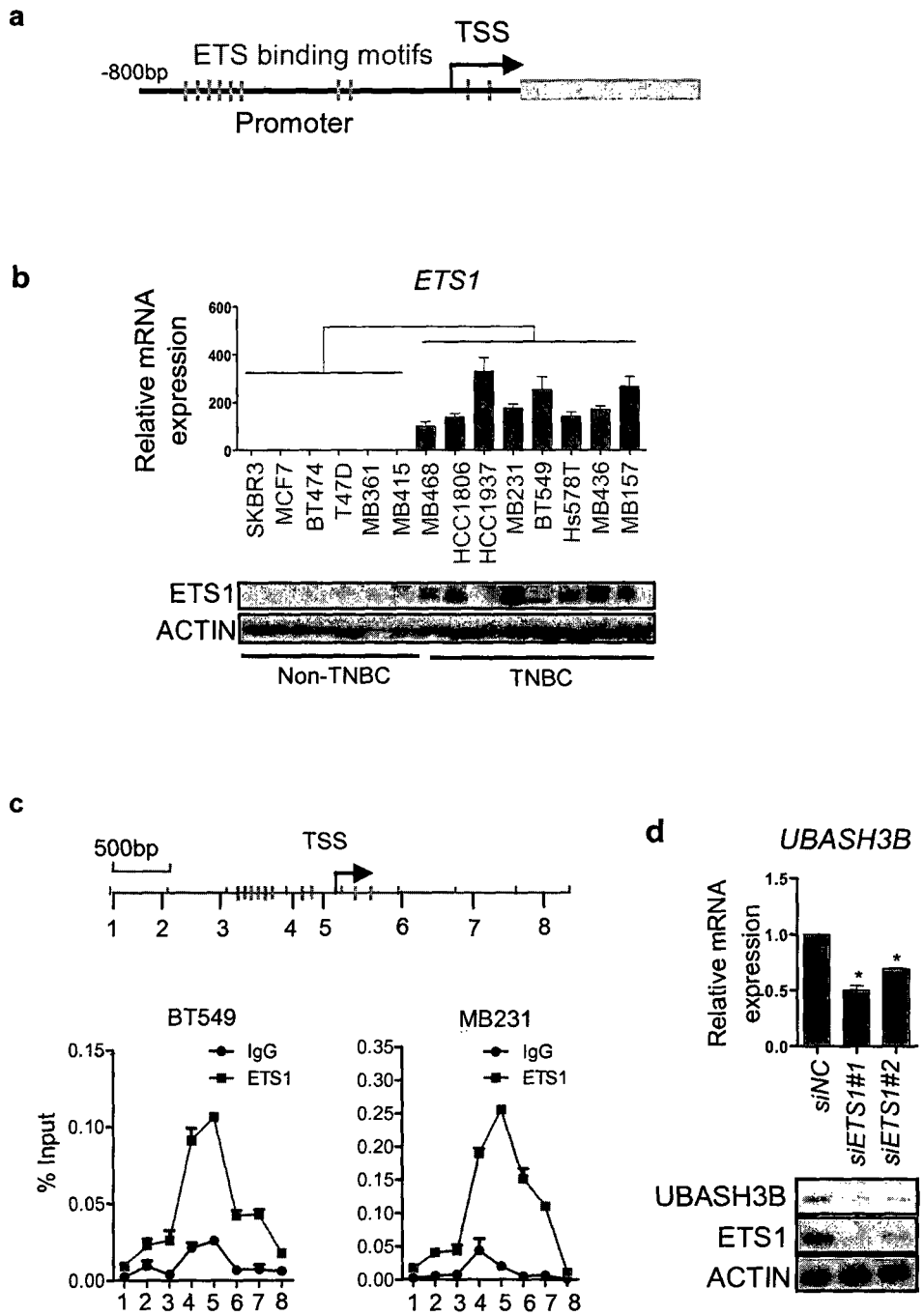
FIG. 2 Shows that UBASH3B is a Transcriptional Target of ETS1

To identify the molecular events leading to UBASH3B upregulation associated with invasion, the potential transcription factor binding sites at the promoter region of UBASH3B were analyzed. Of note, multiple putative binding sequences of ETS family were found to be enriched in the proximal promoter of UBASH3B (FIG. 2(a)). Among ETS family members, ETS1 is known to be an invasive factor associated with aggressive tumors[12]. Echoing the UBASH3B expression, ETS1 was also overexpressed in invasive breast cancer cell lines and clinical tumor samples but not in non-invasive counterparts (FIG. 2(b) and FIGS. 2(h) and 2(i)). Chromatin immunoprecipitation (ChIP) analysis showed a remarkable enrichment of ETS1 in the UBASH3B core promoter in TNBC MB231 and BT549 cells (FIG. 2(c)), supporting a direct regulation of UBASH3B by ETS1. ETS1 knockdown resulted in downregulation of UBASH3B expression in invasive breast cancer BT549 as well as prostate cancer DU145 and PC3 cells (FIG. 2(d) and FIG. 2(j)). Furthermore, as ETS1 transcriptional activity requires MAPK[13], MAPK inhibitor U0126 treatment in MB231 cells was seen to decrease the UBASH3B expression in a time-dependent manner (FIG. 2(e)). Importantly, ETS1 and UBASH3B expression seemed to be correlated well in clinical breast tumor samples in general (FIG. 2(f), left), and also co-upregulated in organ-specific metastases (FIG. 2(f), right). Similar to UBASH3B, ETS1 expression is also associated with lung and brain but not bone metastasis in the same GSE12276 cohort (FIG. 2(g)), verifying a clinical relevance of ETS1-UBASH3B regulation.

UBASH3B is Also a Target of miR-200a

Figure 3:
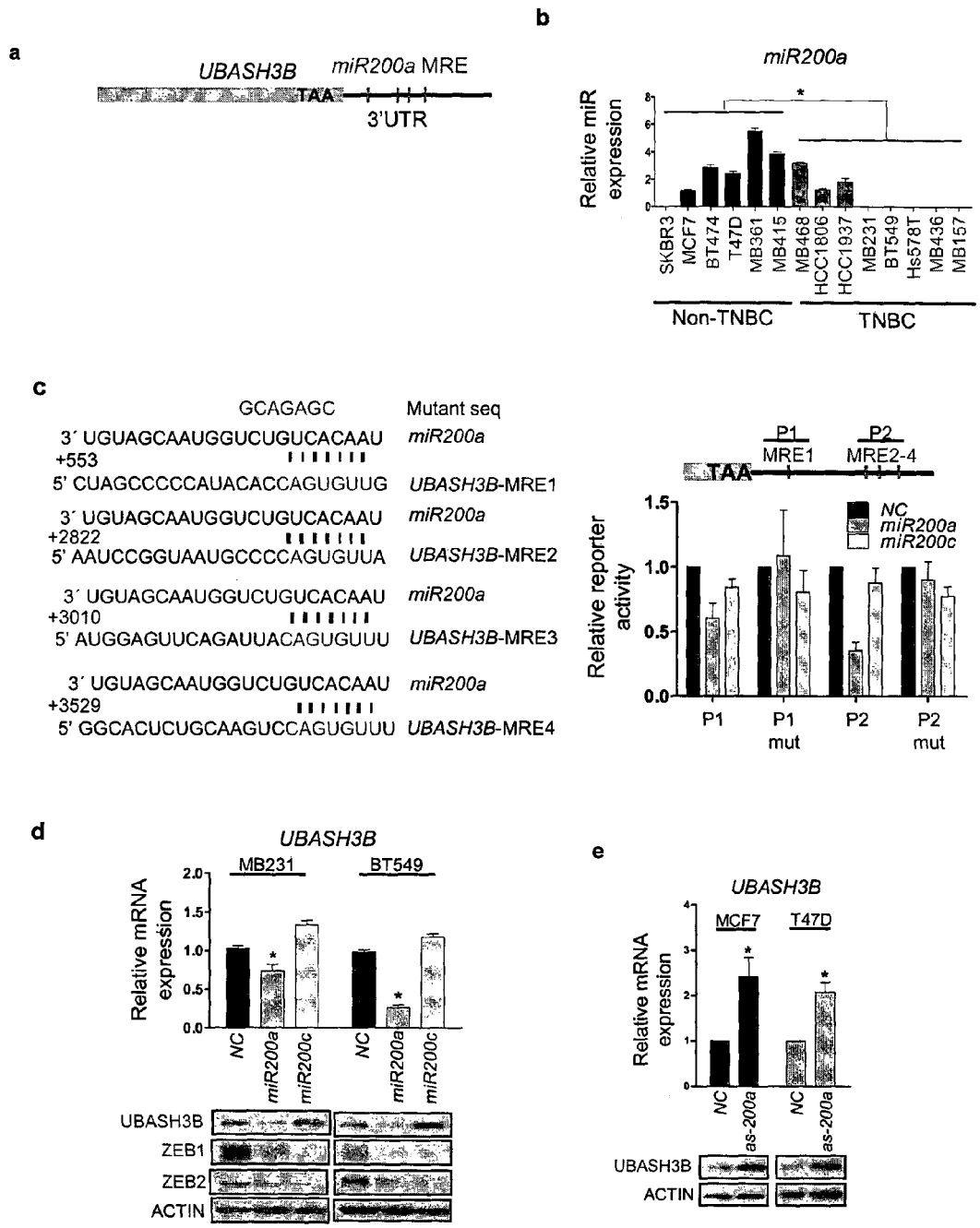
FIG. 3 Shows that UBASH3B is a Target of miR200a, and MiR200s are Associated with Non-TNBC Status but Only miR200a Regulates UBASH3B Expression

Interestingly, when the regulatory-regions of UBASH3B were further examined, several miR-200a target sequences were seen to be present in the 3'-untranslated region (3'-UTR) of UBASH3B (FIG. 3 (a)). MiR-200s are known to be anti-invasive and their expression are downregulated in aggressive breast cancer and prostate cancer[14-15]. Next, the possibility of UBASH3B being a target of miR-200s was investigated. RT-PCR analysis showed the downregulation of miR200a/b/c in mesenchymal TNBC cell lines (FIG. 3(b) and FIG. 3(g)), which was further confirmed in primary TNBC tumors (FIG. 3(h)). Consistent with the above analysis that UBASH3B 3' UTR contains sites for miR-200a, but not for miR-200b/c, a direct and specific targeting and inhibition of UBASH3B by miR-200a, but not by miR-200c, was demonstrated using UBASH3B 3'-UTR reporters that contains the wild type or a variant in which the miR-200a binding sequences were mutated (FIG. 3(c)). As expected, enforced expression of miR-200a, but not miR-200c, was able to reduce the UBASH3B mRNA and protein expression in invasive breast and prostate cancer cells (FIG. 3(d) and FIG. 3(i)), though both miR-200a and miR-200c could repress the expression of ZEB1 and ZEB2 (FIG. 3(d)), two common targets of miR-200a/b/c[16-17]. Conversely, miR-200a antagomir treatment of MCF7 and T47D cells that express high levels of miR-200a resulted in upregulation of UBASH3B mRNA and protein levels (FIG. 3(e)). Furthermore, a combination of ETS1 knockdown and miR-200a overexpression in BT549 cells resulted in more pronounced downregulation of UBASH3B (FIG. 3(f)). Therefore, these findings indicate that UBASH3B is a target of both ETS1 and mir-200a whose deregulation collectively contributes to the UBASH3B upregulation in invasive cancers.

UBASH3B Knockdown Reduces Malignancy In Vitro Through Decreasing EGFR

The relevance of UBASH3B overexpression in tumorigenesis was next assessed. As UBASH3B is implicated in antagonizing EGFR degradation during endocytosis upon EGF treatment[10], whether UBASH3B has a role in EGF-induced invasion, a process of particular relevance in TNBC, was investigated. UBASH3B knockdown by two independent siRNAs accentuated EGFR protein degradation and resulted in marked inhibition of EGF-induced transwell invasion in invasive breast and prostate cancer cells (FIG. 4(a) and FIG. 4(h)). This observation is consistent with known role of EGFR as a well-established invasive effector in TNBC and other invasive tumors[18-20]. The specificity of knockdown effects on invasion was further confirmed by a rescue experiment using ectopic expression of UBASH3B and the third siRNA targeting the 3'-UTR of UBASH3B (FIG. 4(i)). Conversely, ectopic UBASH3B overexpression was able to induce EGFR protein expression in non-cancerous human mammary epithelial MCF10A cells, though UBASH2B alone was insufficient to induce an invasive phenotype in this cell line (FIG. 4(j) and data not shown). The positive correlation between UBASH3B and EGFR in primary breast tumors was further validated by IHC analysis of 73 patients tissues, showing that patients with higher EGFR expression were significantly enriched with higher UBASH3B expression (P=0.034) (FIG. 4(b)).

Figure 4:
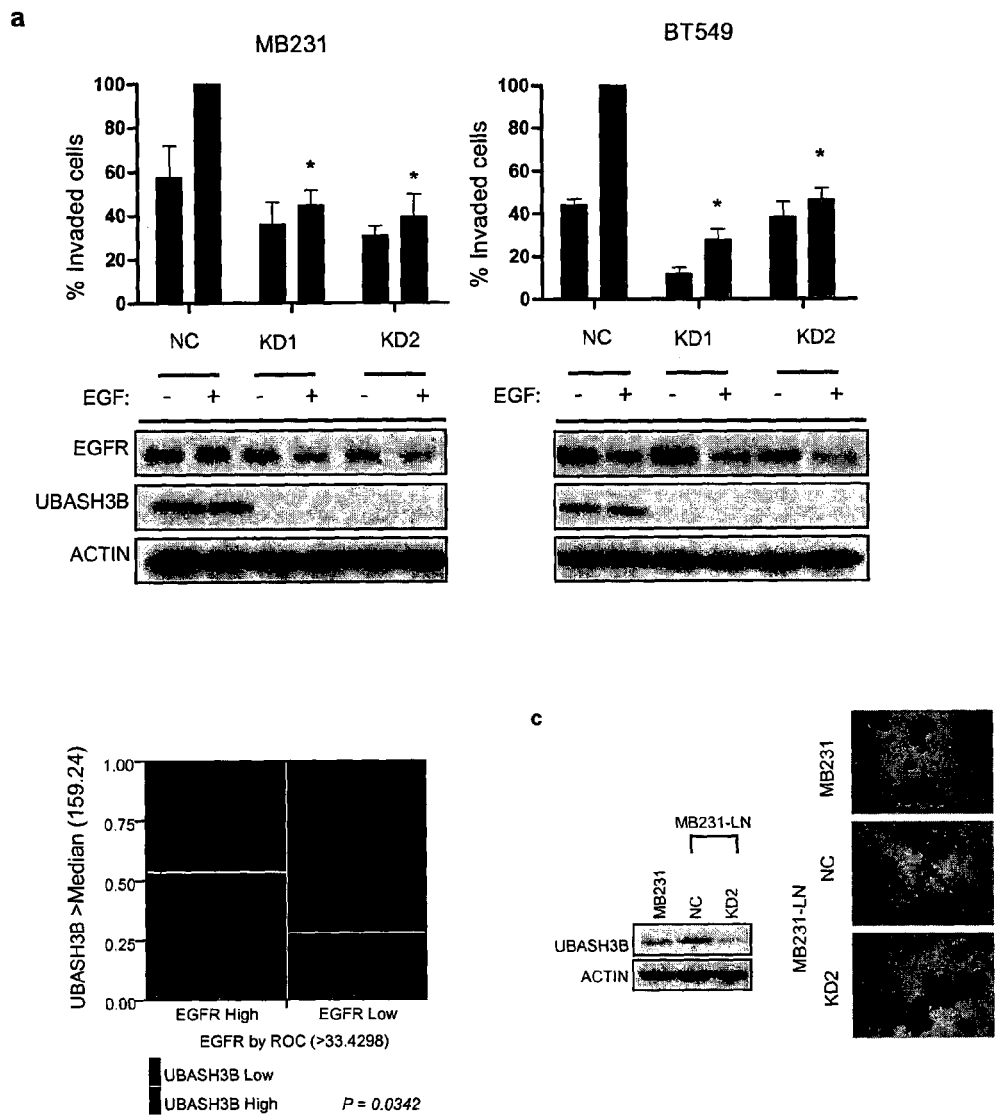
FIG. 4 Shows UBASH3B Knockdown Reduces Malignancy and Therapeutic Response to Erlotinib, and UBASH3B Depletion Reduces Cancer Cell Aggressiveness

In addition to affecting cell invasion, UBASH3B knockdown also reduced the ability of breast and prostate cancer cells to form tumorspheres (FIGS. 4(k) and 4(l)), a growth feature associated with cancer stem cells, while, notably, UBASH3B knockdown did not affect cell proliferation when grown on monolayer (FIG. 4 (m)). This indicates that UBASH3B is not required for cell proliferation in general but more involved in regulating cellular phenotypes associated with malignancy. Consistent with these observations, it was found that UBASH3B expression is further upregulated in a more metastatic subline of MB231 (LN)[21], which displayed a more aggressive morphology compared to the parental cells in 3D Matrigel growth condition (FIG. 4(c)). As expected, UBASH3B knockdown in MB231-LN cells attenuated the aggressive morphology (FIG. 4(c)).

To interrogate whether the phenotypic changes following UBASH3B knockdown is due to the reduction of EGFR protein, rescue assay was performed by stably ectopic expression of EGFR in MB231 cells depleted of UBASH3B. It was observed that the ectopic EGFR overexpression largely restored the invasive capacity of UBASH3B depleted cells (FIG. 4(d) and FIGS. 4(n) and 4(o)), consistent with the inventors' hypothesis that UBASH3B drives invasion through EGFR at least in large part.

UBASH3B Modulates Therapeutic Responses to Erlotinib and Paclitaxel

Although EGFR is known to be overexpressed in TNBC, anti-EGFR therapy has at most 7% response rate. Given a role of UBASH3B in modulating EGFR, the inventors next investigated whether or not UBASH3B expression has a role in modulating therapeutic effect of EGFR inhibitor Erlotinib. Clearly, through assessment of anchorage-independent growth using methylcellulose assay, it was observed that UBASH3B depletion rendered MB231-LN to be less sensitive to Erlotinib by increasing the EC50 from 0.45 µM to 3.85 µM (FIG. 4(e)). This in vitro effect was further validated in vivo using MB231-LN xenograft tumor growth in mice. Consistently, UBASH3B depleted tumors appeared to be irresponsive to Erlotinib treatment while the control tumors showed marked growth inhibition following the treatment (FIG. 4(f)). This implicates that the presence of high level of UBASH3B could be required for effective TNBC response to the EGFR inhibitor. Importantly, ectopic overexpression of EGFR in UBASH3B-depleted MB231 restored the sensitivity of the cells to Erlotinib treatment (FIG. 4(g)), further validating that the resistance towards Erlotinib caused by UBASH3B knockdown was due to EGFR reduction.

TNBC tends to have early recurrence presented with distant metastasis after adjuvant chemotherapy. Given a recent breakthrough report showing that anti-EGFR treatment in TNBC could enhance the response to chemotherapy[22], it would be interesting to examine whether UBASH3B depletion could also sensitize TNBC cells towards Paclitaxel, a chemotherapeutic agent mainly used for metastatic TNBC. The result shows that depletion of UBASH3B significantly increased the sensitivity of MB231 towards Paclitaxel, by reducing EC50 from 4.53 nM to 0.61 nM (FIG. 5(l)). Moreover, in a TNBC cell line SUM159PT that has acquired resistance to Paclitaxel, it was found that expression of UBASH3B was substantially upregulated as compared to the parental cells (FIG. 5(m)). Accordingly, UBASH3B knockdown in this resistant cell line resulted in increased sensitivity to Paclitaxel treatment (FIG. 5(n)). These findings taken together indicate a potential role of UBASH3B in modulating Paclitaxel sensitivity in TNBC.

UBASH3B Knockdown Reduces Breast Cancer Metastasis In Vivo

Figure 5:
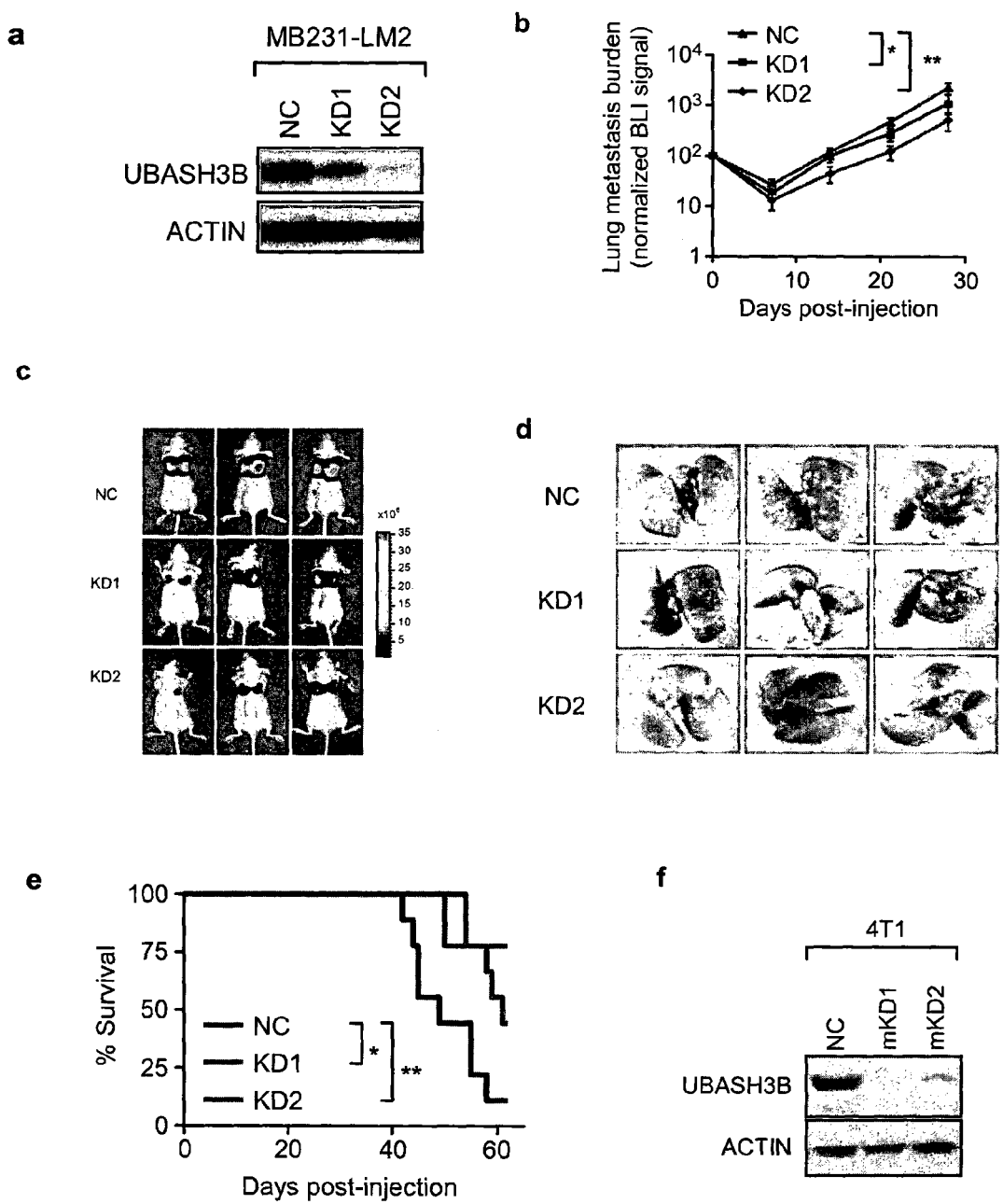
FIG. 5 Shows that UBASH3B Knockdown Reduces Breast Cancer Metastasis, and UBASH3B Depletion Sensitizes TNBC Cells to Paclitaxel.

To determine whether UBASH3B is required for tumor metastasis, the inventors made use of a lung metastatic MB231 subline (LM2)[23] that expresses luciferase reporter and generated shNC and shUBASH3B#1 (KD1) and shUBASH3B#2 (KD2) stable lines (FIG. 5(a)). Tail vein injection of these cells resulted in lung metastasis in nude mice. BLI measurement revealed significant lung metastasis reduction by KD cells comparing to control, with 50% and 77% reduction of metastasis burden at week 4 after injection by KD1 and KD2, respectively (FIG. 5(b)-(d)), which corresponded well to the respective knockdown efficiency in these cells. The reduction of metastasis is consequently converted to substantial survival advantages in these mice. As shown in FIG. 5(e), knockdown of UBASH3B substantially reduces the risk of mortality in mice by 3.51 (95% CI=1.10-11.18) and 6.99 (95% CI=1.46-33.50) folds by KD1 and KD2, respectively. This significantly prolonged survival of the mice (p=0.02 and 0.004 for KD1 and KD2, respectively) (FIG. 5(e)). To further test the generality of the pro-metastatic function of UBASH3B in an immunocompetent and spontaneous metastasis model, the inventors also knocked down UBASH3B in the 4T1 mouse mammary tumor cell line and tested the effects in both experimental and spontaneous metastasis models by tail vein and mammary gland injection, respectively. In both models, UBASH3B knockdown strongly inhibited the lung metastasis (FIG. 5(f)-(j)). Moreover, using MB231-LN lung metastasis model, the inventors demonstrates that ecotopic expression of EGFR partially rescued inhibited metastasis in UBASH3B-depleted cells, though this rescue was only seen in the later weeks of metastasis progression (FIG. 5(k)). These data from both in vitro and in vivo studies demonstrate a key role of UBASH3B, at least in part through EGFR, in the progression of tumor cell invasion and metastasis.

Figure 6:
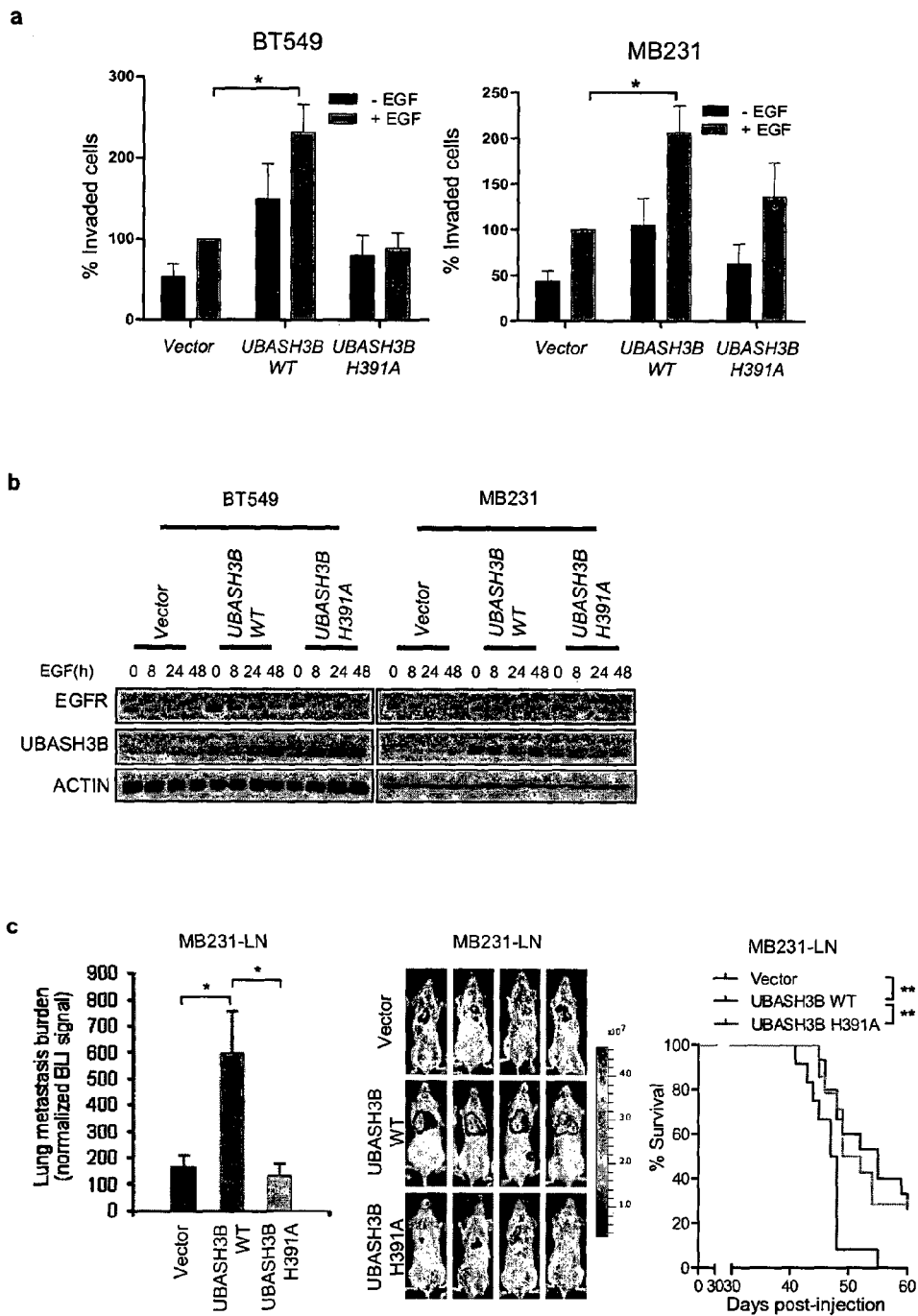
FIG. 6 Shows that the Oncogenic Role of UBASH3B Requires Phosphatase Activity Targeting CBL Phosphorylation and EGFR Degradation

Oncogenic Role of UBASH3B Requires Phosphatase Activity Targeting CBL Phosphorylation and EGFR Degradation As UBASH3B has been recently shown to be a tyrosine phosphatase[11], the inventors explored whether the phosphatase activity is required for its invasion-promoting capacity. To achieve this, a phosphatase-dead mutant UBASH3B (H391A)[11] was made and compared with the wild type UBASH3B for their abilities to promote cell invasion. While the overexpression of wild type UBASH3B in BT549 and MB231 cells promoted both basal and EGF-induced invasion robustly, UBASH3B (H391A) failed to do so (FIG. 6(a)). Consistently, EGF-induced EGFR degradation over time was rescued by ectopic overexpression of wild type UBASH3B, but not UBASH3B (H391A) (FIG. 6(b)). This observation was validated in vivo by conducting lung colonization assay by tail-vein injection of MB231-LN cells stably expression wild type UBASH3B and UBASH3B (H391A). Consistent with in vitro data, wild type UBASH3B but not the mutant UBASH3B lacking the phosphatase activity could enhance lung metastasis and concurrently reduce mice survival (FIG.

6(c)). These results suggest that the phosphatase activity of UBASH3B is required for its capability to promote invasion, Matrigel growth and EGFR protein abundance.

It has been previously shown that UBASH3B promotes EGFR protein stability through binding to and inhibiting CBL ubiquitin ligase-mediated EGFR degradation[10]. However, it is unknown whether this UBASH3B inhibition of CBL is mediated by its tyrosine phosphatase activity through dephosphorylating CBL. The inventors found that overexpression of the wild type UBASH3B, but not the UBASH3B H391A, resulted in loss of EGF-induced tyrosine phosphorylation of ectopic CBL in HEK293T cells, as assessed by probing the immunoprecipitated CBL with a Pan-phosphotyrosine antibody, although interaction was observed between both wild type and mutant UBASH3B with CBL (FIG. 6(d)). Moreover, in BT549 cells, EGF failed to induce CBL phosphorylation upon overexpression of wild type UBASH3B, but induced robust CBL phosphorylation in the presence of UBASH3B (H391A) mutant (FIG. 6(e)). The inventors further showed that UBASH3B knockdown-induced EGFR degradation could be restored by the concomitant CBL knockdown (FIG. 6(f)), indicating an antagonistic role of CBL in promoting UBASH3B-induced EGFR stabilization. Taken together, the data support the hypothesis that UBASH3B promotes invasion and aggressive growth by promoting EGFR stability through dephosphorylation and inhibition of CBL function. Hence, the oncogenic phosphatase activity of UBASH3B allows it to emerge as an excellent new therapeutic target for cancer invasion and metastasis.

Based on these studies, the inventors proposed a model for a role of UBASH3B tyrosine phosphatase in promoting breast cancer metastatic behavior through modulating CBL-EGFR. These findings suggest that UBASH3B does not act as an isolated factor but as an integral node that connects various pro-invasive mechanisms into a tightly regulated network (FIG. 6(g)). ETS1 and miR200a, collaboratively results in the overexpression of UBASH3B in invasive breast cancer cells. UBASH3B in turns dephosphorylates CBL and lead to the stabilization of EGFR expression and subsequent aggressive phenotypes.

DISCUSSION

Unlike ER or HER2 positive breast tumors, there are no targeted therapies for TNBC. Given the high genetic heterogeneity of TNBC and complex gene network in driving malignancy, together with limited benefits of current targeted therapies, continued efforts to identify novel enzymes that represent crucial nodal points of control network for pharmacological intervention are of particular relevant. Given the inventors' observation of UBASH3B overexpression in TNBC and its fundamental role as a tyrosine phosphatase in invasive progression and disease outcome, the inventors contend that UBASH3B overexpression is an important oncogenic event in TNBC. Importantly, UBASH3B acts to bridge several key invasive pathways, raising a possibility that therapeutic targeting UBASH3B may provide additional benefits for TNBC patients.

UBASH3B upregulation in TNBC can be the result of deregulation of ETS1 and miR-200a, two key molecules whose functions are often associated with cancer invasion. The inventors showed UBASH3B is a direct target of both ETS1 and miR-200a and thus upregulation of UBASH3B could be a combined result of ETS1 overexpression and miR-200a downregulation in TNBC. Although members of miR-200s can suppress EMT by repressing the expression of ZEB1/2 thereby facilitating the spreading of cancer cells[16], UBASH3B does not seem to affect EMT as its knockdown neither change cell morphology nor the expression of EMT markers such as E-cadherin and Vimentin (data not shown) Therefore, UBASH3B may coordinate with other miR-200 targets to promote invasive capacity to enable extravasation and subsequent migration to distal sites. It has been shown that when circulating cancer cells colonize a distal site for instance lung, miR-200 needs to be re-expressed to induce mesenchymal-to-epithelial transition (MET), a rate-limiting step to allow attachment and colonization of the new, niche[24]. Thus, UBASH3B expression may not be required during that late stages of metastasis progression, its role in after metastasis colonization may need further investigations.

One unique aspect of this study is that the inventors showed UBASH3B functions as an oncogenic protein tyrosine phosphatase. This appeared to be counterintuitive as it has been previously shown that TNBC harbors an overall induction of protein tyrosine phosphorylation activity due to activation of a number of receptor tyrosine kinases such as EGFR and MET as well as non receptor tyrosine kinases Src[25]. Moreover, other protein phosphatases such as PTEN and PTPN12 often function as tumor suppressors that are inactivated in TNBC[26-27]. Therefore, it is conceivable that UBASH3B as a tyrosine phosphatase may most likely exert its oncogenic function by selectively targeting a specific tumor suppressive tyrosine phosphorylation event. One such an example is tyrosine phosphatase PTP1B that has been shown to be oncogenic through inhibiting the growth inhibitory Src Y530 phosphophorylaton in prostate and colon cancers[28]. Of notice, a recent study has implicated another tyrosine phosphatases SHP2 in breast cancer progression[29], though its association with TNBC as well as the direct targets for dephosphorylation are yet to be elucidated.

One possible mechanism by which UBASH3B promotes invasive growth and metastasis in TNBC is at least partially through CBL-mediated EGFR regulation. The inventors showed that UBASH3B directly targets CBL phosphorylation to promote EGFR stability. CBL is long known to have dual roles in oncogenesis, one of which is the tumor suppressive function whereby CBL acts as an ubiquitin ligase to degrade multiple oncogenic tyrosine kinases including EGFR[30], while its oncogenic role has been linked to its ability to be recruited to activated receptors and served as adaptor for the docking of downstream kinases cascade to relay the oncogenic signaling[31]. The tumor suppressive ubiquitin ligase activity is associated with the phosphorylation at tyrosine residue 371, though other phosphorylation sites have been linked to its oncogenic activity[32]. The inventors showed that UBASH3B is able to bind to and dephosphorylate CBL using a pan-tyrosine phosphorylation antiobody, leading to EGFR stabilization. It will be interesting to investigate in the future whether UBASH3B specifically targets Y371 or other phosphorylation sites. Although it is possible that UBASH3B may have effects on both tumor suppressive and oncogenic phosphorylation sites, it may preferentially modulate CBL towards the oncogenic activity when it is overexpressed in aggressive cancers like TNBC.

By inhibiting UBASH3B phosphatase activity, EGFR protein level was reduced due to the increase ubiquitin ligase activity of CBL. EGFR is known to be overexpressed in TNBC, though EGFR-based therapy alone in TNBC has failed to show an expected response. The inventors have shown that depletion of UBASH3B has phenocopied EGFR inhibitor Erlotinib treatment in vivo (FIG. 4(f)). Moreover, xenograft tumors depleted of UBASH3B were no longer sensitive to Erlotinib treatment. Thus, UBASH3B level might be an important determinant of EGFR inhibitor response in TNBC. The inventors postulate that TNBC patients with both high EGFR and UBASH3B levels might be more responsive to therapeutic targeting of EGFR. Furthermore, targeting EGFR in combination with chemotherapy has shown benefits to TNBC patients in a recent clinical trial[22]. When TNBC cells were treated with a chemotherapy drug, Paclitaxel, it showed sensitization in the cell line with UBASH3B depleted. This supports the notion that targeting UBASH3B could be an alternative approach to EGFR inhibition, especially in the cases when the cells develop resistance to EGFR inhibitors.

The preferential regulation of UBASH3B on aggressive tumor behaviors such as invasion, metastasis and tumor-sphere formation, but not cell proliferation, suggests that therapeutic targeting of UBASHB may provide cancer selectivity and safety, making it an attractive approach for cancer therapy.

APPLICATIONS

Development of new and more effective therapies against more invasive types of cancer which may have more tendency to metastasize, such as breast, colon and prostate cancers, is particularly important due to the escalating number of new cancer cases worldwide. Limited or no effective targeted therapeutics against such cancers is currently available.

The disclosed modulator compounds and compositions thereof may be used in the disclosed methods to treat cancer, particularly to reduce cancer invasiveness and metastasis, by modulating expression of the UBASH3B gene, and/or the activity of the UBASH3B protein or a functional variant thereof. The disclosed modulator compounds and compositions thereof may also be used to sensitize or re-sensitize a cancer patient to a treatment with one or more chemotherapeutic agents, by modulating expression of the UBASH3B gene, and/or the activity of the UBASH3B protein or a functional variant thereof. Also disclosed are methods that may be used to predict disease outcome, aid selection of a suitable treatment for a cancer patient, and optimize the treatment regimen.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

REFERENCES

1. Bos, P. D., et al. Genes that mediate breast cancer metastasis to the brain. *Nature* 459, 1005-1009 (2009)
2. Pawitan, Y., et al. Gene expression profiling spares early breast cancer patients from adjuvant therapy: derived and validated in two population-based cohorts. *Breast cancer research: BCR* 7, R953-964 (2005)
3. Wang, Y., et al. Gene-expression profiles to predict distant metastasis of lymph-node-negative primary breast cancer. *Lancet* 365, 671-679 (2005)
4. Korpal, M., et al. Direct targeting of Sec23a by miR-200s influences cancer cell secretome and promotes metastatic colonization. *Nature medicine* 17, 1101-1108 (2011)
5. Lu, X., et al. VCAM-1 promotes osteolytic expansion of indolent bone micrometastasis of breast cancer by engaging alpha4beta1-positive osteoclast progenitors. *Cancer cell* 20, 701-714 (2011)
6. Nguyen, T., et al. Downregulation of microRNA-29c is associated with hypermethylation of tumor-related genes and disease outcome in cutaneous melanoma. *Epigenetics: official journal of the DNA Methylation Society* 6, 388-394 (2011)
7. Zhang, Y., et al. miR-125b is methylated and functions as a tumor suppressor by regulating the ETS1 proto-oncogene in human invasive breast cancer. *Cancer research* 71, 3552-3562 (2011)
8. Feng, M., et al. Myc/miR-378/TOB2/cyclin D1 functional module regulates oncogenic transformation. *Oncogene* 30, 2242-2251 (2011)
9. Lee, S. T., et al. Context-specific regulation of NF-kappaB target gene expression by EZH2 in breast cancers. *Molecular cell* 43, 798-810 (2011)
10. Kowanetz, K., et al. Suppressors of T-cell receptor signaling Sts-1 and Sts-2 bind to Cbl and inhibit endocytosis of receptor tyrosine kinases. *The Journal of biological chemistry* 279, 32786-32795 (2004)
11. Mikhailik, A., et al. A phosphatase activity of Sts-1 contributes to the suppression of TCR signaling. *Molecular cell* 27, 486-497 (2007)
12. Hahne, J. C., et al. Ets-1 expression promotes epithelial cell transformation by inducing migration, invasion and anchorage-independent growth. *Oncogene* 24, 5384-5388 (2005)
13. Hollenhorst, P. C., et al. Oncogenic ETS proteins mimic activated RAS/MAPK signaling in prostate cells. *Genes & development* 25, 2147-2157 (2011)
14. Cao, Q., et al. Coordinated regulation of polycomb group complexes through microRNAs in cancer. *Cancer cell* 20, 187-199 (2011)
15. Iliopoulos, D., et al. Loss of miR-200 inhibition of Suz12 leads to polycomb-mediated repression required for the formation and maintenance of cancer stem cells. *Molecular cell* 39, 761-772 (2010)
16. Gregory, P. A., et al. The miR-200 family and miR-205 regulate epithelial to mesenchymal transition by targeting ZEB1 and SIP1. *Nature cell biology* 10, 593-601 (2008)
17. Korpal, M., Lee, E. S., Hu, G. & Kang, Y. The miR-200 family inhibits epithelial-mesenchymal transition and cancer cell migration by direct targeting of E-cadherin transcriptional repressors ZEB1 and ZEB2. *The Journal of biological chemistry* 283, 14910-14914 (2008)
18. Foley, J., et al. EGFR signaling in breast cancer: bad to the bone. *Seminars in cell & developmental biology* 21, 951-960 (2010)
19. Mitsudomi, T. & Yatabe, Y. Epidermal growth factor receptor in relation to tumor development: EGFR gene and cancer. *The FEBS journal* 277, 301-308 (2010)
20. Morishige, M., et al. GEP100 links epidermal growth factor receptor signalling to Arf6 activation to induce breast cancer invasion. *Nature cell biology* 10, 85-92 (2008)
21. Jenkins, D. E., Hornig, Y. S., Oei, Y., Dusich, J. & Purchio, T. Bioluminescent human breast cancer cell lines that permit rapid and sensitive in vivo detection of mammary tumors and multiple metastases in immune deficient mice. *Breast cancer research: BCR* 7, R444-454 (2005)
22. Baselga J, G. P., Awada A, et al. The addition of cetuximab to cisplatin increases overall response rate and progression-free survival in metastatic triple-negative breast cancer: Results of a randomized phase II study. 35*th ESMO Congress*. Abstract 2740. (Presented Oct. 11, 2010.)
23. Minn, A. J., et al. Genes that mediate breast cancer metastasis to lung. *Nature* 436, 518-524 (2005)
24. Korpal, M., et al. Direct targeting of Sec23a by miR-200s influences cancer cell secretome and promotes metastatic colonization. *Nature medicine* 17, 1101-1108 (2011)

25. Hochgrafe, F., et al. Tyrosine phosphorylation profiling reveals the signaling network characteristics of Basal breast cancer cells. *Cancer research* 70, 9391-9401 (2010)
26. Marty, B., et al. Frequent PTEN genomic alterations and activated phosphatidylinositol 3-kinase pathway in basal-like breast cancer cells. *Breast cancer research BCR* 10, R101 (2008)
27. Sun, T., et al. Activation of multiple proto-oncogenic tyrosine kinases in breast cancer via loss of the PTPN12 phosphatase. *Cell* 144, 703-718 (2011)
28. Bjorge, J. D., Pang, A. & Fujita, D. J. Identification of protein-tyrosine phosphatase 1B as the major tyrosine phosphatase activity capable of dephosphorylating and activating c-Src in several human breast cancer cell lines. *The Journal of biological chemistry* 275, 41439-41446 (2000)
29. Aceto, N., et al. Tyrosine phosphatase SHP2 promotes breast cancer progression and maintains tumor-initiating cells via activation of key transcription factors and a positive feedback signaling loop. *Nature medicine* (2012)
30. Joazeiro, C. A., et al. The tyrosine kinase negative regulator c-Cbl as a RING-type, E2-dependent ubiquitin-protein ligase. *Science* 286, 309-312 (1999).
31. Thien, C. B. & Langdon, W. Y. Cbl: many adaptations to regulate protein tyrosine kinases. *Nature reviews. Molecular cell-biology* 2, 294-307 (2001)
32. Levkowitz, G., et al. Ubiquitin ligase activity and tyrosine phosphorylation underlie suppression of growth factor signaling by c-Cbl/Sli-1. *Molecular cell* 4, 1029-1040 (1999)

The invention claimed is:

1. A method of treating cancer comprising administering an ubiquitin associated and SH3 domain containing B (UBASH3B) antagonist oligonucleotide to a cancer patient, wherein said UBASH3B antagonist oligonucleotide is selected from the group consisting of an UBASH3B shRNA comprising a sequence selected from the group consisting of 5'-GCTCAGAATCATTTAGCATAT-3' (SEQ ID NO: 41) and 5'-GCGTTCAGACTGCACATAATA-3' (SEQ ID NO: 42) and an UBASH3B siRNA comprising a sequence selected from the group consisting of 5'-CCGGCUUAUUUGAGUGGAC-3' (SEQ ID NO: 1), 5'-CCUCAUAAGAAGCAGCUAC-3' (SEQ ID NO: 2), and 5'-GCACUGCAACUGAGAAAUU-3' (SEQ ID NO: 3), and wherein said cancer is selected from the group consisting of breast cancer, prostate cancer, lung cancer and brain cancer.

2. The method of claim 1, wherein the treatment comprises preventing cancer invasion and/or metastasis.

3. The method of claim 1, wherein said UBASH3B antagonist oligonucleotide is a siRNA that comprises a sequence selected from the group consisting of 5'-CCGGCUUAUUUGAGUGGAC-3' (SEQ ID NO: 1), 5'-CCUCAUAAGAAGCAGCUAC-3' (SEQ ID NO: 2), and 5'-GCACUGCAACUGAGAAAUU-3' (SEQ ID NO: 3).

4. The method of claim 1, wherein said UBASH3B antagonist oligonucleotide is a shRNA that comprises a sequence selected from the group consisting of: 5'-GCTCAGAATCATTTAGCATAT-3' (SEQ ID NO: 41), and 5'-GCGTTCAGACTGCACATAATA-3' (SEQ ID NO: 42).

5. The method of claim 1, further comprising administering an EGFR antagonist.

6. The method of claim 5, wherein said EGFR antagonist is selected from the group consisting of Erlotinib, Gefitinib, CI-1033, GW-2016, PKI-166, EKB-569, and HKI-272.

7. The method of claim 1, wherein the cancer patient has cancer determined to have one or more of the following properties: a higher level of UBASH3B, a higher level of ETS1, a lower level of miR-200a, and a higher level of EGFR relative to normal.

8. A method of inhibiting expression of ubiquitin associated and SH3 domain containing B (UBASH3B) gene in a cancer patient comprising administering a UBASH3B antagonist oligonucleotide to the patient, wherein said UBASH3B antagonist oligonucleotide is selected from the group consisting of an UBASH3B shRNA comprising a sequence selected from the group consisting of 5'-GCTCAGAATCATTTAGCATAT-3' (SEQ ID NO: 41) and 5'-GCGTTCAGACTGCACATAATA-3' (SEQ ID NO: 42) and an UBASH3B siRNA comprising a sequence selected from the group consisting of 5'-CCGGCUUAUUUGAGUGGAC-3' (SEQ ID NO: 1), 5'-CCUCAUAAGAAGCAGCUAC-3' (SEQ ID NO: 2), and 5'-GCACUGCAACUGAGAAAUU-3' (SEQ ID NO: 3), and wherein said cancer is selected from the group consisting of breast cancer, prostate cancer, lung cancer and brain cancer.

9. The method of claim 8, wherein said UBASH3B antagonist oligonucleotide is a siRNA that comprises a sequence selected from the group consisting of 5'-CCGGCUUAUUUGAGUGGAC-3' (SEQ ID NO: 1), 5'-CCUCAUAAGAAGCAGCUAC-3' (SEQ ID NO: 2), and 5'-GCACUGCAACUGAGAAAUU-3' (SEQ ID NO: 3).

10. The method of claim 8, wherein said UBASH3B antagonist oligonucleotide is a shRNA that comprises a sequence selected from the group consisting of: 5'-GCTCAGAATCATTTAGCATAT-3' (SEQ ID NO: 41), and 5'-GCGTTCAGACTGCACATAATA-3' (SEQ ID NO: 42).

* * * * *

SEQUENCE LISTING

```
<160> NUMBER OF SEQ ID NOS: 48

<210> SEQ ID NO 1
<211> LENGTH: 19
<212> TYPE: RNA
<213> ORGANISM: Artificial Sequence
<220> FEATURE:
<223> OTHER INFORMATION: Synthetic UBASH3B siRNA#1

<400> SEQUENCE: 1
ccggcuuauu ugagugggac                                                   19

<210> SEQ ID NO 2
<211> LENGTH: 19
<212> TYPE: RNA
<213> ORGANISM: Artificial Sequence
<220> FEATURE:
<223> OTHER INFORMATION: Synthetic UBASH3B siRNA#2

<400> SEQUENCE: 2
ccucauaaga agcagcuac                                                    19

<210> SEQ ID NO 3
<211> LENGTH: 19
<212> TYPE: RNA
<213> ORGANISM: Artificial Sequence
<220> FEATURE:
<223> OTHER INFORMATION: Synthetic UBASH3B siRNA#3

<400> SEQUENCE: 3
gcacugcaac ugagaaauu                                                    19

<210> SEQ ID NO 4
<211> LENGTH: 19
<212> TYPE: RNA
<213> ORGANISM: Artificial Sequence
<220> FEATURE:
<223> OTHER INFORMATION: Synthetic ETS1 siRNA#1

<400> SEQUENCE: 4
cccagccuau ccagaaucc                                                    19

<210> SEQ ID NO 5
<211> LENGTH: 19
<212> TYPE: RNA
<213> ORGANISM: Artificial Sequence
<220> FEATURE:
<223> OTHER INFORMATION: Synthetic ETS1 siRNA#2

<400> SEQUENCE: 5
```

```
ggaauuacuc acugauaaa                                                    19

<210> SEQ ID NO 6
<211> LENGTH: 24
<212> TYPE: RNA
<213> ORGANISM: Artificial Sequence
<220> FEATURE:
<223> OTHER INFORMATION: Synthetic CBL siRNA

<400> SEQUENCE: 6
ccaaucacaa gcuuaguuau cagg                                              24

<210> SEQ ID NO 7
<211> LENGTH: 20
<212> TYPE: DNA
<213> ORGANISM: Artificial Sequence
<220> FEATURE:
<223> OTHER INFORMATION: Synthetic UBASH3B Forward Primer

<400> SEQUENCE: 7
agcccgcgca caaaaagcct                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic UBASH3B Reverse Primer

<400> SEQUENCE: 8
cggggcaggg ggtcatccag                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic UBASH3A Forward Primer

<400> SEQUENCE: 9
cggagtcgtg ggatcaaaga                                                   20

<210> SEQ ID NO 10
<211> LENGTH: 18
<212> TYPE: DNA
<213> ORGANISM: Artificial Sequence
<220> FEATURE:
<223> OTHER INFORMATION: Synthetic UBASH3A Reverse Primer

<400> SEQUENCE: 10
gcgtcccctg caattctg                                                     18

<210> SEQ ID NO 11
<211> LENGTH: 27
<212> TYPE: DNA
<213> ORGANISM: Artificial Sequence
<220> FEATURE:
<223> OTHER INFORMATION: Synthetic ETS1 Forward Primer

<400> SEQUENCE: 11
cctcggatta cttcattagc tatggta                                           27

<210> SEQ ID NO 12
<211> LENGTH: 23
<212> TYPE: DNA
```

<213> ORGANISM: Artificial Sequence
<220> FEATURE:
<223> OTHER INFORMATION: Synthetic ETS1 Reverse Primer

<400> SEQUENCE: 12
tggagcgtct gataggactc tgt                                              23

<210> SEQ ID NO 13
<211> LENGTH: 29
<212> TYPE: DNA
<213> ORGANISM: Artificial Sequence
<220> FEATURE:
<223> OTHER INFORMATION: Synthetic ACOT9 Forward Primer

<400> SEQUENCE: 13
tggtggataa gattgatatg tgtaagaag                                        29

<210> SEQ ID NO 14
<211> LENGTH: 19
<212> TYPE: DNA
<213> ORGANISM: Artificial Sequence
<220> FEATURE:
<223> OTHER INFORMATION: Synthetic ACOT 9 Reverse Primer

<400> SEQUENCE: 14
tcccgaccca gctaacatg                                                   19

<210> SEQ ID NO 15
<211> LENGTH: 22
<212> TYPE: DNA
<213> ORGANISM: Artificial Sequence
<220> FEATURE:
<223> OTHER INFORMATION: Synthetic CDK6 Forward Primer

<400> SEQUENCE: 15
gagtgttggc tgcatatttg ca                                               22

<210> SEQ ID NO 16
<211> LENGTH: 24
<212> TYPE: DNA
<213> ORGANISM: Artificial Sequence
<220> FEATURE:
<223> OTHER INFORMATION: Synthetic CDK6 Reverse Primer

<400> SEQUENCE: 16
gatcaacatc tgaacttcca cgaa                                             24

<210> SEQ ID NO 17
<211> LENGTH: 21
<212> TYPE: DNA
<213> ORGANISM: Artificial Sequence
<220> FEATURE:
<223> OTHER INFORMATION: Synthetic HYAL3 Forward Primer

<400> SEQUENCE: 17
ggcccctatg tgatcaatgt g                                                21

<210> SEQ ID NO 18
<211> LENGTH: 18
<212> TYPE: DNA
<213> ORGANISM: Artificial Sequence
<220> FEATURE:
<223> OTHER INFORMATION: Synthetic HYAL3 Reverse Primer

<400> SEQUENCE: 18
atggcaccgc tggtgact                                                    18

-continued

<210> SEQ ID NO 19
<211> LENGTH: 20
<212> TYPE: DNA
<213> ORGANISM: Artificial Sequence
<220> FEATURE:
<223> OTHER INFORMATION: Synthetic PSAT1 Forward Primer

<400> SEQUENCE: 19
aatggaggtg ccgcggccat                                             20

<210> SEQ ID NO 20
<211> LENGTH: 21
<212> TYPE: DNA
<213> ORGANISM: Artificial Sequence
<220> FEATURE:
<223> OTHER INFORMATION: Synthetic PSAT1 Reverse Primer

<400> SEQUENCE: 20
gcccggatgc ctcccacaga c                                           21

<210> SEQ ID NO 21
<211> LENGTH: 22
<212> TYPE: DNA
<213> ORGANISM: Artificial Sequence
<220> FEATURE:
<223> OTHER INFORMATION: Synthetic B3GNT5 Forward Primer

<400> SEQUENCE: 21
aagccgacct ccgatttgga ca                                          22

<210> SEQ ID NO 22
<211> LENGTH: 21
<212> TYPE: DNA
<213> ORGANISM: Artificial Sequence
<220> FEATURE:
<223> OTHER INFORMATION: Synthetic B3GNT5 Reverse Primer

<400> SEQUENCE: 22
ccttcaggaa gcgtggtggg c                                           21

<210> SEQ ID NO 23
<211> LENGTH: 20
<212> TYPE: DNA
<213> ORGANISM: Artificial Sequence
<220> FEATURE:
<223> OTHER INFORMATION: Synthetic AGPAT4 Forward Primer

<400> SEQUENCE: 23
gtgtggctgg agcctgtccg                                             20

<210> SEQ ID NO 24
<211> LENGTH: 20
<212> TYPE: DNA
<213> ORGANISM: Artificial Sequence
<220> FEATURE:
<223> OTHER INFORMATION: Synthetic AGPAT4 Reverse Primer

<400> SEQUENCE: 24
tcctgctccc acttgcgcga                                             20

<210> SEQ ID NO 25
<211> LENGTH: 21
<212> TYPE: DNA
<213> ORGANISM: Artificial Sequence
<220> FEATURE:

-continued

<223> OTHER INFORMATION: Synthetic P1 Forward Primer

<400> SEQUENCE: 25
aagcgattct cctgccttag c                                              21

<210> SEQ ID NO 26
<211> LENGTH: 20
<212> TYPE: DNA
<213> ORGANISM: Artificial Sequence
<220> FEATURE:
<223> OTHER INFORMATION: Synthetic P1 Reverse Primer

<400> SEQUENCE: 26
gcatggtggc atgtgactgt                                                20

<210> SEQ ID NO 27
<211> LENGTH: 21
<212> TYPE: DNA
<213> ORGANISM: Artificial Sequence
<220> FEATURE:
<223> OTHER INFORMATION: Synthetic P2 Forward Primer

<400> SEQUENCE: 27
tcaaatcttg gctctgccat t                                              21

<210> SEQ ID NO 28
<211> LENGTH: 24
<212> TYPE: DNA
<213> ORGANISM: Artificial Sequence
<220> FEATURE:
<223> OTHER INFORMATION: Synthetic P2 Reverse Primer

<400> SEQUENCE: 28
tgagccagag gtcaagtatc ttgt                                           24

<210> SEQ ID NO 29
<211> LENGTH: 23
<212> TYPE: DNA
<213> ORGANISM: Artificial Sequence
<220> FEATURE:
<223> OTHER INFORMATION: Synthetic P3 Forward Primer

<400> SEQUENCE: 29
tgtcttatct ccctgcttcc aaa                                            23

<210> SEQ ID NO 30
<211> LENGTH: 18
<212> TYPE: DNA
<213> ORGANISM: Artificial Sequence
<220> FEATURE:
<223> OTHER INFORMATION: Synthetic P3 Reverse Primer

<400> SEQUENCE: 30
gcccggaatt ggtttcct                                                  18

<210> SEQ ID NO 31
<211> LENGTH: 21
<212> TYPE: DNA
<213> ORGANISM: Artificial Sequence
<220> FEATURE:
<223> OTHER INFORMATION: Synthetic P4 Forward Primer

<400> SEQUENCE: 31
cggtccatac caatgaggaa a                                              21

```
<210> SEQ ID NO 32
<211> LENGTH: 20
<212> TYPE: DNA
<213> ORGANISM: Artificial Sequence
<220> FEATURE:
<223> OTHER INFORMATION: Synthetic P4 Reverse Primer

<400> SEQUENCE: 32
cactgcggtg ccttagacaa                                                   20

<210> SEQ ID NO 33
<211> LENGTH: 19
<212> TYPE: DNA
<213> ORGANISM: Artificial Sequence
<220> FEATURE:
<223> OTHER INFORMATION: Synthetic P5 Forward Primer

<400> SEQUENCE: 33
cggctgattg ggaactcaa                                                    19

<210> SEQ ID NO 34
<211> LENGTH: 20
<212> TYPE: DNA
<213> ORGANISM: Artificial Sequence
<220> FEATURE:
<223> OTHER INFORMATION: Synthetic P5 Reverse Primer

<400> SEQUENCE: 34
gatcctgcaa aacccaaagg                                                   20

<210> SEQ ID NO 35
<211> LENGTH: 20
<212> TYPE: DNA
<213> ORGANISM: Artificial Sequence
<220> FEATURE:
<223> OTHER INFORMATION: Synthetic P6 Forward Primer

<400> SEQUENCE: 35
gcccataagg ttgggatcct                                                   20

<210> SEQ ID NO 36
<211> LENGTH: 19
<212> TYPE: DNA
<213> ORGANISM: Artificial Sequence
<220> FEATURE:
<223> OTHER INFORMATION: Synthetic P6 Reverse Primer

<400> SEQUENCE: 36
tgcgggcaag agctgtagt                                                    19

<210> SEQ ID NO 37
<211> LENGTH: 17
<212> TYPE: DNA
<213> ORGANISM: Artificial Sequence
<220> FEATURE:
<223> OTHER INFORMATION: Synthetic P7 Forward Primer

<400> SEQUENCE: 37
cgggagcgtg ggtgttc                                                      17

<210> SEQ ID NO 38
<211> LENGTH: 23
<212> TYPE: DNA
<213> ORGANISM: Artificial Sequence
<220> FEATURE:
<223> OTHER INFORMATION: Synthetic P7 Reverse Primer
```

<400> SEQUENCE: 38
gcttctcctt ctgattccat cct                                            23

<210> SEQ ID NO 39
<211> LENGTH: 22
<212> TYPE: DNA
<213> ORGANISM: Artificial Sequence
<220> FEATURE:
<223> OTHER INFORMATION: Synthetic P8 Forward Primer

<400> SEQUENCE: 39
tgcctgtaat cccagctact tg                                             22

<210> SEQ ID NO 40
<211> LENGTH: 20
<212> TYPE: DNA
<213> ORGANISM: Artificial Sequence
<220> FEATURE:
<223> OTHER INFORMATION: Synthetic P8 Reverse Primer

<400> SEQUENCE: 40
cctccaccta ctgggctcaa                                                20

<210> SEQ ID NO 41
<211> LENGTH: 21
<212> TYPE: DNA
<213> ORGANISM: Artificial Sequence
<220> FEATURE:
<223> OTHER INFORMATION: Synthetic TRCN0000099665

<400> SEQUENCE: 41
gctcagaatc atttagcata t                                              21

<210> SEQ ID NO 42
<211> LENGTH: 21
<212> TYPE: DNA
<213> ORGANISM: Artificial Sequence
<220> FEATURE:
<223> OTHER INFORMATION: Synthetic TRCN0000099669

<400> SEQUENCE: 42
gcgttcagac tgcacataat a                                              21

<210> SEQ ID NO 43
<211> LENGTH: 23
<212> TYPE: RNA
<213> ORGANISM: Artificial Sequence
<220> FEATURE:
<223> OTHER INFORMATION: Synthetic UBASH3B-MRE1

<400> SEQUENCE: 43
cuagccccca uacaccagug uug                                            23

<210> SEQ ID NO 44
<211> LENGTH: 23
<212> TYPE: RNA
<213> ORGANISM: Artificial Sequence
<220> FEATURE:
<223> OTHER INFORMATION: Synthetic UBASH3B-MRE2

<400> SEQUENCE: 44
aauccgguaa ugccccagug uua                                            23

<210> SEQ ID NO 45
<211> LENGTH: 23

```
<212> TYPE: RNA
<213> ORGANISM: Artificial Sequence
<220> FEATURE:
<223> OTHER INFORMATION: UBASH3B-MRE3

<400> SEQUENCE: 45
auggaguuca gauuacagug uuu                                          23

<210> SEQ ID NO 46
<211> LENGTH: 23
<212> TYPE: RNA
<213> ORGANISM: Artificial Sequence
<220> FEATURE:
<223> OTHER INFORMATION: Synthetic UBASH3B-MRE4

<400> SEQUENCE: 46
ggcacucugc aaguccagug uuu                                          23

<210> SEQ ID NO 47
<211> LENGTH: 22
<212> TYPE: RNA
<213> ORGANISM: Artificial Sequence
<220> FEATURE:
<223> OTHER INFORMATION: Synthetic miR200a

<400> SEQUENCE: 47
uaacacuguc ugguaacgau gu                                           22

<210> SEQ ID NO 48
<211> LENGTH: 7
<212> TYPE: RNA
<213> ORGANISM: Artificial Sequence
<220> FEATURE:
<223> OTHER INFORMATION: Synthetic Mutant seq

<400> SEQUENCE: 48 gcagagc                                                             7
```